(12) United States Patent
Cassayre et al.

(10) Patent No.: US 7,960,401 B2
(45) Date of Patent: Jun. 14, 2011

(54) SPIROPIPERIDINE DERIVATIVES FOR CONTROLLING PESTS

(75) Inventors: Jérôme Cassayre, Basel (CH); Louis-Pierre Molleyres, Basel (CH); Peter Maienfisch, Basel (CH); Fredrik Cederbaum, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 944 days.

(21) Appl. No.: 10/581,176

(22) PCT Filed: Dec. 9, 2004

(86) PCT No.: PCT/IB2004/004083
§ 371 (c)(1),
(2), (4) Date: Jan. 29, 2007

(87) PCT Pub. No.: WO2005/061500
PCT Pub. Date: Jul. 7, 2005

(65) Prior Publication Data
US 2007/0135408 A1 Jun. 14, 2007

(30) Foreign Application Priority Data
Dec. 12, 2003 (GB) .................................. 0328905.5

(51) Int. Cl.
*A61K 31/438* (2006.01)
*C07D 471/20* (2006.01)
*A01N 43/40* (2006.01)

(52) U.S. Cl. ............. 514/278; 546/17; 546/18; 504/245

(58) Field of Classification Search .................. 514/278; 546/17, 18; 504/101, 245
See application file for complete search history.

(56) References Cited

FOREIGN PATENT DOCUMENTS

| WO | 95-01358 A | 1/1995 |
|---|---|---|
| WO | 00-27845 A | 5/2000 |
| WO | 02-094825 A | 11/2002 |
| WO | 02/094825 A1 | 11/2002 |
| WO | 03-106457 A | 12/2003 |

OTHER PUBLICATIONS

Ciganek: "Tertiary Carbinamines by Addition of Organocerium Reagents to Nitriles". J. Org. Chem., vol. 57, 1992, pp. 4521-4527, Compound 23.
Genin et al: "Design & synthesis of a conformationally constrained analog of the bis(heteroaryl)piperazine (BHAP), HIV-1 reverse transcriptase inhibitor atevirdine". Bioorganic & Medical Chemistry Letters, vol. 5, No. 16, 1995, pp. 1875-1880, Compound I.
International Search Report (PCT/IB2004/004083) mailed May 6, 2005.
English translation of Taiwanese Office Action (ROC Appln. No. 093137173; filing date Dec. 2, 2004), search completed Aug. 3, 2010.

*Primary Examiner* — Charanjit S Aulakh
(74) *Attorney, Agent, or Firm* — William A. Teoli, Jr.

(57) ABSTRACT

The use of a compound of formula I

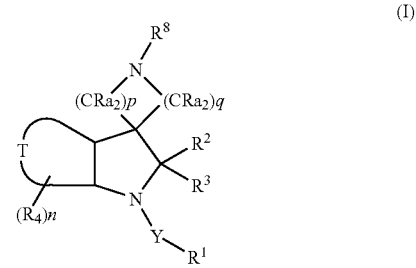

Y is a single bond, C=O, C=S or S(O)$_m$ where m is 0, 1 or 2; the ring represented by T is a 5 or 6 membered heteroaromatic and $R^1$, $R^2$, $R^3$, $R^8$ and Ra are specified organic groups and p is 0, 1, 2, 3, 4, 5 or 6; q is 0, 1, 2, 3, 4, 5 or 6; p+q is 1, 2, 3, 4, 5 or 6; or salts or N-oxides thereof or compositions containing them in controlling insects, acarines, nematodes or molluscs; novel compounds are also provided.

11 Claims, No Drawings

SPIROPIPERIDINE DERIVATIVES FOR CONTROLLING PESTS

This application is a 371 of International Application No. PCT/IB2004/004083 filed Dec. 9, 2004, which claims priority to GB 0328905.5 filed Dec. 12, 2003, the contents of which are incorporated herein by reference.

The present invention relates to hetero-spiroindoline derivatives, to processes for preparing them, to insecticidal, acaricidal, molluscicidal and nematicidal compositions comprising them and to methods of using them to combat and control insect, acarine, mollusc and nematode pests.

Aza-spiroindolines with pharmaceutical properties are disclosed in for example WO02/94825 and WO00/27845. Synthetic routes to selected compounds are described for instance in Bioorganic & Medicinal Chemistry Letters (1995), 5, 1875 and Tetrahedron Letters (2001) 42, 999.

It has now surprisingly been found that certain hetero-spiroindolines have insecticidal properties.

The present invention therefore provides a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I):

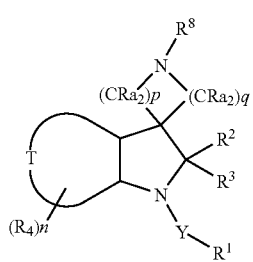

wherein Y is a single bond, C=O, C=S or S(O)$_m$ where m is 0, 1 or 2;

R$^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or NR$^{13}$R$^{14}$ where R$^{13}$ and R$^{14}$ are independently hydrogen, COR$^{15}$, optionally substituted alkyl, optionally substituted aryl, optionally substituted heteroaryl, optionally substituted heterocyclyl or R$^{13}$ and R$^{14}$ together with the N atom to which they are attached form a group —N=C(R$^{16}$)—NR$^{17}$R$^{18}$; R$^{15}$ is H, optionally substituted alkyl, optionally substituted alkoxy, optionally substituted aryl, optionally substituted aryloxy optionally substituted heteroaryl, optionally substituted heteroaryloxy or NR$^{19}$R$^{20}$; R$^{16}$, R$^{17}$ and R$^{18}$ are each independently H or lower alkyl; R$^{19}$ and R$^{20}$ are independently optionally substituted alkyl, optionally substituted aryl or optionally substituted heteroaryl;

R$^2$ and R$^3$ are independently hydrogen, halogen, cyano, optionally substituted alkyl, optionally substituted alkoxy or optionally substituted aryl; the ring

is a 5 or 6 membered heteroaromatic ring;

each R$^4$ is independently halogen, nitro, cyano, optionally substituted C$_{1-8}$ alkyl, optionally substituted C$_{2-6}$ alkenyl, optionally substituted C$_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted C$_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or R$^{21}$R$^{22}$N where R$^{21}$ and R$^{22}$ are, independently, hydrogen, C$_{1-8}$ alkyl, C$_{3-7}$ cycloalkyl, C$_{3-6}$ alkenyl, C$_{3-6}$ alkynyl, C$_{3-7}$ cycloalkyl(C$_{1-4}$)alkyl, C$_{2-6}$ haloalkyl, C$_{1-6}$ alkoxy(C$_{1-6}$)alkyl, C$_{1-6}$ alkoxycarbonyl or R$^{21}$ and R$^{22}$ together with the N atom to which they are attached form a five, six or seven-membered heterocyclic ring which may contain one or two further heteroatoms selected from O, N or S and which may be optionally substituted by one or two C$_{1-6}$ alkyl groups, or 2 6, or 7 membered carbocyclic or heterocyclic ring which may be optionally substituted by halogen;n is 0, 1, 2 or 3;

each Ra is independently hydrogen, halogen, hydroxy, cyano, optionally substituted C$_{1-8}$ alkyl, optionally substituted C$_{2-6}$ alkenyl, optionally substituted C$_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted C$_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or R$^{23}$R$^{24}$N where R$^{23}$ and R$^{24}$ are, independently, hydrogen, C$_{1-8}$ alkyl, C$_{3-7}$ cycloalkyl, C$_{3-6}$ alkenyl, C$_{3-6}$ alkynyl, C$_{3-7}$ cycloalkyl (C$_{1-4}$)alkyl, C$_{2-6}$ haloalkyl, C$_{1-6}$ alkoxy(C$_{1-6}$)alkyl, C$_{1-6}$ alkoxycarbonyl or R$^{23}$ and R$^{24}$ together with the N atom to which they are attached form a five, six or seven-membered heterocyclic ring which may contain one or two further heteroatoms selected from O, N or S and which may be optionally substituted by one or two C$_{1-6}$ alkyl groups, or two Ra groups attached to the same carbon atom are =O or two Ra groups attached to adjacent carbon atoms form a bond, or two Ra groups together with the carbon atom to which they are attached form a three- to seven-membered ring, that may be saturated or unsaturated, and that may contain one or two hetero atoms selected from the group consisting of N, O and S, and which may be optionally substituted by one or two C$_{1-6}$ alkyl groups; or two Ra groups together form a group —CH$_2$—, —CH=CH— or —CH$_2$CH$_2$; p is 0, 1, 2, 3, 4, 5 or 6; q is 0, 1, 2, 3, 4, 5 or 6 provided that p+q is 1, 2, 3, 4, 5 or 6;

R$^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl; or salts or N-oxides thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are suitably $C_1$ to $C_{12}$ alkyl groups, but are preferably $C_1$-$C_{10}$, more preferably $C_1$-$C_8$, even more preferably preferably $C_1$-$C_6$ and most preferably $C_1$-$C_4$ alkyl groups.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, NCS—, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy ($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)-alkoxy (where the aryl group is optionally substituted), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri($C_{1-4}$)alkylsilyl, aryldi($C_{1-4}$)alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl) aminocarbonyl, N—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), di($C_{1-6}$)alkylaminocarbonyloxy, oximes such as =NOalkyl, =NOhaloalkyl and =NOaryl (itself optionally substituted), aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{2-6}$ alkynylcarbonyl, optionally substituted arylcarbonyl (for example benzoyl) or optionally substituted heteroarylcarbonyl.

Halogen is fluorine, chlorine, bromine or iodine.

Haloalkyl groups are alkyl groups which are substituted with one or more of the same or different halogen atoms and are, for example, $CF_3$, $CF_2Cl$, $CF_3CH_2$ or $CHF_2CH_2$.

In the context of the present specification the terms "aryl" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl,1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2, 1, 3-benzoxadiazole quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, 2,1,3-benzoxadiazole and thiazolyl.

The terms heterocycle and heterocyclyl refer to a nonaromatic ring containing up to 10 atoms including one or more (preferably one or two) heteroatoms selected from O, S and N. Examples of such rings include 1,3-dioxolane, tetrahydrofuran and morpholine.

When present, the optional substituents on heterocyclyl include $C_{1-6}$ alkyl and $C_{1-6}$ haloalkyl as well as those optional substituents given above for an alkyl moiety.

Cycloalkyl includes cyclopropyl, cyclopentyl and cyclohexyl.

Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups.

When present, the optional substituents on aryl or heteroaryl are selected independently, from halogen, nitro, cyano, NCS—, $C_{1-6}$ alkyl, $C_{1-6}$ haloalkyl, $C_{1-6}$ alkoxy-($C_{1-6}$) alkyl, $C_{2-6}$ alkenyl, $C_{2-6}$ haloalkenyl, $C_{2-6}$ alkynyl, $C_{3-7}$ cycloalkyl substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy(Cl-lo)alkoxy, tri(Cl-$_4$)alkyl-silyl($C_{1-6}$)alkoxy, $C_{1-6}$ alkoxycarbonyl($C_{1-10}$) alkoxy, $C_{1-10}$ haloalkoxy, aryl ($C_{1-4}$)alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio $C_{3-7}$ cycloalkylthio (where the cycloalkyl group is optionally substituted with $C_{1-6}$ alkyl or halogen), tri($C_{1-4}$)-alkylsilyl($C_{1-6}$)alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, tri($C_{1-4}$)alkylsilyl, aryldi($C_{1-4}$)-alkylsilyl, ($C_{1-4}$)alkyldiarylsilyl, triarylsilyl, $C_{1-0}$ alkylcarbonyl, $HO_2C$, $C_{1-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)—N—($C_{1-3}$ alkoxy)aminocarbonyl, $C_{1-6}$ alkylcarbonyloxy, arylcarbonyloxy, di($C_{1-6}$)alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N-($C_{1-6}$)alkylcarbonyl-N—($C_{1-6}$)alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include aryl carbonyl amino (where the aryl group is substituted by $C_{1-6}$ alkyl or halogen), ($C_{1-6}$) alkyloxycarbonylamino ($C_{1-6}$)alkyloxycarbonyl-N—($C_{1-6}$) alkylamino, aryloxycarbonylamino (where the aryl group is substituted by $C_{1-6}$ alkyl or halogen), aryloxycarbonyl-N—($C_{1-6}$)alkylamino, (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$)alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonyl amino, di($C_{1-6}$) alkylaminocarbonyl amino, arylaminocarbonyl amino where the aryl group is substituted by $C_{1-6}$ alkyl or halogen), aryl-N—($C_{1-6}$)alkylaminocarbonylamino where the aryl group is substituted by $C_{1-6}$ alkyl or halogen), $C_{1-6}$ alkylaminocarbonyl-N—($C_{1-6}$)alkyl amino; di(CI 6)alkylaminocarbonyl-N—($C_{1-6}$)alkyl amino, arylaminocarbonyl-N—($C_{1-6}$)alkyl amino where the aryl group is substituted by $C_{1-6}$ alkyl or halogen) and aryl-N—($C_{1-6}$)alkylaminocarbonyl-N—($C_{1-6}$)alkyl amino where the aryl group is substituted by $C_{1-6}$ alkyl or halogen).

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, $R^{25}R^{26}N$ or $R^{27}R^{28}NC(O)$; wherein $R^{25}$, $R^{26}$, $R^{27}$ and $R^{28}$ are, independently hydrogen or $C_{1-6}$ alkyl. Further preferred substituents are aryl and heteroaryl groups.

Haloalkenyl groups are alkenyl groups which are substituted with one or more of the same or different halogen atoms.

It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed byjoining two groups on an N atom, the resulting rings are suitably pyrrolidine, piperidine, thiomorpholine and morpholine each of which may be substituted by one or two independently selected ($C_{1-6}$) alkyl groups.

Preferably the optional substituents on an alkyl moiety include one or more of halogen, nitro, cyano, $HO_2C$, $C_{1-10}$ alkoxy (itself optionally substituted by $C_{1-10}$ alkoxy), aryl ($C_{1-4}$)alkoxy, $C_{1-10}$ alkylthio, $C_{1-10}$ alkylcarbonyl, $C_{1-10}$ alkoxycarbonyl, $C_{1-6}$ alkylaminocarbonyl, di($C_{1-6}$ alkyl)aminocarbonyl, ($C_{1-6}$)alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with ($C_{1-6}$)alkyl or halogen), $C_{3-7}$ cycloalkyloxy, $C_{5-7}$ cycloalkenyl, $C_{1-6}$ alkylsulfonyl, $C_{1-6}$ alkylsulfinyl, tri($C_{1-4}$)alkylsilyl, tri($C_{1-4}$)alkylsilyl($C_{1-6}$)alkoxy, aryldi ($C_{1-4}$)alkylsilyl, ($C_{1-4}$)alkyldiarylsilyl and triarylsilyl.

Preferably the optional substituents on alkenyl or alkynyl include one or more of halogen, aryl and $C_{3-7}$ cycloalkyl.

A preferred optional substituent for heterocyclyl is $C_{1-6}$ alkyl.

Preferably the optional substituents for cycloalkyl include halogen, cyano and $C_{1-3}$ alkyl.

Preferably the optional substituents for cycloalkenyl include $C_{1-3}$ alkyl, halogen and cyano.

Preferably Y is a single bond, C=O or S(O)m where m is 0, 1 or 2.

More preferably Y is a single bond, C=O or $SO_2$.

Yet more preferably Y is a single bond or C=O.

Most preferably Y is C=O.

Preferably $R^1$ is hydrogen, $C_{1-6}$ alkyl, $C_{1-6}$ cyanoalkyl, $C_{1-6}$ haloalkyl, $C_{3-7}$ cycloalkyl($C_{1-4}$)alkyl, $C_{1-6}$ alkoxy($C_{1-6}$)alkyl, heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), aryl($C_{1-6}$)alkyl (wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), $C_{1-6}$ alkylcarbonylamino($C_{1-6}$)alkyl, aryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, phenoxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyloxy (optionally substituted by halo, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ alkynyl, $C_{3-6}$ cycloalkyl, $C_{5-7}$cycloalkenyl, heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl, $C_{1-6}$ haloalkyl, $C_{1-6}$ alkoxy($C_{1-6}$)alkyl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino or $C_4$ alkoxycarbonyl), phenyl ($C_{1-6}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl ($C_{1-6}$) alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen) or heteroaryl (which may be optionally substituted by halo, nitro, cyano, $C_{1-6}$ alkyl, $C_{1-6}$ haloalkyl, $C_{1-6}$ alkoxy or $C_{1-6}$ haloalkoxy, $C_{1-4}$ alkoxycarbonyl $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), amino, $C_{1-6}$ alkylamino or phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino)).

More preferably $R^1$ is $C_{1-6}$ alkyl, $C_{1-6}$ haloalkyl, $C_{1-6}$ alkoxy($C_{1-6}$)alkyl, heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, $C_{2-6}$ alkenyl, heterocyclyl (optionally substituted by halo, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl or $C_{1-6}$ haloalkyl, $C_{1-6}$ alkoxy($C_{1-6}$)alkyl, $C_{2-6}$ alkylcarbonyl, phenylcarbonyl, (where the phenyl is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen) or heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen).

Even more preferably $R^1$ is $C_{1-6}$ alkyl, $C_{1-6}$ haloalkyl, heteroaryl($C_{1-3}$)alkyl (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring), heteroaryl (optionally substituted by halo, cyano, $C_{1-6}$ alkyl, $C_{1-6}$ haloalkyl and where the heteroaryl group is a pyridine, pyrimidine, 2,1,3-benzoxadiazole, pyrazine or pyridazine ring), $C_{1-6}$ alkoxy, $C_{1-6}$ alkoxy($C_{1-6}$)alkyl, $C_{1-6}$ alkylamino, $C_{1-6}$ alkoxy($C_{1-6}$)alkylamino or heteroaryl($C_{1-3}$)alkylamino (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring).

Most preferably $R^1$ is pyridyl (optionally substituted by halo, $C_{1-3}$ alkyl or $C_{1-3}$ haloalkyl) especially halo-substituted pyridyl.

It is preferred that $R^2$ and $R^3$ are independently hydrogen, $C_{1-6}$ alkyl, $C_{1-6}$ haloalkyl, $C_{1-6}$ alkoxy or cyano.

More preferably $R^2$ and $R^3$ are independently hydrogen, halogen, $C_{1-2}$, $C_{1-2}$ haloalkyl, $C_{1-2}$ alkoxy, cyano.

Even more preferably $R^2$ and $R^3$ are independently hydrogen or $C_{1-4}$ alkyl.

Yet more preferably $R^2$ and $R^3$ are independently hydrogen or methyl.

Most preferably $R^2$ and $R^3$ are both hydrogen.

Preferably each $R^4$ is independently halogen, cyano, $C_{1-8}$alkyl, $C_{1-8}$haloalkyl, $C_{1-6}$ cyanoalkyl, $C_{1-6}$ alkoxy($C_{1-6}$) alkyl, $C_{3-7}$ cycloalkyl($C_{1-6}$)alkyl, $C_{5-6}$ cycloalkenyl($C_{1-6}$) alkyl, $C_{3-6}$ alkenyloxy($C_{1-6}$)alkyl, $C_{3-6}$ alkynyloxy($C_{1-6}$) alkyl, aryloxy($C_{1-6}$)alkyl, $C_{1-6}$ carboxalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)-alkyl, $C_{1-6}$ alkoxycarbonyl($C_{1-6}$) alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$)alkyl, di($C_{1-6}$)alkylaminocarbonyl ($C_{1-6}$)alkyl, phenyl($C_{1-4}$)alkyl (wherein the phenyl group is optionally substituted by halogen, $C_{1-4}$ alkyl, $Cl_{-4}$ alkoxy, $C_{1-4}$ haloalkyl, $C_{1-4}$ haloalkoxy, CN, $NO_2$, aryl, heteroaryl, amino or dialkylamino), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, aminocarbonyl($C_{2-6}$)alkenyl, $C_{1-6}$ alkylaminocarbonyl($C_{2-6}$)alkenyl, di($C_{1-6}$)alkylaminocarbonyl($C_{2-6}$)alkenyl, phenyl($C_{2-4}$)-alkenyl, (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkynyl, trimethylsilyl($C_{2-6}$)alkynyl, aminocarbonyl($C_{2-6}$)alkynyl, $C_{1-6}$ alkylaminocarbonyl($C_{2-6}$) alkynyl, di($C_{1-6}$)alkylaminocarbonyl($C_{2-6}$)alkynyl, $C_{1-6}$ alkoxycarbonyl, $C_{3-7}$ cycloalkyl, $C_{3-7}$ halocycloalkyl, $C_{3-7}$ cyanocycloalkyl, $C_{1-3}$ alkyl($C_{3-7}$)-cycloalkyl, $C_{1-3}$ alkyl ($C_{3-7}$)halocycloalkyl,phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), or 2 adjacent groups $R^4$ together with the carbon atoms to which they are attached form a 4, 5, 6 or 7 membered carbocyclic or heterocyclic ring which may be optionally substituted by halogen, $C_{1-8}$ alkoxy, $C_{1-6}$ haloalkoxy, phenoxy (optionally substituted by halo, nitro, cyano, $C_{1-6}$ alkyl, $C_{1-6}$ haloalkyl, $C1_6$ alkoxy or $C_{1-6}$ haloalkoxy), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or $R^{19}R^{20}N$ where $R^{19}$ and $R^{20}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalky alkoxycarbonyl or $R^{19}$ and $R^{20}$ together with the N atom to which they are attached form a five, six or seven-membered heterocyclic ring which may contain one or two further heteroatoms selected from O, N or S and which may be optionally substituted by one or two $C_{1-6}$ alkyl groups; n is 0, 1, 2 or 3.

More preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$) alkyl, $C_{2-6}$ alkynyl, trimethylsilyl($C_{2-6}$)alkynyl, $C_{1-6}$ alkoxycarbonyl, $C_{3-7}$ cycloalkyl, $C_{1-3}$ alkyl ($C_{3-7}$) cycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkoxy, $C_{1-6}$ haloalkoxy, phenoxy (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-3}$ alkyl, $C_{1-3}$ haloalkyl, $C_{1-3}$ alkoxy or $C_{1-3}$ haloalkoxy), di($C_{1-8}$)alkylamino, or 2 adjacent groups $R^4$ together with the carbon atoms to which they are attached form a 4, 5, 6 or 7 membered carbocyclic or heterocyclic ring which may be optionally substituted by halogen; n is 0, 1, 2 or 3.

Even more preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$)alkyl, $C_{2-6}$ alkynyl, heterocyclyl (optionally substituted by $C_{1-6}$ alkyl), $C_{1-8}$ alkoxy, $C_{1-6}$ haloalkoxy, phenoxy (optionally substituted by halo, cyano, $C_{1-3}$ alkyl or $C_{1-3}$ haloalkyl), heteroaryloxy (optionally substituted by halo, cyano, $C_{1-3}$ alkyl or $C_{1-3}$ haloalkyl), di($C_{1-8}$)alkylamino or 2 adjacent groups $R^4$ together with the carbon atoms to which they are attached form a 4, 5, 6 or 7 membered carbocyclic or heterocyclic ring which may be optionally substituted by halogen; n is 0, 1, 2 or 3.

Yet more preferably each $R^4$ is independently fluoro, chloro, bromo, cyano, $C_{1-4}$ alkyl, $C_{1-4}$ haloalkyl, $C_{1-4}$ cyanoalkyl or $C_{1-3}$ alkoxy($C_{1-3}$)alkyl; n is 0, 1 or 2.

Most preferably each $R^4$ is independently fluoro, chloro, bromo, $C_{1-4}$ alkyl or $C_{1-4}$ haloalkyl; n is 1 or 2.

Preferably $R^8$ is $C_{1-10}$ alkyl, $C_{1-10}$ haloalkyl, aryl($C_{1-6}$)alkyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), arylcarbonyl-($C_{1-6}$)alkyl (wherein the aryl group may be optionally substituted by halogen, $C_{1-4}$ alkyl, $C_{1-4}$ alkoxy, $C_{1-4}$haloalkyl, $C_{1-4}$ haloalkoxy, CN, $NO_2$, aryl, heteroaryl, amino or dialkylamino and the alkyl group may be optionally substituted by aryl), $C_{2-8}$ alkenyl, $C_{2-8}$ haloalkenyl, aryl($C_{2-6}$)-alkenyl (wherein the aryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), heteroaryl($C_{2-6}$)-alkenyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), $C_{2-6}$ alkynyl, phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{3-7}$ cycloalkyl, $C_{1-6}$ alkoxycarbonyl, $C_{1-6}$ alkylcarbonyl, $C_{1-6}$ haloalkylcarbonyl or aryl($C_{2-6}$)alkenylcarbonyl (wherein the aryl group may be optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), or $—C(R^{51})(R^{52})—[CR^{53}=CR^{54}]z-R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

More preferably $R^8$ is phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl ($C_{2-6}$)alkenyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{2-6}$)alkenyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, or $—C(R^{51})(R^{52})—[CR^{53}=CR^{54}]z-R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

Most preferably $R^8$ is $—C(R^{51})(R^{52})—[CR^{53}=CR^{54}]z-R^{55}$ where z is 1 or 2, preferably 1, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

$R^{51}$ and $R^{52}$ are preferably hydrogen.

$R^{53}$ and $R^{54}$ are preferably hydrogen or halogen, especially hydrogen.

$R^{55}$ is preferably phenyl substituted with one to three substituents selected from halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

It is preferred that the ring

a 5 or 6 membered heteroaromatic ring wherein the ring members are each independently CH, S, N, $NR^4$, O, or $CR^4$ provided that at least one ring member is other than CH or CR4 and that there are no more than one O or S atoms present in the ring.

More preferably the ring

is a pyridine, pyrimidine, pyrazine, pyridazine, triazine, furan, thiophene, pyrrole, imidazole, pyrazole, oxazole, thiazole, isoxazole, isothiazole, [1,2,3]triazole, [1,2,3]oxadiazole or [1,2,3]thiadiazole.

Preferably each Ra is independently hydrogen, halo, cyano, $C_{1-3}$ alkyl, hydroxy or two Ra groups together with the carbon atom to which they are attached form a carbonyl group More preferably each Ra is independently hydrogen, fluoro, methyl, hydroxy or two Ra groups together with the carbon atom to which they are attached form a carbonyl group Most preferably each Ra is hydrogen.

Preferably p is 1, 2 or 3 and q is 1, 2 or 3 and p+q is 3, 4 or 5.

More preferably p is 1 or 2 and q is 2.

Most preferably p and q are both 2.

One group of preferred compounds of formula (I) are those where Y is C(O) and $R^1$ is $NR^{13}R^{14}$ where $R^{13}$ and $R^{14}$ are as defined above.

Certain compounds of formula I are novel. One group of novel compounds is that of formula I'

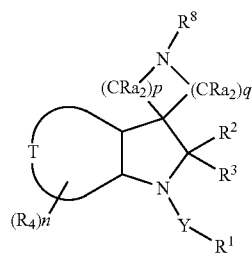

(I')

wherein Y is C=O, C=S;

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$ where $R^{13}$ and $R^{14}$ are independently hydrogen, $COR^5$, optionally substituted alkyl, optionally substituted aryl, optionally substituted heteroaryl, optionally substituted heterocyclyl or $R^{13}$ and $R^{14}$ together with the N atom to which they are attached form a group —N=C($R^{16}$)—$NR^{17}R^{18}$; $R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$; $R^{16}$, $R^{17}$ and $R^{18}$ are each independently H or lower alkyl; $R^{19}$ and $R^{20}$ are independently optionally substituted alkyl, optionally substituted aryl or optionally substituted heteroaryl;

$R^2$ and $R^3$ are independently hydrogen, halogen, cyano, optionally substituted alkyl, optionally substituted alkoxy or optionally substituted aryl;

the ring

is a 5 or 6 membered heteroaromatic ring;

each $R^4$ is independently halogen, nitro, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or $R^{21}R^{22}N$ where $R^{21}$ and $R^{22}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{21}$ and $R^{22}$ together with the N atom to which they are attached form a five, six or seven-membered heterocyclic ring which may contain one or two further heteroatoms selected from O, N or S and which may be optionally substituted by one or two $C_{1-6}$ alkyl groups, or 2 adjacent groups $R^4$ together with the carbon atoms to which they are attached form a 4, 5, 6, or 7 membered carbocyclic or heterocyclic ring which may be optionally substituted by halogen; n is 0, 1, 2 or 3;

each Ra is independently hydrogen, halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$ where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl ($C_{1-4}$)alkyl, $C_{2-6}$ haloalkyl, $C_{1-6}$ alkoxy($C_{1-6}$)alkyl, $C_{1-6}$ alkoxycarbonyl or $R^{23}$ and $R^{24}$ together with the N atom to which they are attached form a five, six or seven-membered heterocyclic ring which may contain one or two further heteroatoms selected from O, N or S and which may be optionally substituted by two Ra groups attached to adjacent carbon atoms form a bond, or two Ra groups together with the carbon atom to which they are attached form a three- to seven-membered ring, that may be saturated or unsaturated, and that may contain one or two hetero atoms selected from the group consisting of N, O and S, and which may be optionally substituted by one or two $C_{1-6}$ alkyl groups; or two Ra groups together form a group —$CH_2$—, —CH=CH— or —$CH_2CH_2$;

p is 0, 1, 2, 3, 4, 5 or 6; q is 0, 1, 2, 3, 4, 5 or 6 provided that p+q is 1, 2, 3, 4, 5 or 6;

$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl; or salts or N-oxides thereof.

The compounds in Tables I- DCCLXVII below illustrate the compounds of the invention.

Table I provides 575 compounds of formula Ia

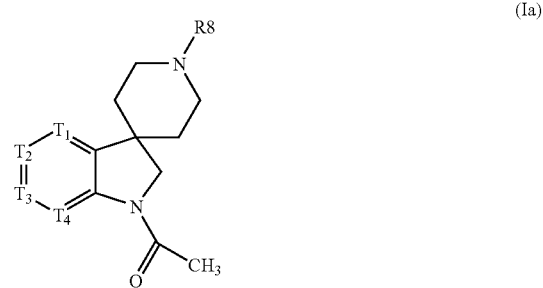

(Ia)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$, are given in Table 1.

TABLE 1

| Compound No | $R^8$ | C—$R^{4a}$ | C—$R^{4b}$ | C—$R^{4c}$ |
|---|---|---|---|---|
| I-1 | 4-chlorobenzyl | CH | CH | CH |
| I-2 | Cinnamyl | CH | CH | CH |
| I-3 | 4-chlorocinnamyl | CH | CH | CH |
| I-4 | 4-fluorocinnamyl | CH | CH | CH |
| I-5 | 4-bromocinnamyl | CH | CH | CH |
| I-6 | 4-trifluoromethylcinnamyl | CH | CH | CH |
| I-7 | 4-trifluoromethoxycinnamyl | CH | CH | CH |
| I-8 | 4-pentafluoroethoxycinnamyl | CH | CH | CH |
| I-9 | 4-methoxycinnamyl | CH | CH | CH |
| I-10 | 4-ethoxycinnamyl | CH | CH | CH |
| I-11 | 4-cyanocinnamyl | CH | CH | CH |
| I-12 | 3-(6-chloro-pyridin-3-yl)-allyl | CH | CH | CH |
| I-13 | 3-(4-chlorophenyl)-but-2-enyl | CH | CH | CH |
| I-14 | 3-(4-chlorophenyl)-3-fluoro-allyl | CH | CH | CH |
| I-15 | 3-chloro-4-fluoro-cinnamyl | CH | CH | CH |
| I-16 | 3,5-dichloro-cinnamyl | CH | CH | CH |
| I-17 | 5-phenyl-penta-2,4-dienyl | CH | CH | CH |
| I-18 | 4-isopropyloxycarbonylamino-cinnamyl | CH | CH | CH |
| I-19 | 3-naphthalen-2-yl-allyl | CH | CH | CH |
| I-20 | 3-(5-trifluoromethyl-pyridin-2-yl)-allyl | CH | CH | CH |
| I-21 | 3-(5-chloro-pyridin-2-yl)-allyl | CH | CH | CH |
| I-22 | 3-pyridin-4-yl-allyl | CH | CH | CH |
| I-23 | 3-(2-Chloro-pyridin-4-yl)-allyl | CH | CH | CH |
| I-24 | 4-chlorobenzyl | CF | CH | CH |
| I-25 | Cinnamyl | CF | CH | CH |
| I-26 | 4-chlorocinnamyl | CF | CH | CH |
| I-27 | 4-fluorocinnamyl | CF | CH | CH |
| I-28 | 4-bromocinnamyl | CF | CH | CH |
| I-29 | 4-trifluoromethylcinnamyl | CF | CH | CH |
| I-30 | 4-trifluoromethoxycinnamyl | CF | CH | CH |
| I-31 | 4-pentafluoroethoxycinnamyl | CF | CH | CH |
| I-32 | 4-methoxycinnamyl | CF | CH | CH |
| I-33 | 4-ethoxycinnamyl | CF | CH | CH |
| I-34 | 4-cyanocinnamyl | CF | CH | CH |
| I-35 | 3-(6-chloro-pyridin-3-yl)-allyl | CF | CH | CH |
| I-36 | 3-(4-chlorophenyl)-but-2-enyl | CF | CH | CH |
| I-37 | 3-(4-chlorophenyl)-3-fluoro-allyl | CF | CH | CH |
| I-38 | 3-chloro-4-fluoro-cinnamyl | CF | CH | CH |
| I-39 | 3,5-dichloro-cinnamyl | CF | CH | CH |
| I-40 | 5-phenyl-penta-2,4-dienyl | CF | CH | CH |
| I-41 | 4-isopropyloxycarbonylamino-cinnamyl | CF | CH | CH |
| I-42 | 3-naphthalen-2-yl-allyl | CF | CH | CH |
| I-43 | 3-(5-trifluoromethyl-pyridin-2-yl)-allyl | CF | CH | CH |
| I-44 | 3-(5-chloro-pyridin-2-yl)-allyl | CF | CH | CH |
| I-45 | 3-pyridin-4-yl-allyl | CF | CH | CH |
| I-46 | 3-(2-Chloro-pyridin-4-yl)-allyl | CF | CH | CH |
| I-47 | 4-chlorobenzyl | CCl | CH | CH |
| I-48 | Cinnamyl | CCl | CH | CH |
| I-49 | 4-chlorocinnamyl | CCl | CH | CH |
| I-50 | 4-fluorocinnamyl | CCl | CH | CH |
| I-51 | 4-bromocinnamyl | CCl | CH | CH |
| I-52 | 4-trifluoromethylcinnamyl | CCl | CH | CH |
| I-53 | 4-trifluoromethoxycinnamyl | CCl | CH | CH |

TABLE 1-continued

| Compound No | R⁸ | C—R⁴ᵃ | C—R⁴ᵇ | C—R⁴ᶜ |
|---|---|---|---|---|
| I-54 | 4-pentafluoroethoxycinnamyl | CCl | CH | CH |
| I-55 | 4-methoxycinnamyl | CCl | CH | CH |
| I-56 | 4-ethoxycinnamyl | CCl | CH | CH |
| I-57 | 4-cyanocinnamyl | CCl | CH | CH |
| I-58 | 3-(6-chloro-pyridin-3-yl)-allyl | CCl | CH | CH |
| I-59 | 3-(4-chlorophenyl)-but-2-enyl | CCl | CH | CH |
| I-60 | 3-(4-chlorophenyl)-3-fluoro-allyl | CCl | CH | CH |
| I-61 | 3-chloro-4-fluoro-cinnamyl | CCl | CH | CH |
| I-62 | 3,5-dichloro-cinnamyl | CCl | CH | CH |
| I-63 | 5-phenyl-penta-2,4-dienyl | CCl | CH | CH |
| I-64 | 4-isopropyloxycarbonylamino-cinnamyl | CCl | CH | CH |
| I-65 | 3-naphthalen-2-yl-allyl | CCl | CH | CH |
| I-66 | 3-(5-trifluoromethyl-pyridin-2-yl)-allyl | CCl | CH | CH |
| I-67 | 3-(5-chloro-pyridin-2-yl)-allyl | CCl | CH | CH |
| I-68 | 3-pyridin-4-yl-allyl | CCl | CH | CH |
| I-69 | 3-(2-Chloro-pyridin-4-yl)-allyl | CCl | CH | CH |
| I-70 | 4-chlorobenzyl | CBr | CH | CH |
| I-71 | Cinnamyl | CBr | CH | CH |
| I-72 | 4-chlorocinnamyl | CBr | CH | CH |
| I-73 | 4-fluorocinnamyl | CBr | CH | CH |
| I-74 | 4-bromocinnamyl | CBr | CH | CH |
| I-75 | 4-trifluoromethylcinnamyl | CBr | CH | CH |
| I-76 | 4-trifluoromethoxycinnamyl | CBr | CH | CH |
| I-77 | 4-pentafluoroethoxycinnamyl | CBr | CH | CH |
| I-78 | 4-methoxycinnamyl | CBr | CH | CH |
| I-79 | 4-ethoxycinnamyl | CBr | CH | CH |
| I-80 | 4-cyanocinnamyl | CBr | CH | CH |
| I-81 | 3-(6-chloro-pyridin-3-yl)-allyl | CBr | CH | CH |
| I-82 | 3-(4-chlorophenyl)-but-2-enyl | CBr | CH | CH |
| I-83 | 3-(4-chlorophenyl)-3-fluoro-allyl | CBr | CH | CH |
| I-84 | 3-chloro-4-fluoro-cinnamyl | CBr | CH | CH |
| I-85 | 3,5-dichloro-cinnamyl | CBr | CH | CH |
| I-86 | 5-phenyl-penta-2,4-dienyl | CBr | CH | CH |
| I-87 | 4-isopropyloxycarbonylamino-cinnamyl | CBr | CH | CH |
| I-88 | 3-naphthalen-2-yl-allyl | CBr | CH | CH |
| I-89 | 3-(5-trifluoromethyl-pyridin-2-yl)-allyl | CBr | CH | CH |
| I-90 | 3-(5-chloro-pyridin-2-yl)-allyl | CBr | CH | CH |
| I-91 | 3-pyridin-4-yl-allyl | CBr | CH | CH |
| I-92 | 3-(2-Chloro-pyridin-4-yl)-allyl | CBr | CH | CH |
| I-93 | 4-chlorobenzyl | CCN | CH | CH |
| I-94 | Cinnamyl | CCN | CH | CH |
| I-95 | 4-chlorocinnamyl | CCN | CH | CH |
| I-96 | 4-fluorocinnamyl | CCN | CH | CH |
| I-97 | 4-bromocinnamyl | CCN | CH | CH |
| I-98 | 4-trifluoromethylcinnamyl | CCN | CH | CH |
| I-99 | 4-trifluoromethoxycinnamyl | CCN | CH | CH |
| I-100 | 4-pentafluoroethoxycinnamyl | CCN | CH | CH |
| I-101 | 4-methoxycinnamyl | CCN | CH | CH |
| I-102 | 4-ethoxycinnamyl | CCN | CH | CH |
| I-103 | 4-cyanocinnamyl | CCN | CH | CH |
| I-104 | 3-(6-chloro-pyridin-3-yl)-allyl | CCN | CH | CH |
| I-105 | 3-(4-chlorophenyl)-but-2-enyl | CCN | CH | CH |
| I-106 | 3-(4-chlorophenyl)-3-fluoro-allyl | CCN | CH | CH |
| I-107 | 3-chloro-4-fluoro-cinnamyl | CCN | CH | CH |
| I-108 | 3,5-dichloro-cinnamyl | CCN | CH | CH |
| I-109 | 5-phenyl-penta-2,4-dienyl | CCN | CH | CH |
| I-110 | 4-isopropyloxycarbonylamino-cinnamyl | CCN | CH | CH |
| I-111 | 3-naphthalen-2-yl-allyl | CCN | CH | CH |
| I-112 | 3-(5-trifluoromethyl-pyridin-2-yl)-allyl | CCN | CH | CH |
| I-113 | 3-(5-chloro-pyridin-2-yl)-allyl | CCN | CH | CH |
| I-114 | 3-pyridin-4-yl-allyl | CCN | CH | CH |
| I-115 | 3-(2-Chloro-pyridin-4-yl)-allyl | CCN | CH | CH |
| I-116 | 4-chlorobenzyl | COMe | CH | CH |
| I-117 | Cinnamyl | COMe | CH | CH |
| I-118 | 4-chlorocinnamyl | COMe | CH | CH |
| I-119 | 4-fluorocinnamyl | COMe | CH | CH |
| I-120 | 4-bromocinnamyl | COMe | CH | CH |
| I-121 | 4-trifluoromethylcinnamyl | COMe | CH | CH |
| I-122 | 4-trifluoromethoxycinnamyl | COMe | CH | CH |
| I-123 | 4-pentafluoroethoxycinnamyl | COMe | CH | CH |
| I-124 | 4-methoxycinnamyl | COMe | CH | CH |
| I-125 | 4-ethoxycinnamyl | COMe | CH | CH |
| I-126 | 4-cyanocinnamyl | COMe | CH | CH |
| I-127 | 3-(6-chloro-pyridin-3-yl)-allyl | COMe | CH | CH |
| I-128 | 3-(4-chlorophenyl)-but-2-enyl | COMe | CH | CH |
| I-129 | 3-(4-chlorophenyl)-3-fluoro-allyl | COMe | CH | CH |
| I-130 | 3-chloro-4-fluoro-cinnamyl | COMe | CH | CH |
| I-131 | 3,5-dichloro-cinnamyl | COMe | CH | CH |

TABLE 1-continued

| Compound No | R$^8$ | C—R$^{4a}$ | C—R$^{4b}$ | C—R$^{4c}$ |
|---|---|---|---|---|
| I-132 | 5-phenyl-penta-2,4-dienyl | COMe | CH | CH |
| I-133 | 4-isopropyloxycarbonylamino-cinnamyl | COMe | CH | CH |
| I-134 | 3-naphthalen-2-yl-allyl | COMe | CH | CH |
| I-135 | 3-(5-trifluoromethyl-pyridin-2-yl)-allyl | COMe | CH | CH |
| I-136 | 3-(5-chloro-pyridin-2-yl)-allyl | COMe | CH | CH |
| I-137 | 3-pyridin-4-yl-allyl | COMe | CH | CH |
| I-138 | 3-(2-Chloro-pyridin-4-yl)-allyl | COMe | CH | CH |
| I-139 | 4-chlorobenzyl | COCF$_3$ | CH | CH |
| I-140 | Cinnamyl | COCF$_3$ | CH | CH |
| I-141 | 4-chlorocinnamyl | COCF$_3$ | CH | CH |
| I-142 | 4-fluorocinnamyl | COCF$_3$ | CH | CH |
| I-143 | 4-bromocinnamyl | COCF$_3$ | CH | CH |
| I-144 | 4-trifluoromethylcinnamyl | COCF$_3$ | CH | CH |
| I-145 | 4-trifluoromethoxycinnamyl | COCF$_3$ | CH | CH |
| I-146 | 4-pentafluoroethoxycinnamyl | COCF$_3$ | CH | CH |
| I-147 | 4-methoxycinnamyl | COCF$_3$ | CH | CH |
| I-148 | 4-ethoxycinnamyl | COCF$_3$ | CH | CH |
| I-149 | 4-cyanocinnamyl | COCF$_3$ | CH | CH |
| I-150 | 3-(6-chloro-pyridin-3-yl)-allyl | COCF$_3$ | CH | CH |
| I-151 | 3-(4-chlorophenyl)-but-2-enyl | COCF$_3$ | CH | CH |
| I-152 | 3-(4-chlorophenyl)-3-fluoro-allyl | COCF$_3$ | CH | CH |
| I-153 | 3-chloro-4-fluoro-cinnamyl | COCF$_3$ | CH | CH |
| I-154 | 3,5-dichloro-cinnamyl | COCF$_3$ | CH | CH |
| I-155 | 5-phenyl-penta-2,4-dienyl | COCF$_3$ | CH | CH |
| I-156 | 4-isopropyloxycarbonylamino-cinnamyl | COCF$_3$ | CH | CH |
| I-157 | 3-naphthalen-2-yl-allyl | COCF$_3$ | CH | CH |
| I-158 | 3-(5-trifluoromethyl-pyridin-2-yl)-allyl | COCF$_3$ | CH | CH |
| I-159 | 3-(5-chloro-pyridin-2-yl)-allyl | COCF$_3$ | CH | CH |
| I-160 | 3-pyridin-4-yl-allyl | COCF$_3$ | CH | CH |
| I-161 | 3-(2-Chloro-pyridin-4-yl)-allyl | COCF$_3$ | CH | CH |
| I-162 | 4-chlorobenzyl | CCH$_3$ | CH | CH |
| I-163 | Cinnamyl | CCH$_3$ | CH | CH |
| I-164 | 4-chlorocinnamyl | CCH$_3$ | CH | CH |
| I-165 | 4-fluorocinnamyl | CCH$_3$ | CH | CH |
| I-166 | 4-bromocinnamyl | CCH$_3$ | CH | CH |
| I-167 | 4-trifluoromethylcinnamyl | CCH$_3$ | CH | CH |
| I-168 | 4-trifluoromethoxycinnamyl | CCH$_3$ | CH | CH |
| I-169 | 4-pentafluoroethoxycinnamyl | CCH$_3$ | CH | CH |
| I-170 | 4-methoxycinnamyl | CCH$_3$ | CH | CH |
| I-171 | 4-ethoxycinnamyl | CCH$_3$ | CH | CH |
| I-172 | 4-cyanocinnamyl | CCH$_3$ | CH | CH |
| I-173 | 3-(6-chloro-pyridin-3-yl)-allyl | CCH$_3$ | CH | CH |
| I-174 | 3-(4-chlorophenyl)-but-2-enyl | CCH$_3$ | CH | CH |
| I-175 | 3-(4-chlorophenyl)-3-fluoro-allyl | CCH$_3$ | CH | CH |
| I-176 | 3-chloro-4-fluoro-cinnamyl | CCH$_3$ | CH | CH |
| I-177 | 3,5-dichloro-cinnamyl | CCH$_3$ | CH | CH |
| I-178 | 5-phenyl-penta-2,4-dienyl | CCH$_3$ | CH | CH |
| I-179 | 4-isopropyloxycarbonylamino-cinnamyl | CCH$_3$ | CH | CH |
| I-180 | 3-naphthalen-2-yl-allyl | CCH$_3$ | CH | CH |
| I-181 | 3-(5-trifluoromethyl-pyridin-2-yl)-allyl | CCH$_3$ | CH | CH |
| I-182 | 3-(5-chloro-pyridin-2-yl)-allyl | CCH$_3$ | CH | CH |
| I-183 | 3-pyridin-4-yl-allyl | CCH$_3$ | CH | CH |
| I-184 | 3-(2-Chloro-pyridin-4-yl)-allyl | CCH$_3$ | CH | CH |
| I-185 | 4-chlorobenzyl | CCF$_3$ | CH | CH |
| I-186 | Cinnamyl | CCF$_3$ | CH | CH |
| I-187 | 4-chlorocinnamyl | CCF$_3$ | CH | CH |
| I-188 | 4-fluorocinnamyl | CCF$_3$ | CH | CH |
| I-189 | 4-bromocinnamyl | CCF$_3$ | CH | CH |
| I-190 | 4-trifluoromethylcinnamyl | CCF$_3$ | CH | CH |
| I-191 | 4-trifluoromethoxycinnamyl | CCF$_3$ | CH | CH |
| I-192 | 4-pentafluoroethoxycinnamyl | CCF$_3$ | CH | CH |
| I-193 | 4-methoxycinnamyl | CCF$_3$ | CH | CH |
| I-194 | 4-ethoxycinnamyl | CCF$_3$ | CH | CH |
| I-195 | 4-cyanocinnamyl | CCF$_3$ | CH | CH |
| I-196 | 3-(6-chloro-pyridin-3-yl)-allyl | CCF$_3$ | CH | CH |
| I-197 | 3-(4-chlorophenyl)-but-2-enyl | CCF$_3$ | CH | CH |
| I-198 | 3-(4-chlorophenyl)-3-fluoro-allyl | CCF$_3$ | CH | CH |
| I-199 | 3-chloro-4-fluoro-cinnamyl | CCF$_3$ | CH | CH |
| I-200 | 3,5-dichloro-cinnamyl | CCF$_3$ | CH | CH |
| I-201 | 5-phenyl-penta-2,4-dienyl | CCF$_3$ | CH | CH |
| I-202 | 4-isopropyloxycarbonylamino-cinnamyl | CCF$_3$ | CH | CH |
| I-203 | 3-naphthalen-2-yl-allyl | CCF$_3$ | CH | CH |
| I-204 | 3-(5-trifluoromethyl-pyridin-2-yl)-allyl | CCF$_3$ | CH | CH |
| I-205 | 3-(5-chloro-pyridin-2-yl)-allyl | CCF$_3$ | CH | CH |
| I-206 | 3-pyridin-4-yl-allyl | CCF$_3$ | CH | CH |
| I-207 | 3-(2-Chloro-pyridin-4-yl)-allyl | CCF$_3$ | CH | CH |
| I-208 | 4-chlorobenzyl | CH | CCl | CH |
| I-209 | Cinnamyl | CH | CCl | CH |

TABLE 1-continued

| Compound No | R⁸ | C—R⁴ᵃ | C—R⁴ᵇ | C—R⁴ᶜ |
|---|---|---|---|---|
| I-210 | 4-chlorocinnamyl | CH | CCl | CH |
| I-211 | 4-fluorocinnamyl | CH | CCl | CH |
| I-212 | 4-bromocinnamyl | CH | CCl | CH |
| I-213 | 4-trifluoromethylcinnamyl | CH | CCl | CH |
| I-214 | 4-trifluoromethoxycinnamyl | CH | CCl | CH |
| I-215 | 4-pentafluoroethoxycinnamyl | CH | CCl | CH |
| I-216 | 4-methoxycinnamyl | CH | CCl | CH |
| I-217 | 4-ethoxycinnamyl | CH | CCl | CH |
| I-218 | 4-cyanocinnamyl | CH | CCl | CH |
| I-219 | 3-(6-chloro-pyridin-3-yl)-allyl | CH | CCl | CH |
| I-220 | 3-(4-chlorophenyl)-but-2-enyl | CH | CCl | CH |
| I-221 | 3-(4-chlorophenyl)-3-fluoro-allyl | CH | CCl | CH |
| I-222 | 3-chloro-4-fluoro-cinnamyl | CH | CCl | CH |
| I-223 | 3,5-dichloro-cinnamyl | CH | CCl | CH |
| I-224 | 5-phenyl-penta-2,4-dienyl | CH | CCl | CH |
| I-225 | 4-isopropyloxycarbonylamino-cinnamyl | CH | CCl | CH |
| I-226 | 3-naphthalen-2-yl-allyl | CH | CCl | CH |
| I-227 | 3-(5-trifluoromethyl-pyridin-2-yl)-allyl | CH | CCl | CH |
| I-228 | 3-(5-chloro-pyridin-2-yl)-allyl | CH | CCl | CH |
| I-229 | 3-pyridin-4-yl-allyl | CH | CCl | CH |
| I-230 | 3-(2-Chloro-pyridin-4-yl)-allyl | CH | CCl | CH |
| I-231 | 4-chlorobenzyl | CH | CF | CH |
| I-232 | Cinnamyl | CH | CF | CH |
| I-233 | 4-chlorocinnamyl | CH | CF | CH |
| I-234 | 4-fluorocinnamyl | CH | CF | CH |
| I-235 | 4-bromocinnamyl | CH | CF | CH |
| I-236 | 4-trifluoromethylcinnamyl | CH | CF | CH |
| I-237 | 4-trifluoromethoxycinnamyl | CH | CF | CH |
| I-238 | 4-pentafluoroethoxycinnamyl | CH | CF | CH |
| I-239 | 4-methoxycinnamyl | CH | CF | CH |
| I-240 | 4-ethoxycinnamyl | CH | CF | CH |
| I-241 | 4-cyanocinnamyl | CH | CF | CH |
| I-242 | 3-(6-chloro-pyridin-3-yl)-allyl | CH | CF | CH |
| I-243 | 3-(4-chlorophenyl)-but-2-enyl | CH | CF | CH |
| I-244 | 3-(4-chlorophenyl)-3-fluoro-allyl | CH | CF | CH |
| I-245 | 3-chloro-4-fluoro-cinnamyl | CH | CF | CH |
| I-246 | 3,5-dichloro-cinnamyl | CH | CF | CH |
| I-247 | 5-phenyl-penta-2,4-dienyl | CH | CF | CH |
| I-248 | 4-isopropyloxycarbonylamino-cinnamyl | CH | CF | CH |
| I-249 | 3-naphthalen-2-yl-allyl | CH | CF | CH |
| I-250 | 3-(5-trifluoromethyl-pyridin-2-yl)-allyl | CH | CF | CH |
| I-251 | 3-(5-chloro-pyridin-2-yl)-allyl | CH | CF | CH |
| I-252 | 3-pyridin-4-yl-allyl | CH | CF | CH |
| I-253 | 3-(2-Chloro-pyridin-4-yl)-allyl | CH | CF | CH |
| I-254 | 4-chlorobenzyl | CH | CBr | CH |
| I-255 | Cinnamyl | CH | CBr | CH |
| I-256 | 4-chlorocinnamyl | CH | CBr | CH |
| I-257 | 4-fluorocinnamyl | CH | CBr | CH |
| I-258 | 4-bromocinnamyl | CH | CBr | CH |
| I-259 | 4-trifluoromethylcinnamyl | CH | CBr | CH |
| I-260 | 4-trifluoromethoxycinnamyl | CH | CBr | CH |
| I-261 | 4-pentafluoroethoxycinnamyl | CH | CBr | CH |
| I-262 | 4-methoxycinnamyl | CH | CBr | CH |
| I-263 | 4-ethoxycinnamyl | CH | CBr | CH |
| I-264 | 4-cyanocinnamyl | CH | CBr | CH |
| I-265 | 3-(6-chloro-pyridin-3-yl)-allyl | CH | CBr | CH |
| I-266 | 3-(4-chlorophenyl)-but-2-enyl | CH | CBr | CH |
| I-267 | 3-(4-chlorophenyl)-3-fluoro-allyl | CH | CBr | CH |
| I-268 | 3-chloro-4-fluoro-cinnamyl | CH | CBr | CH |
| I-269 | 3,5-dichloro-cinnamyl | CH | CBr | CH |
| I-270 | 5-phenyl-penta-2,4-dienyl | CH | CBr | CH |
| I-271 | 4-isopropyloxycarbonylamino-cinnamyl | CH | CBr | CH |
| I-272 | 3-naphthalen-2-yl-allyl | CH | CBr | CH |
| I-273 | 3-(5-trifluoromethyl-pyridin-2-yl)-allyl | CH | CBr | CH |
| I-274 | 3-(5-chloro-pyridin-2-yl)-allyl | CH | CBr | CH |
| I-275 | 3-pyridin-4-yl-allyl | CH | CBr | CH |
| I-276 | 3-(2-Chloro-pyridin-4-yl)-allyl | CH | CBr | CH |
| I-277 | 4-chlorobenzyl | CH | COCF$_3$ | CH |
| I-278 | Cinnamyl | CH | COCF$_3$ | CH |
| I-279 | 4-chlorocinnamyl | CH | COCF$_3$ | CH |
| I-280 | 4-fluorocinnamyl | CH | COCF$_3$ | CH |
| I-281 | 4-bromocinnamyl | CH | COCF$_3$ | CH |
| I-282 | 4-trifluoromethylcinnamyl | CH | COCF$_3$ | CH |
| I-283 | 4-trifluoromethoxycinnamyl | CH | COCF$_3$ | CH |
| I-284 | 4-pentafluoroethoxycinnamyl | CH | COCF$_3$ | CH |
| I-285 | 4-methoxycinnamyl | CH | COCF$_3$ | CH |
| I-286 | 4-ethoxycinnamyl | CH | COCF$_3$ | CH |
| I-287 | 4-cyanocinnamyl | CH | COCF$_3$ | CH |

TABLE 1-continued

| Compound No | R[8] | C—R[4a] | C—R[4b] | C—R[4c] |
|---|---|---|---|---|
| I-288 | 3-(6-chloro-pyridin-3-yl)-allyl | CH | COCF$_3$ | CH |
| I-289 | 3-(4-chlorophenyl)-but-2-enyl | CH | COCF$_3$ | CH |
| I-290 | 3-(4-chlorophenyl)-3-fluoro-allyl | CH | COCF$_3$ | CH |
| I-291 | 3-chloro-4-fluoro-cinnamyl | CH | COCF$_3$ | CH |
| I-292 | 3,5-dichloro-cinnamyl | CH | COCF$_3$ | CH |
| I-293 | 5-phenyl-penta-2,4-dienyl | CH | COCF$_3$ | CH |
| I-294 | 4-isopropyloxycarbonylamino-cinnamyl | CH | COCF$_3$ | CH |
| I-295 | 3-naphthalen-2-yl-allyl | CH | COCF$_3$ | CH |
| I-296 | 3-(5-trifluoromethyl-pyridin-2-yl)-allyl | CH | COCF$_3$ | CH |
| I-297 | 3-(5-chloro-pyridin-2-yl)-allyl | CH | COCF$_3$ | CH |
| I-298 | 3-pyridin-4-yl-allyl | CH | COCF$_3$ | CH |
| I-299 | 3-(2-Chloro-pyridin-4-yl)-allyl | CH | COCF$_3$ | CH |
| I-300 | 4-chlorobenzyl | CH | CCH$_3$ | CH |
| I-301 | Cinnamyl | CH | CCH$_3$ | CH |
| I-302 | 4-chlorocinnamyl | CH | CCH$_3$ | CH |
| I-303 | 4-fluorocinnamyl | CH | CCH$_3$ | CH |
| I-304 | 4-bromocinnamyl | CH | CCH$_3$ | CH |
| I-305 | 4-trifluoromethylcinnamyl | CH | CCH$_3$ | CH |
| I-306 | 4-trifluoromethoxycinnamyl | CH | CCH$_3$ | CH |
| I-307 | 4-pentafluoroethoxycinnamyl | CH | CCH$_3$ | CH |
| I-308 | 4-methoxycinnamyl | CH | CCH$_3$ | CH |
| I-309 | 4-ethoxycinnamyl | CH | CCH$_3$ | CH |
| I-310 | 4-cyanocinnamyl | CH | CCH$_3$ | CH |
| I-311 | 3-(6-chloro-pyridin-3-yl)-allyl | CH | CCH$_3$ | CH |
| I-312 | 3-(4-chlorophenyl)-but-2-enyl | CH | CCH$_3$ | CH |
| I-313 | 3-(4-chlorophenyl)-3-fluoro-allyl | CH | CCH$_3$ | CH |
| I-314 | 3-chloro-4-fluoro-cinnamyl | CH | CCH$_3$ | CH |
| I-315 | 3,5-dichloro-cinnamyl | CH | CCH$_3$ | CH |
| I-316 | 5-phenyl-penta-2,4-dienyl | CH | CCH$_3$ | CH |
| I-317 | 4-isopropyloxycarbonylamino-cinnamyl | CH | CCH$_3$ | CH |
| I-318 | 3-naphthalen-2-yl-allyl | CH | CCH$_3$ | CH |
| I-319 | 3-(5-trifluoromethyl-pyridin-2-yl)-allyl | CH | CCH$_3$ | CH |
| I-320 | 3-(5-chloro-pyridin-2-yl)-allyl | CH | CCH$_3$ | CH |
| I-321 | 3-pyridin-4-yl-allyl | CH | CCH$_3$ | CH |
| I-322 | 3-(2-Chloro-pyridin-4-yl)-allyl | CH | CCH$_3$ | CH |
| I-323 | 4-chlorobenzyl | CH | CCF$_3$ | CH |
| I-324 | Cinnamyl | CH | CCF$_3$ | CH |
| I-325 | 4-chlorocinnamyl | CH | CCF$_3$ | CH |
| I-326 | 4-fluorocinnamyl | CH | CCF$_3$ | CH |
| I-327 | 4-bromocinnamyl | CH | CCF$_3$ | CH |
| I-328 | 4-trifluoromethylcinnamyl | CH | CCF$_3$ | CH |
| I-329 | 4-trifluoromethoxycinnamyl | CH | CCF$_3$ | CH |
| I-330 | 4-pentafluoroethoxycinnamyl | CH | CCF$_3$ | CH |
| I-331 | 4-methoxycinnamyl | CH | CCF$_3$ | CH |
| I-332 | 4-ethoxycinnamyl | CH | CCF$_3$ | CH |
| I-333 | 4-cyanocinnamyl | CH | CCF$_3$ | CH |
| I-334 | 3-(6-chloro-pyridin-3-yl)-allyl | CH | CCF$_3$ | CH |
| I-335 | 3-(4-chlorophenyl)-but-2-enyl | CH | CCF$_3$ | CH |
| I-336 | 3-(4-chlorophenyl)-3-fluoro-allyl | CH | CCF$_3$ | CH |
| I-337 | 3-chloro-4-fluoro-cinnamyl | CH | CCF$_3$ | CH |
| I-338 | 3,5-dichloro-cinnamyl | CH | CCF$_3$ | CH |
| I-339 | 5-phenyl-penta-2,4-dienyl | CH | CCF$_3$ | CH |
| I-340 | 4-isopropyloxycarbonylamino-cinnamyl | CH | CCF$_3$ | CH |
| I-341 | 3-naphthalen-2-yl-allyl | CH | CCF$_3$ | CH |
| I-342 | 3-(5-trifluoromethyl-pyridin-2-yl)-allyl | CH | CCF$_3$ | CH |
| I-343 | 3-(5-chloro-pyridin-2-yl)-allyl | CH | CCF$_3$ | CH |
| I-344 | 3-pyridin-4-yl-allyl | CH | CCF$_3$ | CH |
| I-345 | 3-(2-Chloro-pyridin-4-yl)-allyl | CH | CCF$_3$ | CH |
| I-346 | 4-chlorobenzyl | CH | CH | CF |
| I-347 | Cinnamyl | CH | CH | CF |
| I-348 | 4-chlorocinnamyl | CH | CH | CF |
| I-349 | 4-fluorocinnamyl | CH | CH | CF |
| I-350 | 4-bromocinnamyl | CH | CH | CF |
| I-351 | 4-trifluoromethylcinnamyl | CH | CH | CF |
| I-352 | 4-trifluoromethoxycinnamyl | CH | CH | CF |
| I-353 | 4-pentafluoroethoxycinnamyl | CH | CH | CF |
| I-354 | 4-methoxycinnamyl | CH | CH | CF |
| I-355 | 4-ethoxycinnamyl | CH | CH | CF |
| I-356 | 4-cyanocinnamyl | CH | CH | CF |
| I-357 | 3-(6-chloro-pyridin-3-yl)-allyl | CH | CH | CF |
| I-358 | 3-(4-chlorophenyl)-but-2-enyl | CH | CH | CF |
| I-359 | 3-(4-chlorophenyl)-3-fluoro-allyl | CH | CH | CF |
| I-360 | 3-chloro-4-fluoro-cinnamyl | CH | CH | CF |
| I-361 | 3,5-dichloro-cinnamyl | CH | CH | CF |
| I-362 | 5-phenyl-penta-2,4-dienyl | CH | CH | CF |
| I-363 | 4-isopropyloxycarbonylamino-cinnamyl | CH | CH | CF |
| I-364 | 3-naphthalen-2-yl-allyl | CH | CH | CF |
| I-365 | 3-(5-trifluoromethyl-pyridin-2-yl)-allyl | CH | CH | CF |

TABLE 1-continued

| Compound No | $R^8$ | $C-R^{4a}$ | $C-R^{4b}$ | $C-R^{4c}$ |
|---|---|---|---|---|
| I-366 | 3-(5-chloro-pyridin-2-yl)-allyl | CH | CH | CF |
| I-367 | 3-pyridin-4-yl-allyl | CH | CH | CF |
| I-368 | 3-(2-Chloro-pyridin-4-yl)-allyl | CH | CH | CF |
| I-369 | 4-chlorobenzyl | CH | CH | CCl |
| I-370 | Cinnamyl | CH | CH | CCl |
| I-371 | 4-chlorocinnamyl | CH | CH | CCl |
| I-372 | 4-fluorocinnamyl | CH | CH | CCl |
| I-373 | 4-bromocinnamyl | CH | CH | CCl |
| I-374 | 4-trifluoromethylcinnamyl | CH | CH | CCl |
| I-375 | 4-trifluoromethoxycinnamyl | CH | CH | CCl |
| I-376 | 4-pentafluoroethoxycinnamyl | CH | CH | CCl |
| I-377 | 4-methoxycinnamyl | CH | CH | CCl |
| I-378 | 4-ethoxycinnamyl | CH | CH | CCl |
| I-379 | 4-cyanocinnamyl | CH | CH | CCl |
| I-380 | 3-(6-chloro-pyridin-3-yl)-allyl | CH | CH | CCl |
| I-381 | 3-(4-chlorophenyl)-but-2-enyl | CH | CH | CCl |
| I-382 | 3-(4-chlorophenyl)-3-fluoro-allyl | CH | CH | CCl |
| I-383 | 3-chloro-4-fluoro-cinnamyl | CH | CH | CCl |
| I-384 | 3,5-dichloro-cinnamyl | CH | CH | CCl |
| I-385 | 5-phenyl-penta-2,4-dienyl | CH | CH | CCl |
| I-386 | 4-isopropyloxycarbonylamino-cinnamyl | CH | CH | CCl |
| I-387 | 3-naphthalen-2-yl-allyl | CH | CH | CCl |
| I-388 | 3-(5-trifluoromethyl-pyridin-2-yl)-allyl | CH | CH | CCl |
| I-389 | 3-(5-chloro-pyridin-2-yl)-allyl | CH | CH | CCl |
| I-390 | 3-pyridin-4-yl-allyl | CH | CH | CCl |
| I-391 | 3-(2-Chloro-pyridin-4-yl)-allyl | CH | CH | CCl |
| I-438 | 4-chlorobenzyl | CCl | CH | CCl |
| I-439 | Cinnamyl | CCl | CH | CCl |
| I-440 | 4-chlorocinnamyl | CCl | CH | CCl |
| I-441 | 4-fluorocinnamyl | CCl | CH | CCl |
| I-442 | 4-bromocinnamyl | CCl | CH | CCl |
| I-443 | 4-trifluoromethylcinnamyl | CCl | CH | CCl |
| I-444 | 4-trifluoromethoxycinnamyl | CCl | CH | CCl |
| I-445 | 4-pentafluoroethoxycinnamyl | CCl | CH | CCl |
| I-446 | 4-methoxycinnamyl | CCl | CH | CCl |
| I-447 | 4-ethoxycinnamyl | CCl | CH | CCl |
| I-448 | 4-cyanocinnamyl | CCl | CH | CCl |
| I-449 | 3-(6-chloro-pyridin-3-yl)-allyl | CCl | CH | CCl |
| I-450 | 3-(4-chlorophenyl)-but-2-enyl | CCl | CH | CCl |
| I-451 | 3-(4-chlorophenyl)-3-fluoro-allyl | CCl | CH | CCl |
| I-452 | 3-chloro-4-fluoro-cinnamyl | CCl | CH | CCl |
| I-453 | 3,5-dichloro-cinnamyl | CCl | CH | CCl |
| I-454 | 5-phenyl-penta-2,4-dienyl | CCl | CH | CCl |
| I-455 | 4-isopropyloxycarbonylamino-cinnamyl | CCl | CH | CCl |
| I-456 | 3-naphthalen-2-yl-allyl | CCl | CH | CCl |
| I-457 | 3-(5-trifluoromethyl-pyridin-2-yl)-allyl | CCl | CH | CCl |
| I-458 | 3-(5-chloro-pyridin-2-yl)-allyl | CCl | CH | CCl |
| I-459 | 3-pyridin-4-yl-allyl | CCl | CH | CCl |
| I-460 | 3-(2-Chloro-pyridin-4-yl)-allyl | CCl | CH | CCl |
| I-461 | 4-chlorobenzyl | CF | CH | CF |
| I-462 | Cinnamyl | CF | CH | CF |
| I-463 | 4-chlorocinnamyl | CF | CH | CF |
| I-464 | 4-fluorocinnamyl | CF | CH | CF |
| I-465 | 4-bromocinnamyl | CF | CH | CF |
| I-466 | 4-trifluoromethylcinnamyl | CF | CH | CF |
| I-467 | 4-trifluoromethoxycinnamyl | CF | CH | CF |
| I-468 | 4-pentafluoroethoxycinnamyl | CF | CH | CF |
| I-469 | 4-methoxycinnamyl | CF | CH | CF |
| I-470 | 4-ethoxycinnamyl | CF | CH | CF |
| I-471 | 4-cyanocinnamyl | CF | CH | CF |
| I-472 | 3-(6-chloro-pyridin-3-yl)-allyl | CF | CH | CF |
| I-473 | 3-(4-chlorophenyl)-but-2-enyl | CF | CH | CF |
| I-474 | 3-(4-chlorophenyl)-3-fluoro-allyl | CF | CH | CF |
| I-475 | 3-chloro-4-fluoro-cinnamyl | CF | CH | CF |
| I-476 | 3,5-dichloro-cinnamyl | CF | CH | CF |
| I-477 | 5-phenyl-penta-2,4-dienyl | CF | CH | CF |
| I-478 | 4-isopropyloxycarbonylamino-cinnamyl | CF | CH | CF |
| I-479 | 3-naphthalen-2-yl-allyl | CF | CH | CF |
| I-480 | 3-(5-trifluoromethyl-pyridin-2-yl)-allyl | CF | CH | CF |
| I-481 | 3-(5-chloro-pyridin-2-yl)-allyl | CF | CH | CF |
| I-482 | 3-pyridin-4-yl-allyl | CF | CH | CF |
| I-483 | 3-(2-Chloro-pyridin-4-yl)-allyl | CF | CH | CF |
| I-484 | 4-chlorobenzyl | CF | CF | CH |
| I-485 | Cinnamyl | CF | CF | CH |
| I-486 | 4-chlorocinnamyl | CF | CF | CH |
| I-487 | 4-fluorocinnamyl | CF | CF | CH |
| I-488 | 4-bromocinnamyl | CF | CF | CH |
| I-489 | 4-trifluoromethylcinnamyl | CF | CF | CH |

TABLE 1-continued

| Compound No | R⁸ | C—R⁴ᵃ | C—R⁴ᵇ | C—R⁴ᶜ |
|---|---|---|---|---|
| I-490 | 4-trifluoromethoxycinnamyl | CF | CF | CH |
| I-491 | 4-pentafluoroethoxycinnamyl | CF | CF | CH |
| I-492 | 4-methoxycinnamyl | CF | CF | CH |
| I-493 | 4-ethoxycinnamyl | CF | CF | CH |
| I-494 | 4-cyanocinnamyl | CF | CF | CH |
| I-495 | 3-(6-chloro-pyridin-3-yl)-allyl | CF | CF | CH |
| I-496 | 3-(4-chlorophenyl)-but-2-enyl | CF | CF | CH |
| I-497 | 3-(4-chlorophenyl)-3-fluoro-allyl | CF | CF | CH |
| I-498 | 3-chloro-4-fluoro-cinnamyl | CF | CF | CH |
| I-499 | 3,5-dichloro-cinnamyl | CF | CF | CH |
| I-500 | 5-phenyl-penta-2,4-dienyl | CF | CF | CH |
| I-501 | 4-isopropyloxycarbonylamino-cinnamyl | CF | CF | CH |
| I-502 | 3-naphthalen-2-yl-allyl | CF | CF | CH |
| I-503 | 3-(5-trifluoromethyl-pyridin-2-yl)-allyl | CF | CF | CH |
| I-504 | 3-(5-chloro-pyridin-2-yl)-allyl | CF | CF | CH |
| I-505 | 3-pyridin-4-yl-allyl | CF | CF | CH |
| I-506 | 3-(2-Chloro-pyridin-4-yl)-allyl | CF | CF | CH |
| I-507 | 4-chlorobenzyl | CF | CCl | CH |
| I-508 | Cinnamyl | CF | CCl | CH |
| I-509 | 4-chlorocinnamyl | CF | CCl | CH |
| I-510 | 4-fluorocinnamyl | CF | CCl | CH |
| I-511 | 4-bromocinnamyl | CF | CCl | CH |
| I-512 | 4-trifluoromethylcinnamyl | CF | CCl | CH |
| I-513 | 4-trifluoromethoxycinnamyl | CF | CCl | CH |
| I-514 | 4-pentafluoroethoxycinnamyl | CF | CCl | CH |
| I-515 | 4-methoxycinnamyl | CF | CCl | CH |
| I-516 | 4-ethoxycinnamyl | CF | CCl | CH |
| I-517 | 4-cyanocinnamyl | CF | CCl | CH |
| I-518 | 3-(6-chloro-pyridin-3-yl)-allyl | CF | CCl | CH |
| I-519 | 3-(4-chlorophenyl)-but-2-enyl | CF | CCl | CH |
| I-520 | 3-(4-chlorophenyl)-3-fluoro-allyl | CF | CCl | CH |
| I-521 | 3-chloro-4-fluoro-cinnamyl | CF | CCl | CH |
| I-522 | 3,5-dichloro-cinnamyl | CF | CCl | CH |
| I-523 | 5-phenyl-penta-2,4-dienyl | CF | CCl | CH |
| I-524 | 4-isopropyloxycarbonylamino-cinnamyl | CF | CCl | CH |
| I-525 | 3-naphthalen-2-yl-allyl | CF | CCl | CH |
| I-526 | 3-(5-trifluoromethyl-pyridin-2-yl)-allyl | CF | CCl | CH |
| I-527 | 3-(5-chloro-pyridin-2-yl)-allyl | CF | CCl | CH |
| I-528 | 3-pyridin-4-yl-allyl | CF | CCl | CH |
| I-529 | 3-(2-Chloro-pyridin-4-yl)-allyl | CF | CCl | CH |
| I-530 | 4-chlorobenzyl | CCl | CF | CH |
| I-531 | Cinnamyl | CCl | CF | CH |
| I-532 | 4-chlorocinnamyl | CCl | CF | CH |
| I-533 | 4-fluorocinnamyl | CCl | CF | CH |
| I-534 | 4-bromocinnamyl | CCl | CF | CH |
| I-535 | 4-trifluoromethylcinnamyl | CCl | CF | CH |
| I-536 | 4-trifluoromethoxycinnamyl | CCl | CF | CH |
| I-537 | 4-pentafluoroethoxycinnamyl | CCl | CF | CH |
| I-538 | 4-methoxycinnamyl | CCl | CF | CH |
| I-539 | 4-ethoxycinnamyl | CCl | CF | CH |
| I-540 | 4-cyanocinnamyl | CCl | CF | CH |
| I-541 | 3-(6-chloro-pyridin-3-yl)-allyl | CCl | CF | CH |
| I-542 | 3-(4-chlorophenyl)-but-2-enyl | CCl | CF | CH |
| I-543 | 3-(4-chlorophenyl)-3-fluoro-allyl | CCl | CF | CH |
| I-544 | 3-chloro-4-fluoro-cinnamyl | CCl | CF | CH |
| I-545 | 3,5-dichloro-cinnamyl | CCl | CF | CH |
| I-546 | 5-phenyl-penta-2,4-dienyl | CCl | CF | CH |
| I-547 | 4-isopropyloxycarbonylamino-cinnamyl | CCl | CF | CH |
| I-548 | 3-naphthalen-2-yl-allyl | CCl | CF | CH |
| I-549 | 3-(5-trifluoromethyl-pyridin-2-yl)-allyl | CCl | CF | CH |
| I-550 | 3-(5-chloro-pyridin-2-yl)-allyl | CCl | CF | CH |
| I-551 | 3-pyridin-4-yl-allyl | CCl | CF | CH |
| I-552 | 3-(2-Chloro-pyridin-4-yl)-allyl | CCl | CF | CH |
| I-553 | 4-chlorobenzyl | CCl | CCl | CH |
| I-554 | Cinnamyl | CCl | CCl | CH |
| I-555 | 4-chlorocinnamyl | CCl | CCl | CH |
| I-556 | 4-fluorocinnamyl | CCl | CCl | CH |
| I-557 | 4-bromocinnamyl | CCl | CCl | CH |
| I-558 | 4-trifluoromethylcinnamyl | CCl | CCl | CH |
| I-559 | 4-trifluoromethoxycinnamyl | CCl | CCl | CH |
| I-560 | 4-pentafluoroethoxycinnamyl | CCl | CCl | CH |
| I-561 | 4-methoxycinnamyl | CCl | CCl | CH |
| I-562 | 4-ethoxycinnamyl | CCl | CCl | CH |
| I-563 | 4-cyanocinnamyl | CCl | CCl | CH |
| I-564 | 3-(6-chloro-pyridin-3-yl)-allyl | CCl | CCl | CH |
| I-565 | 3-(4-chlorophenyl)-but-2-enyl | CCl | CCl | CH |
| I-566 | 3-(4-chlorophenyl)-3-fluoro-allyl | CCl | CCl | CH |
| I-567 | 3-chloro-4-fluoro-cinnamyl | CCl | CCl | CH |

TABLE 1-continued

| Compound No | R8 | C—R4a | C—R4b | C—R4c |
|---|---|---|---|---|
| I-568 | 3,5-dichloro-cinnamyl | CCl | CCl | CH |
| I-569 | 5-phenyl-penta-2,4-dienyl | CCl | CCl | CH |
| I-570 | 4-isopropyloxycarbonylamino-cinnamyl | CCl | CCl | CH |
| I-571 | 3-naphthalen-2-yl-allyl | CCl | CCl | CH |
| I-572 | 3-(5-trifluoromethyl-pyridin-2-yl)-allyl | CCl | CCl | CH |
| I-573 | 3-(5-chloro-pyridin-2-yl)-allyl | CCl | CCl | CH |
| I-574 | 3-pyridin-4-yl-allyl | CCl | CCl | CH |
| I-575 | 3-(2-Chloro-pyridin-4-yl)-allyl | CCl | CCl | CH |

Table II provides 575 compounds of formula Ib

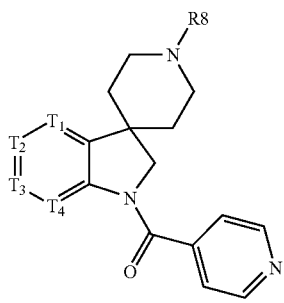

(Ib)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table III provides 575 compounds of formula Ic

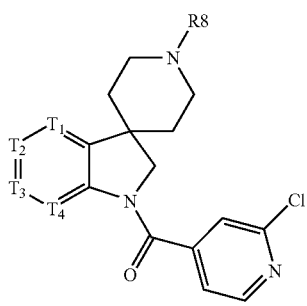

(Ic)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table IV provides 575 compounds of formula Id

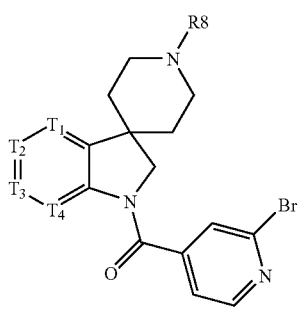

(Id)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table V provides 575 compounds of formula Ie

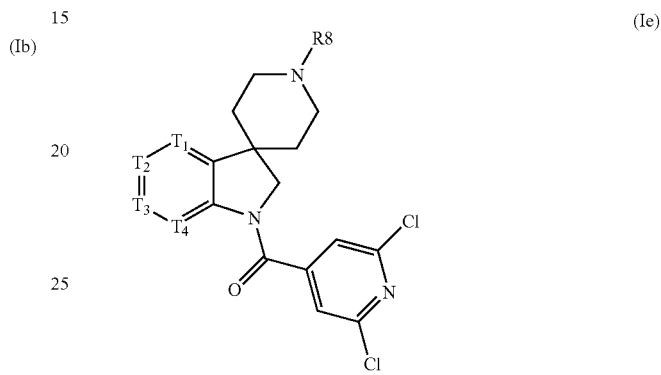

(Ie)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table VI provides 575 compounds of formula If

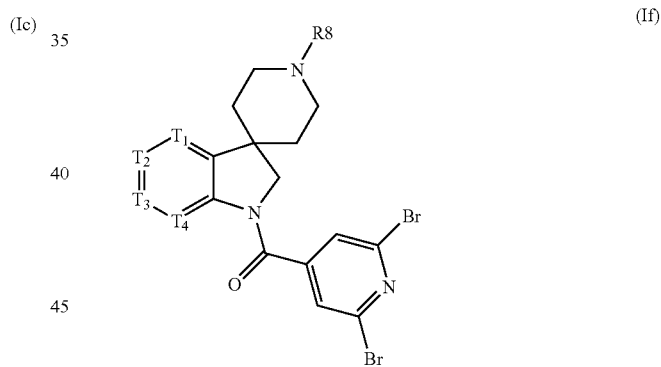

(If)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table VII provides 575 compounds of formula Ig

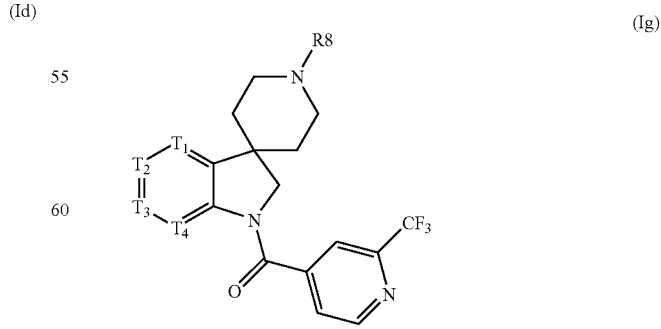

(Ig)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table VIII provides 575 compounds of formula Ih

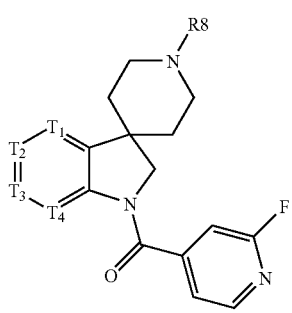
(Ih)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table IX provides 575 compounds of formula Ii

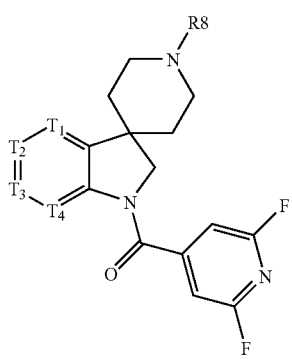
(Ii)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table X provides 575 compounds of formula Ij

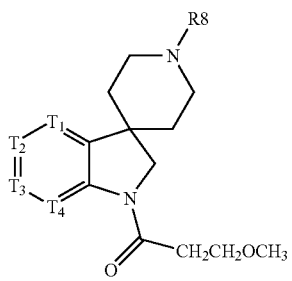
(Ij)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XI provides 575 compounds of formula Ik

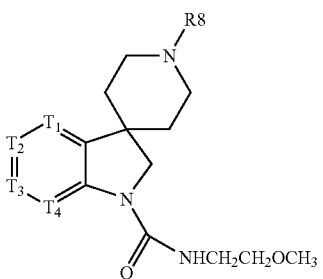
(Ik)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XII provides 575 compounds of formula Il

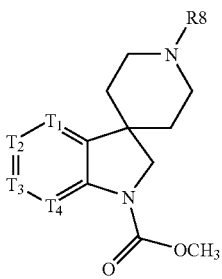
(Il)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XIII provides 575 compounds of formula Im

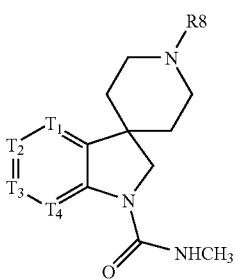
(Im)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XIV provides 575 compounds of formula In

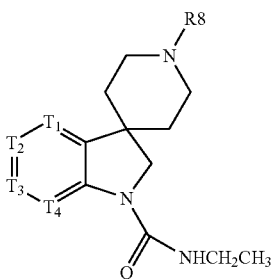
(In)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XV provides 575 compounds of formula Io

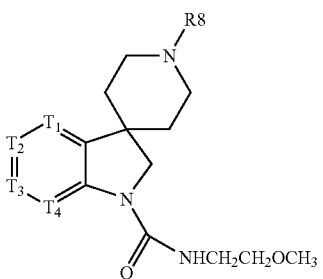
(Io)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XVI provides 575 compounds of formula Ip

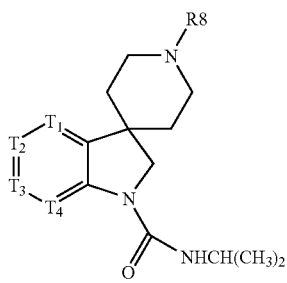
(Ip)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table XVII provides 575 compounds of formula Iq

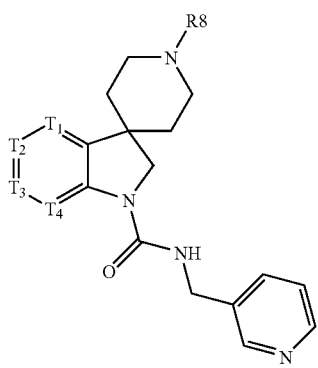
(Iq)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table XVIII provides 575 compounds of formula Ir

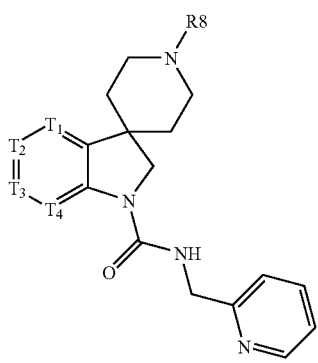
(Ir)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table XIX provides 575 compounds of formula Is

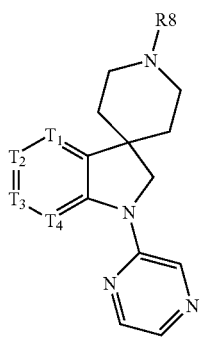
(Is)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table XX provides 575 compounds of formula It

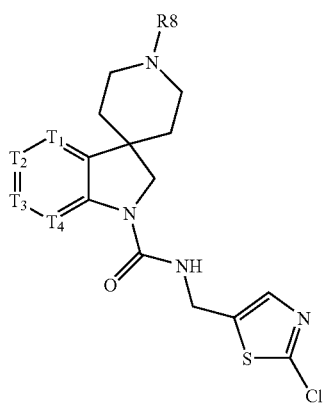
(It)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table XXI provides 575 compounds of formula Iu

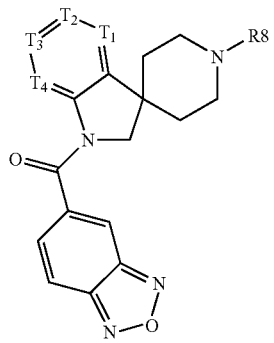
(Iu)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table XXII provides 575 compounds of formula Iv

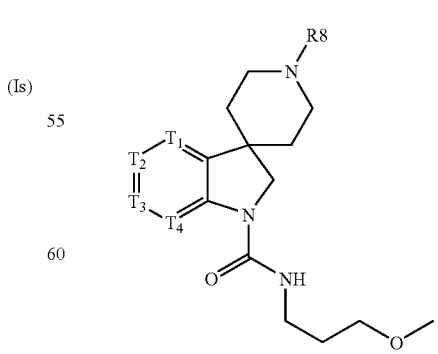
(Iv)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table XXIII provides 575 compounds of formula Iw

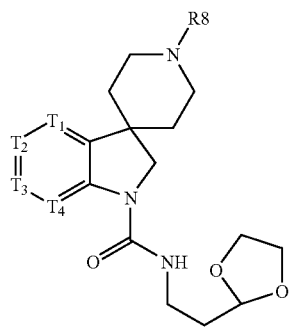
(Iw)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXIV provides 575 compounds of formula Ix

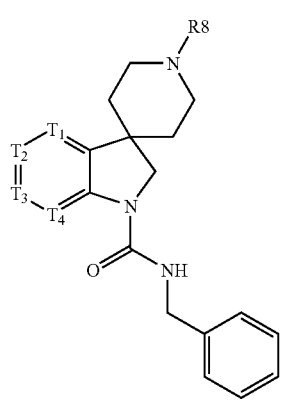
(Ix)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXV provides 575 compounds of formula Iy

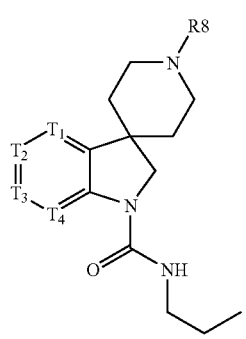
(Iy)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXVI provides 575 compounds of formula Iz

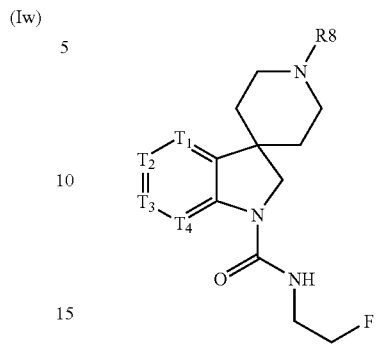
(Iz)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXVII provides 575 compounds of formula Iaa

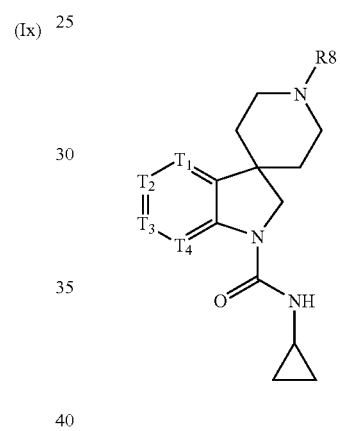
(Iaa)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXVIII provides 575 compounds of formula Iab

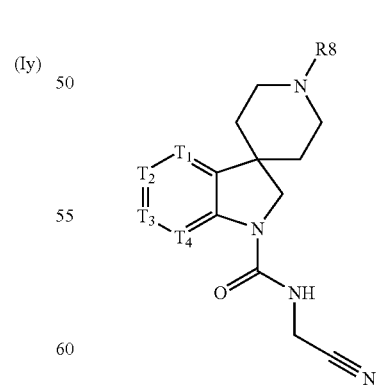
(Iab)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXIX provides 575 compounds of formula Iac

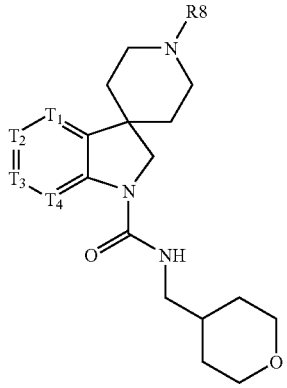

(Iac)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXX provides 575 compounds of formula Iad

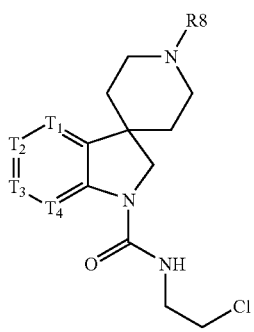

(Iad)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXXI provides 575 compounds of formula Iae

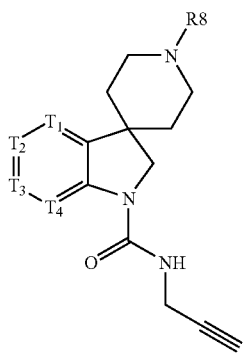

(Iae)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXXII provides 575 compounds of formula Iaf

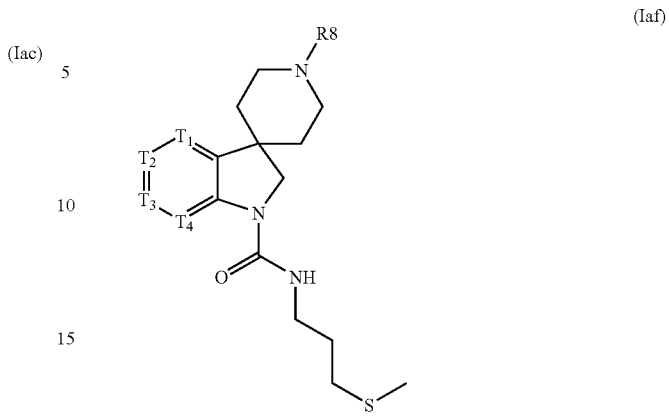

(Iaf)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXXIII provides 575 compounds of formula Iag

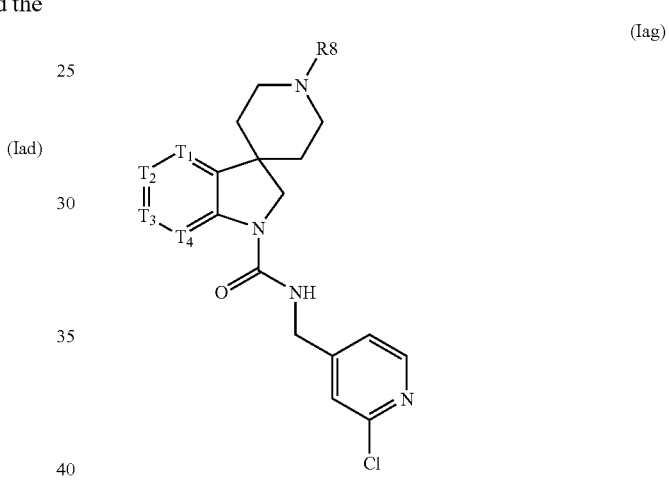

(Iag)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXXIV provides 575 compounds of formula Iah

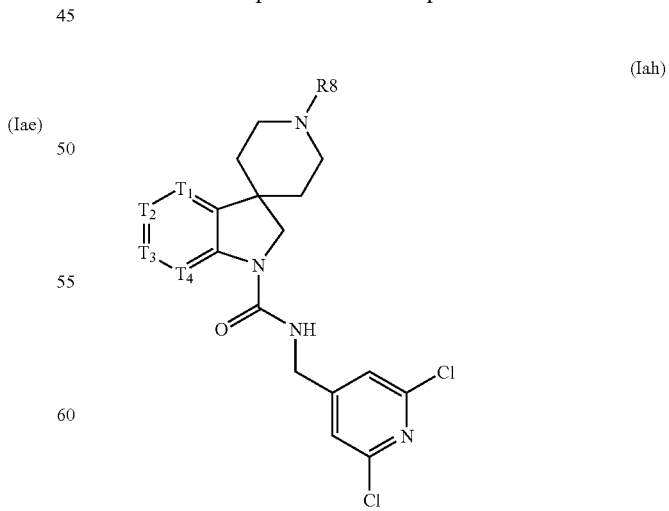

(Iah)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXXV provides 575 compounds of formula Iai

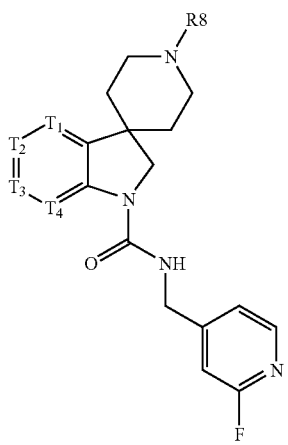

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXXVI provides 575 compounds of formula Iaj

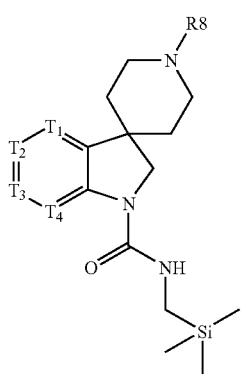

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXXVII provides 575 compounds of formula Iak

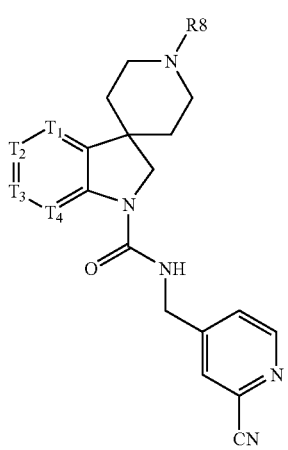

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXXVIII provides 575 compounds of formula Ial

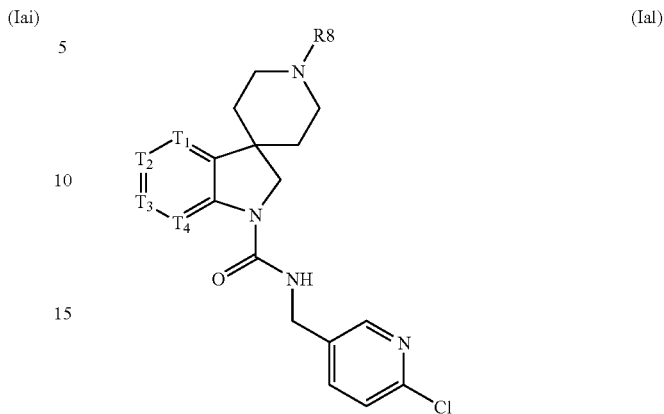

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XXXIX provides 575 compounds of formula Iam

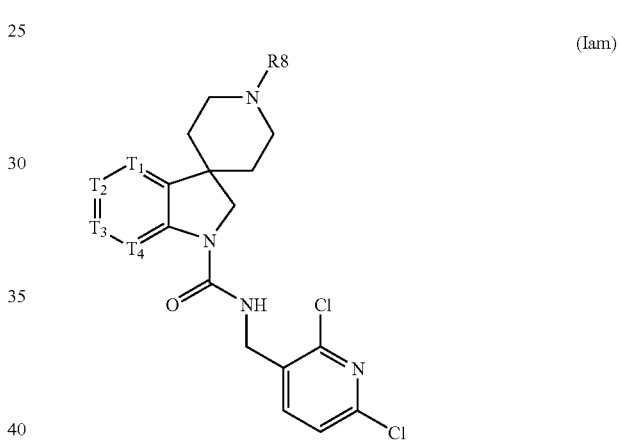

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XLX provides 575 compounds of formula Ian

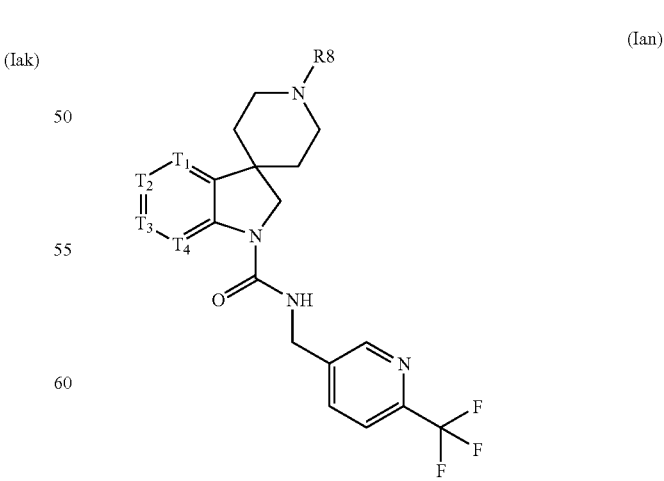

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XLI provides 575 compounds of formula Iao

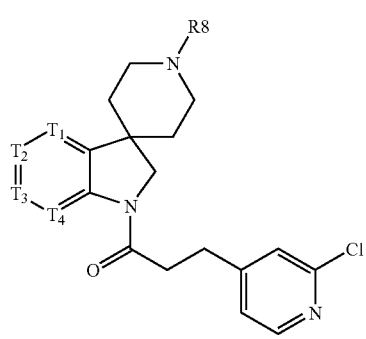

(Iao)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XLII provides 575 compounds of formula Iap

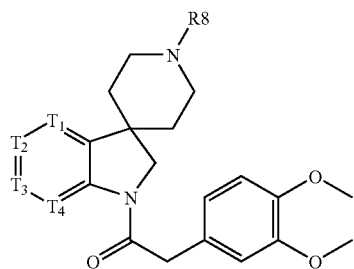

(Iap)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XLIII provides 575 compounds of formula Iaq

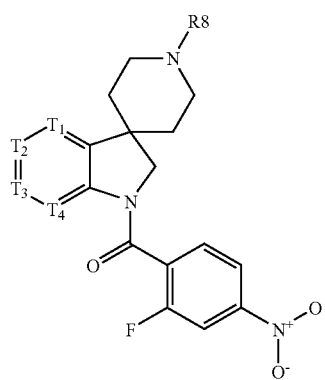

(Iaq)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XLIV provides 575 compounds of formula Iar

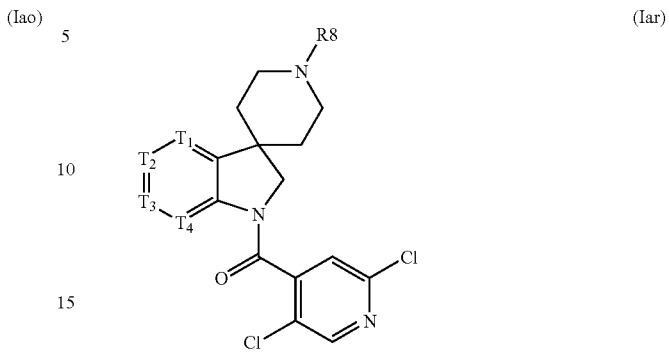

(Iar)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XLV provides 575 compounds of formula Ias

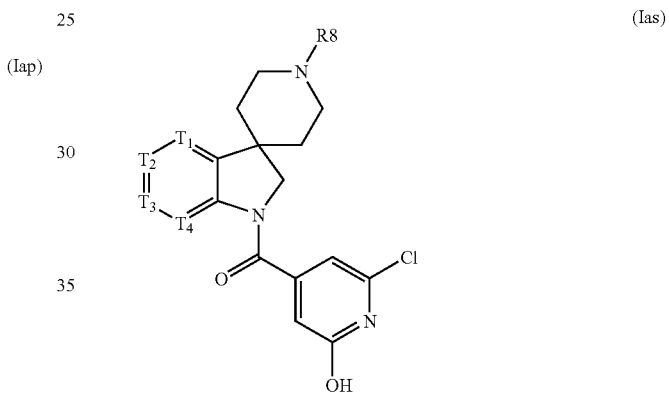

(Ias)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XLV provides 575 compounds of formula Iat

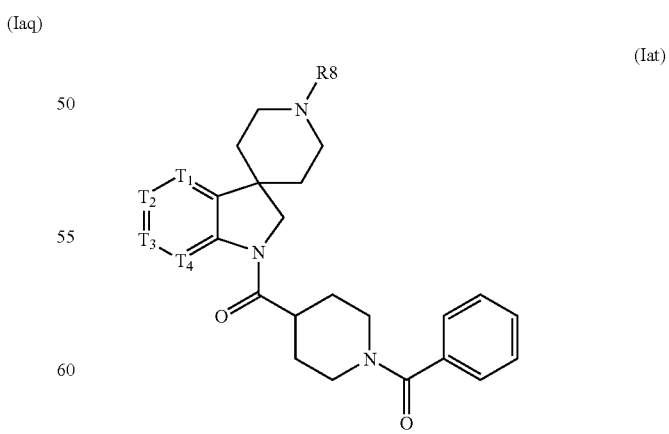

(Iat)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XLVII provides 575 compounds of formula Iau

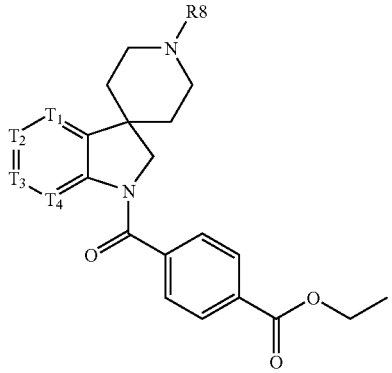

(Iau)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table XLVIII provides 575 compounds of formula Iav

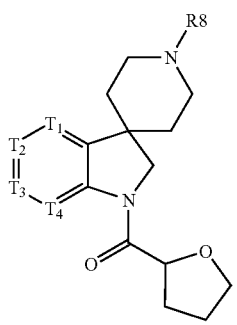

(Iav)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table IL provides 575 compounds of formula Iaw

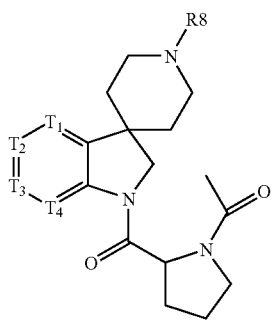

(Iaw)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table L provides 575 compounds of formula Iax

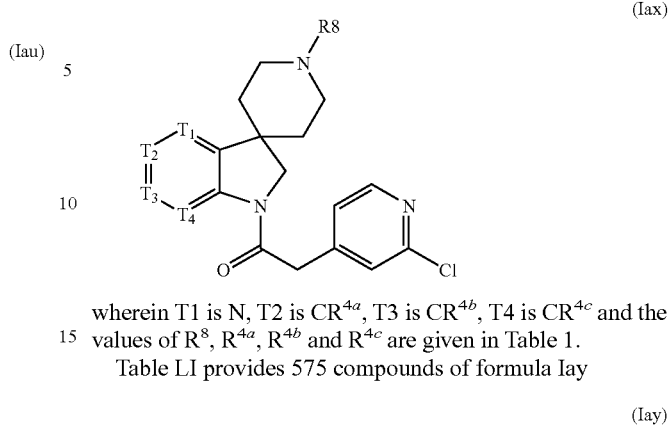

(Iax)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table LI provides 575 compounds of formula Iay

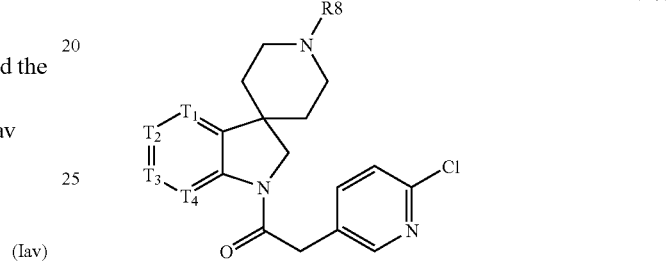

(Iay)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table LII provides 575 compounds of formula Iaz

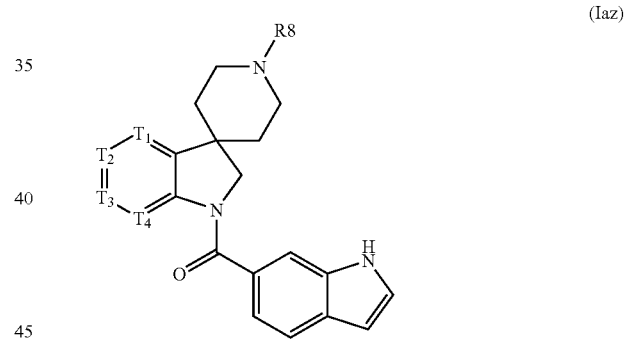

(Iaz)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table LIII provides 575 compounds of formula Iba

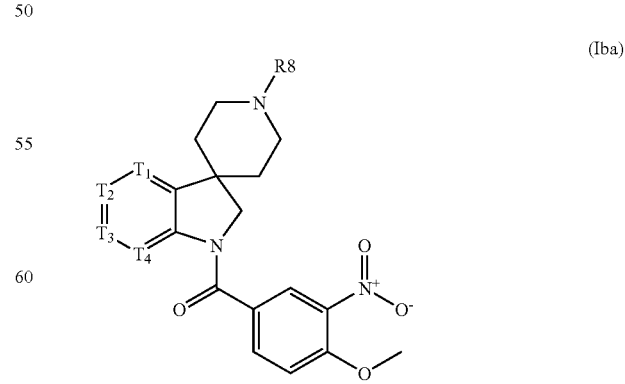

(Iba)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table LIV provides 575 compounds of formula Ibb

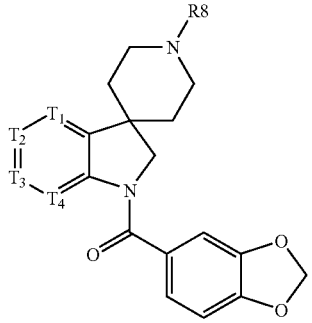
(Ibb)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table LV provides 575 compounds of formula Ibc

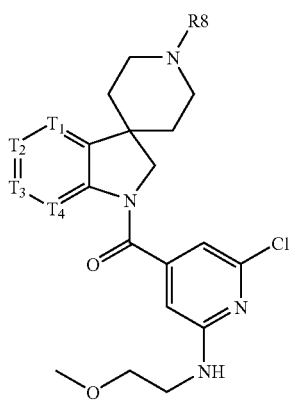
(Ibc)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table LVI provides 575 compounds of formula Ibd

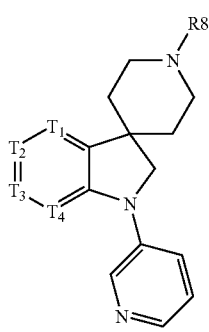
(Ibd)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table LVII provides 575 compounds of formula Ibe

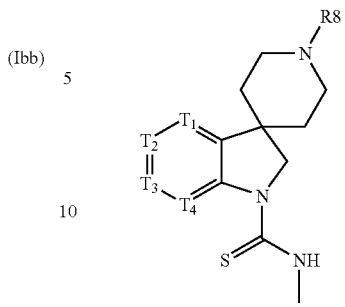
(Ibe)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table LVIII provides 575 compounds of formula Ibf

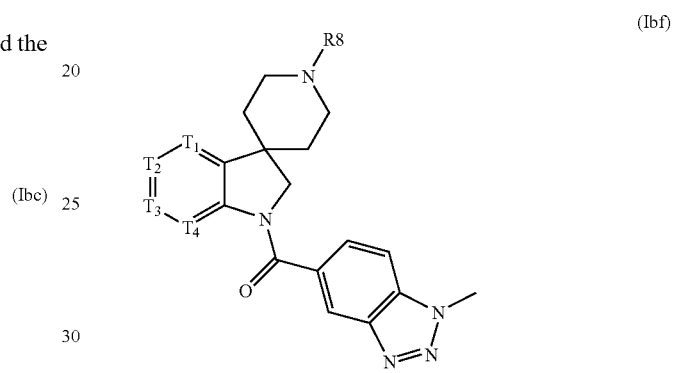
(Ibf)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table LIX provides 575 compounds of formula Ibg

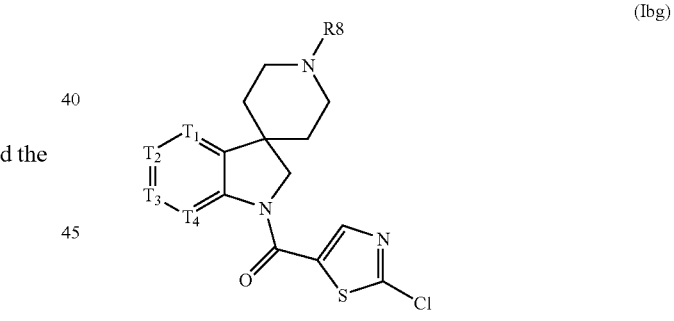
(Ibg)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table LX provides 575 compounds of formula Ibh

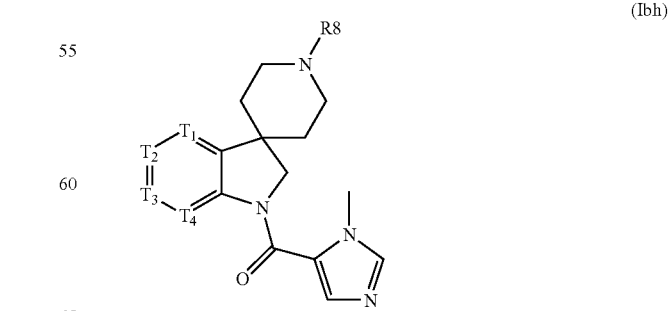
(Ibh)

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table LXI provides 575 compounds of formula Ibi

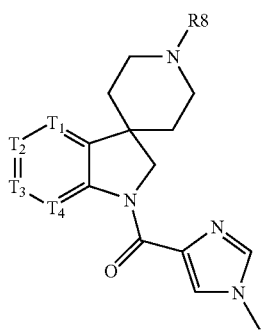
(Ibi)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table LXII provides 575 compounds of formula Ibj

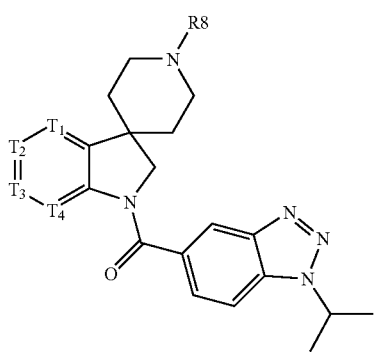
(Ibj)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table LXIII provides 575 compounds of formula Ibk

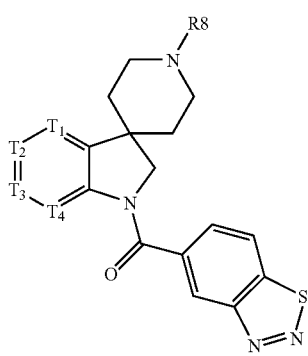
(Ibk)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table LXIV provides 575 compounds of formula Ibl

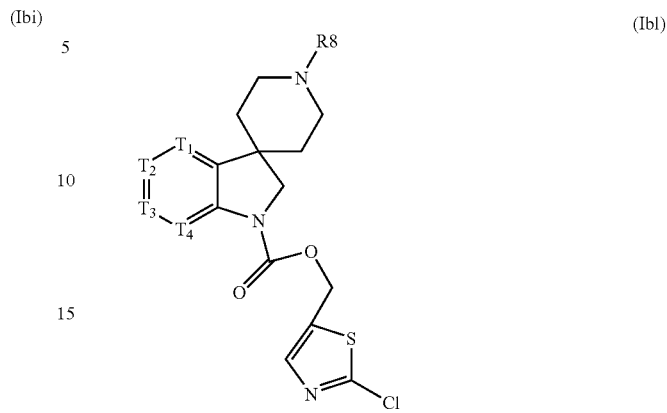
(Ibl)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table LXV provides 575 compounds of formula Ibm

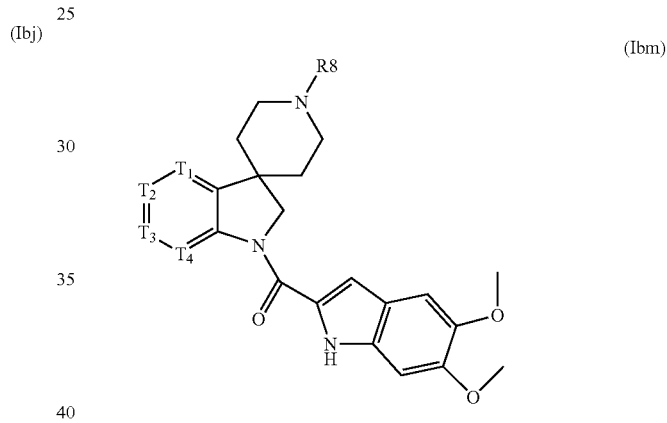
(Ibm)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table LXVI provides 575 compounds of formula Ibn

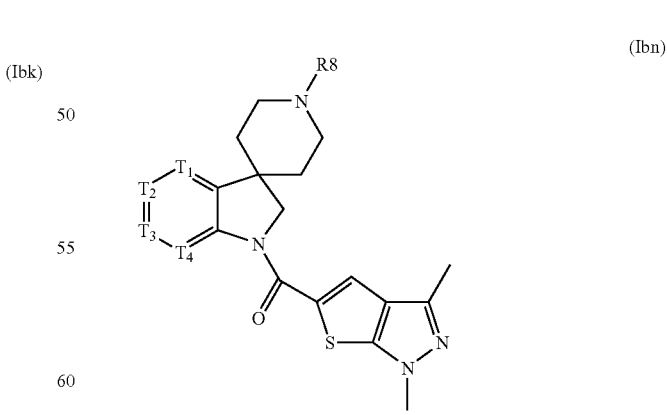
(Ibn)

wherein T1 is N, T2 is $CR^{4a}$, T3 is $CR^{4b}$, T4 is $CR^{4c}$ and the values of $R^8$, $R^{4a}$, $R^{4b}$ and $R^{4c}$ are given in Table 1.

Table LXVII provides 575 compounds of formula Ibo $$\text{(Ibo)}$$

wherein T1 is N, T2 is CR$^{4a}$, T3 is CR$^{4b}$, T4 is CR$^{4c}$ and the values of R$^8$, R$^{4a}$, R$^{4b}$ and R$^{4c}$ are given in Table 1.

Table CI provides 575 compounds of formula Ia wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CII provides 575 compounds of formula Ib wherein T1 is CR$^{4b}$, T2 is N, T3 is CR$^{4a}$, T4 is CR$^{4C}$ and the values of R$^8$, R$^{4a}$, R$^{4b}$ and R$^{4c}$ are given in Table 1.

Table CIII provides 575 compounds of formula Ic wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CIV provides 575 compounds of formula Id wherein T1 is CR$^{4b}$, T2 is N, T3 is CR$^{4a}$, T4 is CR$^{4C}$ and the values of R$^8$, R$^{4a}$, R$^{4b}$ and R$^{4c}$ are given in Table 1.

Table CV provides 575 compounds of formula Ie wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CVI provides 575 compounds of formula If wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CVII provides 575 compounds of formula Ig wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CVIII provides 575 compounds of formula Ih wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CIX provides 575 compounds of formula Ii wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CX provides 575 compounds of formula Ij wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXI provides 575 compounds of formula Ik wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXII provides 575 compounds of formula Il wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXIII provides 575 compounds of formula Im wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXIV provides 575 compounds of formula In wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXV provides 575 compounds of formula Io wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXVI provides 575 compounds of formula Ip wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXVII provides 575 compounds of formula Iq wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXVIII provides 575 compounds of formula Ir wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXIX provides 575 compounds of formula Is wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXX provides 575 compounds of formula It wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXI provides 575 compounds of formula Iu wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXII provides 575 compounds of formula Iv wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXIII provides 575 compounds of formula Iw wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXIV provides 575 compounds of formula Ix wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXV provides 575 compounds of formula Iy wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXVI provides 575 compounds of formula Iz wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXVII provides 575 compounds of formula Iaa wherein T1 is CR$^{4b}$, T2 is N, T3 is CR$^{4a}$, T4 is CR and the values of R$^8$, R$^{4a}$, R$^{4b}$ and R$^{4c}$ are given in Table 1.

Table CXXVIII provides 575 compounds of formula Iab wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXIX provides 575 compounds of formula Iac wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXX provides 575 compounds of formula Iad wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXXI provides 575 compounds of formula Iae wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXXII provides 575 compounds of formula Iaf wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXXIII provides 575 compounds of formula Iag wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXXIV provides 575 compounds of formula Iah wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXXV provides 575 compounds of formula Iai wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXXVI provides 575 compounds of formula Iaj wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXXVII provides 575 compounds of formula Iak wherein T1 is CR$^{4b}$, T2 is N, T3 is CR$^{4a}$, T4 is CR$^{4c}$ and the values of R$^8$, R$^{4a}$, R$^{4b}$ and R$^{4c}$ are given in Table 1.

Table CXXXVIII provides 575 compounds of formula Ial wherein T1 is $CR^{4b}$, T2 is N, T3 is $CR^{4a}$, T4 is $CR^{4a}$ and the values of $R^8$, $R^{4a}$, $R^{4b}$ and $R^{4c}$ are given in Table 1.

Table CXXXIX provides 575 compounds of formula Iam wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CXL provides 575 compounds of formula Ian wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CXLI provides 575 compounds of formula Iao wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CXLII provides 575 compounds of formula Iap wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CXLIII provides 575 compounds of formula Iaq wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CXLIV provides 575 compounds of formula Iar wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CXLV provides 575 compounds of formula Ias wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CXLVI provides 575 compounds of formula Iat wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CXLVII provides 575 compounds of formula Iau wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CXLVIII provides 575 compounds of formula Iav wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CIL provides 575 compounds of formula Iaw wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CL provides 575 compounds of formula Iax wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLI provides 575 compounds of formula wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLII provides 575 compounds of formula Iaz wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLIII provides 575 compounds of formula Iba wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLIV provides 575 compounds of formula Ibb wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLV provides 575 compounds of formula Ibc wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLVI provides 575 compounds of formula Ibd wherein T1 is $CR^{4b}$, T2 is N, T3 is $CR^{4a}$, T4 is CR and the values of $R^8$, $R^{4a}$, $R^{4b}$ and $R^{4c}$ are given in Table 1.

Table CLVII provides 575 compounds of formula Ibe wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLVIII provides 575 compounds of formula Ibf wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLIX provides 575 compounds of formula Ibg wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLX provides 575 compounds of formula Ibh wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLXI provides 575 compounds of formula Ibi wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLXII provides 575 compounds of formula Ibj wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLXIII provides 575 compounds of formula Ibk wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLXIV provides 575 compounds of formula Ibl wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLXV provides 575 compounds of formula Ibm wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLXVI provides 575 compounds of formula Ibn wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CLXVII provides 575 compounds of formula Ibo wherein T1 is $CR^{4b}$, T2 is N, T3 is $CR^{4a}$, T4 is $CR^{4c}$ and the values of $R^8$, $R^{4a}$, $R^{4b}$ and $R^{4c}$ are given in Table 1.

Table CCI provides 575 compounds of formula Ia wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCII provides 575 compounds of formula Ib wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCIII provides 575 compounds of formula Ic wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCIV provides 575 compounds of formula Id wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCV provides 575 compounds of formula Ie wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCVI provides 575 compounds of formula If wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCVII provides 575 compounds of formula Ig wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCVIII provides 575 compounds of formula Ih wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCIX provides 575 compounds of formula Ii wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCX provides 575 compounds of formula Ij wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXI provides 575 compounds of formula Ik wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXII provides 575 compounds of formula Il wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXIII provides 575 compounds of formula Im wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXIV provides 575 compounds of formula In wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXV provides 575 compounds of formula Io wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXVI provides 575 compounds of formula Ip wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXVII provides 575 compounds of formula Iq wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXVIII provides 575 compounds of formula Ir wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXIX provides 575 compounds of formula Is wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXX provides 575 compounds of formula It wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXI provides 575 compounds of formula Iu wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXII provides 575 compounds of formula Iv wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXIII provides 575 compounds of formula Iw wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXIV provides 575 compounds of formula Ix wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXV provides 575 compounds of formula Iy wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXVI provides 575 compounds of formula Iz wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXVII provides 575 compounds of formula Iaa wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXVIII provides 575 compounds of formula Iab wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXIX provides 575 compounds of formula Iac wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXX provides 575 compounds of formula Iad wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXXI provides 575 compounds of formula Iae wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXXII provides 575 compounds of formula Iaf wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXXIII provides 575 compounds of formula Iag wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXXIV provides 575 compounds of formula Iah wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXXV provides 575 compounds of formula Iai wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXXVI provides 575 compounds of formula Iaj wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXXVII provides 575 compounds of formula Iak wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXXVIII provides 575 compounds of formula Ial wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXXXIX provides 575 compounds of formula Iam wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXL provides 575 compounds of formula Ian wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXLI provides 575 compounds of formula Iao wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXLII provides 575 compounds of formula Iap wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXLIII provides 575 compounds of formula Iaq wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXLIV provides 575 compounds of formula Iar wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXLV provides 575 compounds of formula Ias wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXLVI provides 575 compounds of formula Iat wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXLVII provides 575 compounds of formula Iau wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCXLVIII provides 575 compounds of formula Iav wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCIL provides 575 compounds of formula Iaw wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCL provides 575 compounds of formula Iax wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCLI provides 575 compounds of formula wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCLII provides 575 compounds of formula Iaz wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCLIII provides 575 compounds of formula Iba wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCLIV provides 575 compounds of formula Ibb wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCLV provides 575 compounds of formula Ibc wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCLVI provides 575 compounds of formula Ibd wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCLVII provides 575 compounds of formula Ibe wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCLVIII provides 575 compounds of formula Ibf wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.

Table CCLIX provides 575 compounds of formula Ibg wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.
Table CCLX provides 575 compounds of formula Ibh wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.
Table CCLXI provides 575 compounds of formula Ibi wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.
Table CCLXII provides 575 compounds of formula Ibj wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.
Table CCLXIII provides 575 compounds of formula Ibk wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.
Table CCLXIV provides 575 compounds of formula Ibl wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.
Table CCLXV provides 575 compounds of formula Ibm wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.
Table CCLXVI provides 575 compounds of formula Ibn wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.
Table CCLXVII provides 575 compounds of formula Ibo wherein T1 is $CR^{4b}$, T2 is $CR^{4a}$, T3 is N, T4 is $CR^{4c}$ and the values of $R^8$, $R^{4a}$, $R^{4b}$ and $R^{4c}$ are given in Table 1.
Table CCCI provides 575 compounds of formula Ia wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCII provides 575 compounds of formula Ib wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCIII provides 575 compounds of formula Ic wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCIV provides 575 compounds of formula Id wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCV provides 575 compounds of formula Ie wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCVI provides 575 compounds of formula If wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCVII provides 575 compounds of formula Ig wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCVIII provides 575 compounds of formula Ih wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCIX provides 575 compounds of formula Ii wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCX provides 575 compounds of formula Ij wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXI provides 575 compounds of formula Ik wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXII provides 575 compounds of formula Il wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXIII provides 575 compounds of formula Im wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXIV provides 575 compounds of formula In wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXV provides 575 compounds of formula Io wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXVI provides 575 compounds of formula Ip wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXVII provides 575 compounds of formula Iq wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXVIII provides 575 compounds of formula Ir wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXIX provides 575 compounds of formula Is wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXX provides 575 compounds of formula It wherein T1 is $CR^{4c}$, T2 is $CR^{4a}$, T3 is $CR^{4b}$, T4 is N and the values of $R^8$, $R_{4a}$, $R^{4b}$ and $R^{4c}$ are given in Table 1.
Table CCCXXI provides 575 compounds of formula Iu wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXII provides 575 compounds of formula Iv wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXIII provides 575 compounds of formula Iw wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXIV provides 575 compounds of formula Ix wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXV provides 575 compounds of formula Iy wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXVI provides 575 compounds of formula Iz wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXVII provides 575 compounds of formula Iaa wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXVIII provides 575 compounds of formula Iab wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXIX provides 575 compounds of formula Iac wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXX provides 575 compounds of formula Iad wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXXI provides 575 compounds of formula Iae wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXXII provides 575 compounds of formula Iaf wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXXIII provides 575 compounds of formula Iag wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXXIV provides 575 compounds of formula Iah wherein T1 is $CR^{4c}$, T2 is $CR^{4a}$, T3 is $CR^{4b}$, T4 is N and the values of $R^8$, $R^{4b}$ and $R^{4c}$ are given in Table 1.
Table CCCXXXV provides 575 compounds of formula Iai wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.

Table CCCXXXVI provides 575 compounds of formula Iaj wherein T1 is $CR^{4a}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXXVII provides 575 compounds of formula Iak wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXXVIII provides 575 compounds of formula Ial wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXXXIX provides 575 compounds of formula Iam wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXL provides 575 compounds of formula Ian wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXLI provides 575 compounds of formula Iao wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXLII provides 575 compounds of formula Iap wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXLIII provides 575 compounds of formula Iaq wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXLIV provides 575 compounds of formula Iar wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXLV provides 575 compounds of formula Ias wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXLVI provides 575 compounds of formula Iat wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCXLVII provides 575 compounds of formula Iau wherein T1 is $CR^{4c}$, T2 is $CR^{4a}$, T3 is $CR^{4a}$, T4 is N and the values of $R^8$, $R^{4a}$, $R^{4b}$ and $R^{4c}$ are given in Table 1.
Table CCCXLVIII provides 575 compounds of formula Iav wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCIL provides 575 compounds of formula Iaw wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCL provides 575 compounds of formula Iax wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLI provides 575 compounds of formula wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLII provides 575 compounds of formula Iaz wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLIII provides 575 compounds of formula Iba wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLIV provides 575 compounds of formula Ibb wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLV provides 575 compounds of formula Ibc wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLVI provides 575 compounds of formula Ibd wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLVII provides 575 compounds of formula Ibe wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLVIII provides 575 compounds of formula Ibf wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLIX provides 575 compounds of formula Ibg wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLX provides 575 compounds of formula Ibh wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLXI provides 575 compounds of formula Ibi wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLXII provides 575 compounds of formula Ibj wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLXIII provides 575 compounds of formula Ibk wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLXIV provides 575 compounds of formula Ibl wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLXV provides 575 compounds of formula Ibm wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLXVI provides 575 compounds of formula Ibn wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CCCLXVII provides 575 compounds of formula Ibo wherein T1 is $CR^{4c}$, T2 is $CR^{4a}$, T3 is $CR^{4b}$, T4 is N and the values of $R^8$, $R^{4a}$, $R^{4b}$ and $R^{4c}$ are given in Table 1.
Table CDI provides 345 compounds of formula Ia wherein T1 is N, T2 is $CR^{4c}$, T3 is N, T4 is $CR^{4f}$ and the values of $R^8$, $R^{4e}$ and $R^{4f}$ are given in Table 2.

TABLE 2

| Compound No | $R^8$ | $C-R^{4e}$ | $C-R^{4f}$ |
|---|---|---|---|
| CDI-1 | 4-chlorobenzyl | CH | CH |
| CD1-2 | Cinnamyl | CH | CH |
| CD1-3 | 4-chlorocinnamyl | CH | CH |
| CD1-4 | 4-fluorocinnamyl | CH | CH |
| CD1-5 | 4-bromocinnamyl | CH | CH |
| CD1-6 | 4-trifluoromethylcinnamyl | CH | CH |
| CD1-7 | 4-trifluoromethoxycinnamyl | CH | CH |
| CD1-8 | 4-pentafluoroethoxycinnamyl | CH | CH |
| CD1-9 | 4-methoxycinnamyl | CH | CH |
| CD1-10 | 4-ethoxycinnamyl | CH | CH |
| CD1-11 | 4-cyanocinnamyl | CH | CH |
| CD1-12 | 3-(6-chloro-pyridin-3-yl)-allyl | CH | CH |
| CD1-13 | 3-(4-chlorophenyl)-but-2-enyl | CH | CH |
| CD1-14 | 3-(4-chlorophenyl)-3-fluoro-allyl | CH | CH |
| CD1-15 | 3-chloro-4-fluoro-cinnamyl | CH | CH |
| CD1-16 | 3,5-dichloro-cinnamyl | CH | CH |
| CD1-17 | 5-phenyl-penta-2,4-dienyl | CH | CH |
| CD1-18 | 4-isopropyloxycarbonylamino-cinnamyl | CH | CH |
| CD1-19 | 3-naphthalen-2-yl-allyl | CH | CH |
| CD1-20 | 3-(5-trifluoromethyl-pyridin-2-yl)-allyl | CH | CH |
| CD1-21 | 3-(5-chloro-pyridin-2-yl)-allyl | CH | CH |
| CD1-22 | 3-pyridin-4-yl-allyl | CH | CH |
| CD1-23 | 3-(2-Chloro-pyridin-4-yl)-allyl | CH | CH |
| CD1-24 | 4-chlorobenzyl | CF | CH |
| CD1-25 | Cinnamyl | CF | CH |
| CD1-26 | 4-chlorocinnamyl | CF | CH |
| CD1-27 | 4-fluorocinnamyl | CF | CH |
| CD1-28 | 4-bromocinnamyl | CF | CH |
| CD1-29 | 4-trifluoromethylcinnamyl | CF | CH |
| CD1-30 | 4-trifluoromethoxycinnamyl | CF | CH |
| CD1-31 | 4-pentafluoroethoxycinnamyl | CF | CH |
| CD1-32 | 4-methoxycinnamyl | CF | CH |
| CD1-33 | 4-ethoxycinnamyl | CF | CH |
| CD1-34 | 4-cyanocinnamyl | CF | CH |

TABLE 2-continued

| Compound No | R[8] | C—R[4e] | C—R[4f] |
|---|---|---|---|
| CD1-35 | 3-(6-chloro-pyridin-3-yl)-allyl | CF | CH |
| CD1-36 | 3-(4-chlorophenyl)-but-2-enyl | CF | CH |
| CD1-37 | 3-(4-chlorophenyl)-3-fluoro-allyl | CF | CH |
| CD1-38 | 3-chloro-4-fluoro-cinnamyl | CF | CH |
| CD1-39 | 3,5-dichloro-cinnamyl | CF | CH |
| CD1-40 | 5-phenyl-penta-2,4-dienyl | CF | CH |
| CD1-41 | 4-isopropyloxycarbonylamino-cinnamyl | CF | CH |
| CD1-42 | 3-naphthalen-2-yl-allyl | CF | CH |
| CD1-43 | 3-(5-trifluoromethyl-pyridin-2-yl)-allyl | CF | CH |
| CD1-44 | 3-(5-chloro-pyridin-2-yl)-allyl | CF | CH |
| CD1-45 | 3-pyridin-4-yl-allyl | CF | CH |
| CD1-46 | 3-(2-Chloro-pyridin-4-yl)-allyl | CF | CH |
| CD1-47 | 4-chlorobenzyl | CCl | CH |
| CD1-48 | Cinnamyl | CCl | CH |
| CD1-49 | 4-chlorocinnamyl | CCl | CH |
| CD1-50 | 4-fluorocinnamyl | CCl | CH |
| CD1-51 | 4-bromocinnamyl | CCl | CH |
| CD1-52 | 4-trifluoromethylcinnamyl | CCl | CH |
| CD1-53 | 4-trifluoromethoxycinnamyl | CCl | CH |
| CD1-54 | 4-pentafluoroethoxycinnamyl | CCl | CH |
| CD1-55 | 4-methoxycinnamyl | CCl | CH |
| CD1-56 | 4-ethoxycinnamyl | CCl | CH |
| CD1-57 | 4-cyanocinnamyl | CCl | CH |
| CD1-58 | 3-(6-chloro-pyridin-3-yl)-allyl | CCl | CH |
| CD1-59 | 3-(4-chlorophenyl)-but-2-enyl | CCl | CH |
| CD1-60 | 3-(4-chlorophenyl)-3-fluoro-allyl | CCl | CH |
| CD1-61 | 3-chloro-4-fluoro-cinnamyl | CCl | CH |
| CD1-62 | 3,5-dichloro-cinnamyl | CCl | CH |
| CD1-63 | 5-phenyl-penta-2,4-dienyl | CCl | CH |
| CD1-64 | 4-isopropyloxycarbonylamino-cinnamyl | CCl | CH |
| CD1-65 | 3-naphthalen-2-yl-allyl | CCl | CH |
| CD1-66 | 3-(5-trifluoromethyl-pyridin-2-yl)-allyl | CCl | CH |
| CD1-67 | 3-(5-chloro-pyridin-2-yl)-allyl | CCl | CH |
| CD1-68 | 3-pyridin-4-yl-allyl | CCl | CH |
| CD1-69 | 3-(2-Chloro-pyridin-4-yl)-allyl | CCl | CH |
| CD1-70 | 4-chlorobenzyl | CBr | CH |
| CD1-71 | Cinnamyl | CBr | CH |
| CD1-72 | 4-chlorocinnamyl | CBr | CH |
| CD1-73 | 4-fluorocinnamyl | CBr | CH |
| CD1-74 | 4-bromocinnamyl | CBr | CH |
| CD1-75 | 4-trifluoromethylcinnamyl | CBr | CH |
| CD1-76 | 4-trifluoromethoxycinnamyl | CBr | CH |
| CD1-77 | 4-pentafluoroethoxycinnamyl | CBr | CH |
| CD1-78 | 4-methoxycinnamyl | CBr | CH |
| CD1-79 | 4-ethoxycinnamyl | CBr | CH |
| CD1-80 | 4-cyanocinnamyl | CBr | CH |
| CD1-81 | 3-(6-chloro-pyridin-3-yl)-allyl | CBr | CH |
| CD1-82 | 3-(4-chlorophenyl)-but-2-enyl | CBr | CH |
| CD1-83 | 3-(4-chlorophenyl)-3-fluoro-allyl | CBr | CH |
| CD1-84 | 3-chloro-4-fluoro-cinnamyl | CBr | CH |
| CD1-85 | 3,5-dichloro-cinnamyl | CBr | CH |
| CD1-86 | 5-phenyl-penta-2,4-dienyl | CBr | CU |
| CD1-87 | 4-isopropyloxycarbonylamino-cinnamyl | CBr | CH |
| CD1-88 | 3-naphthalen-2-yl-allyl | CBr | CH |
| CD1-89 | 3-(5-trifluoromethyl-pyridin-2-yl)-allyl | CBr | CH |
| CD1-90 | 3-(5-chloro-pyridin-2-yl)-allyl | CBr | CH |
| CD1-91 | 3-pyridin-4-yl-allyl | CBr | CH |
| CD1-92 | 3-(2-Chloro-pyridin-4-yl)-allyl | CBr | CH |
| CD1-93 | 4-chlorobenzyl | CCN | CH |
| CD1-94 | Cinnamyl | CCN | CH |
| CD1-95 | 4-chlorocinnamyl | CCN | CH |
| CD1-96 | 4-fluorocinnamyl | CCN | CH |
| CD1-97 | 4-bromocinnamyl | CCN | CH |
| CD1-98 | 4-trifluoromethylcinnamyl | CCN | CH |
| CD1-99 | 4-trifluoromethoxycinnamyl | CCN | CH |
| CD1-100 | 4-pentafluoroethoxycinnamyl | CCN | CH |
| CD1-101 | 4-methoxycinnamyl | CCN | CH |
| CD1-102 | 4-ethoxycinnamyl | CCN | CH |
| CD1-103 | 4-cyanocinnamyl | CCN | CH |
| CD1-104 | 3-(6-chloro-pyridin-3-yl)-allyl | CCN | CH |
| CD1-105 | 3-(4-chlorophenyl)-but-2-enyl | CCN | CH |
| CD1-106 | 3-(4-chlorophenyl)-3-fluoro-allyl | CCN | CH |
| CD1-107 | 3-chloro-4-fluoro-cinnamyl | CCN | CH |
| CD1-108 | 3,5-dichloro-cinnamyl | CCN | CH |
| CD1-109 | 5-phenyl-penta-2,4-dienyl | CCN | CH |
| CD1-110 | 4-isopropyloxycarbonylamino-cinnamyl | CCN | CH |
| CD1-111 | 3-naphthalen-2-yl-allyl | CCN | CH |
| CD1-112 | 3-(5-trifluoromethyl-pyridin-2-yl)-allyl | CCN | CH |
| CD1-113 | 3-(5-chloro-pyridin-2-yl)-allyl | CCN | CH |
| CD1-114 | 3-pyridin-4-yl-allyl | CCN | CH |
| CD1-115 | 3-(2-Chloro-pyridin-4-yl)-allyl | CCN | CH |
| CD1-116 | 4-chlorobenzyl | COMe | CH |
| CD1-117 | Cinnamyl | COMe | CH |
| CD1-118 | 4-chlorocinnamyl | COMe | CH |
| CD1-119 | 4-fluorocinnamyl | COMe | CH |
| CD1-120 | 4-bromocinnamyl | COMe | CH |
| CD1-121 | 4-trifluoromethylcinnamyl | COMe | CH |
| CD1-122 | 4-trifluoromethoxycinnamyl | COMe | CH |
| CD1-123 | 4-pentafluoroethoxycinnamyl | COMe | CH |
| CD1-124 | 4-methoxycinnamyl | COMe | CH |
| CD1-125 | 4-ethoxycinnamyl | COMe | CH |
| CD1-126 | 4-cyanocinnamyl | COMe | CH |
| CD1-127 | 3-(6-chloro-pyridin-3-yl)-allyl | COMe | CH |
| CD1-128 | 3-(4-chlorophenyl)-but-2-enyl | COMe | CH |
| CD1-129 | 3-(4-chlorophenyl)-3-fluoro-allyl | COMe | CH |
| CD1-130 | 3-chloro-4-fluoro-cinnamyl | COMe | CH |
| CD1-131 | 3,5-dichloro-cinnamyl | COMe | CH |
| CD1-132 | 5-phenyl-penta-2,4-dienyl | COMe | CH |
| CD1-133 | 4-isopropyloxycarbonylamino-cinnamyl | COMe | CH |
| CD1-134 | 3-napthalen-2-yl-allyl | COMe | CH |
| CD1-135 | 3-(5-trifluoromethyl-pyridin-2-yl)-allyl | COMe | CH |
| CD1-136 | 3-(5-chloro-pyridin-2-yl)-allyl | COMe | CH |
| CD1-137 | 3-pyridin-4-yl-allyl | COMe | CH |
| CD1-138 | 3-(2-Chloro-pyridin-4-yl)-allyl | COMe | CH |
| CD1-139 | 4-chlorobenzyl | COCF$_3$ | CH |
| CD1-140 | Cinnamyl | COCF$_3$ | CH |
| CD1-141 | 4-chlorocinnamyl | COCF$_3$ | CH |
| CD1-142 | 4-fluorocinnamyl | COCF$_3$ | CH |
| CD1-143 | 4-bromocinnamyl | COCF$_3$ | CH |
| CD1-144 | 4-trifluoromethylcinnamyl | COCF$_3$ | CH |
| CD1-145 | 4-trifluoromethoxycinnamyl | COCF$_3$ | CH |
| CD1-146 | 4-pentafluoroethoxycinnamyl | COCF$_3$ | CH |
| CD1-147 | 4-methoxycinnamyl | COCF$_3$ | CH |
| CD1-148 | 4-ethoxycinnamyl | COCF$_3$ | CH |
| CD1-149 | 4-cyanocinnamyl | COCF$_3$ | CH |
| CD1-150 | 3-(6-chloro-pyridin-3-yl)-allyl | COCF$_3$ | CH |
| CD1-151 | 3-(4-chlorophenyl)-but-2-enyl | COCF$_3$ | CH |
| CD1-152 | 3-(4-chlorophenyl)-3-fluoro-allyl | COCF$_3$ | CH |
| CD1-153 | 3-chloro-4-fluoro-cinnamyl | COCF$_3$ | CH |
| CD1-154 | 3,5-dichloro-cinnamyl | COCF$_3$ | CH |
| CD1-155 | 5-phenyl-penta-2,4-dienyl | COCF$_3$ | CH |
| CD1-156 | 4-isopropyloxycarbonylamino-cinnamyl | COCF$_3$ | CH |
| CD1-157 | 3-naphthalen-2-yl-allyl | COCF$_3$ | CH |
| CD1-158 | 3-(5-trifluoromethyl-pyrdin-2-yl)-allyl | COCF$_3$ | CH |
| CD1-159 | 3-(5-chloro-pyridin-2yl)-allyl | COCF$_3$ | CH |
| CD1-160 | 3-pyridin-4-yl-allyl | COCF$_3$ | CH |
| CD1-161 | 3-(2-Chloro-pyridin-4-yl)-allyl | COCF$_3$ | CH |
| CD1-162 | 4-chlorobenzyl | CCH$_3$ | CH |
| CD1-163 | Cinnamyl | CCH$_3$ | CH |
| CD1-164 | 4-chlorocinnamyl | CCH$_3$ | CH |
| CD1-165 | 4-fluorocinnamyl | CCH$_3$ | CH |
| CD1-166 | 4-bromocinnamyl | CCH$_3$ | CH |
| CD1-167 | 4-trifluoromethylcinnamyl | CCH$_3$ | CH |
| CD1-168 | 4-trifluoromethoxycinnamyl | CCH$_3$ | CH |
| CD1-169 | 4-pentafluoroethoxycinnamyl | CCH$_3$ | CH |
| CD1-170 | 4-methoxycinnamyl | CCH$_3$ | CH |
| CD1-171 | 4-ethoxycinnamyl | CCH$_3$ | CH |
| CD1-172 | 4-cyanocinnamyl | CCH$_3$ | CH |
| CD1-173 | 3-(6-chloro-pyridin-3-yl)-allyl | CCH$_3$ | CH |
| CD1-174 | 3-(4-chlorophenyl)-but-2-enyl | CCH$_3$ | CH |
| CD1-175 | 3-(4-chlorophenyl)-3-fluoro-allyl | CCH$_3$ | CH |
| CD1-176 | 3-chloro-4-fluoro-cinnamyl | CCH$_3$ | CH |
| CD1-177 | 3,5-dichloro-cinnamyl | CCH$_3$ | CH |
| CD1-178 | 5-phenyl-penta-2,4-dienyl | CCH$_3$ | CH |
| CD1-179 | 4-isopropyloxycarbonylamino-cinnamyl | CCH$_3$ | CH |
| CD1-180 | 3-naphthalen-2-yl-allyl | CCH$_3$ | CH |
| CD1-181 | 3-(5-trifluoromethyl-pyridin-2-yl)-allyl | CCH$_3$ | CH |
| CD1-182 | 3-(5-chloro-pyridin-2-yl)-allyl | CCH$_3$ | CH |
| CD1-183 | 3-pyridin-4-yl-allyl | CCH$_3$ | CH |
| CD1-184 | 3-(2-Chloro-pyridin-4-yl)-allyl | CCH$_3$ | CH |
| CD1-185 | 4-chlorobenzyl | CCF$_3$ | CH |
| CD1-186 | Cinnamyl | CCF$_3$ | CH |
| CD1-187 | 4-chlorocinnamyl | CCF$_3$ | CH |
| CD1-188 | 4-fluorocinnamyl | CCF$_3$ | CH |

TABLE 2-continued

| Compound No | R⁸ | C—R⁴ᵉ | C—R⁴ᶠ |
|---|---|---|---|
| CD1-189 | 4-bromocinnamyl | CCF₃ | CH |
| CD1-190 | 4-trifluoromethylcinnamyl | CCF₃ | CH |
| CD1-191 | 4-trifluoromethoxycinnamyl | CCF₃ | CH |
| CD1-192 | 4-pentafluoroethoxycinnamyl | CCF₃ | CH |
| CD1-193 | 4-methoxycinnamyl | CCF₃ | CH |
| CD1-194 | 4-ethoxycinnamyl | CCF₃ | CH |
| CD1-195 | 4-cyanocinnamyl | CCF₃ | CH |
| CD1-196 | 3-(6-chloro-pyridin-3-yl)-allyl | CCF₃ | CH |
| CD1-197 | 3-(4-chlorophenyl)-but-2-enyl | CCF₃ | CH |
| CD1-198 | 3-(4-chlorophenyl)-3-fluoro-allyl | CCF₃ | CH |
| CD1-199 | 3-chloro-4-fluoro-cinnamyl | CCF₃ | CH |
| CD1-200 | 3,5-dichloro-cinnamyl | CCF₃ | CH |
| CD1-201 | 5-phenyl-penta-2,4-dienyl | CCF₃ | CH |
| CD1-202 | 4-isopropyloxycarbonylamino-cinnamyl | CCF₃ | CH |
| CD1-203 | 3-naphthalen-2-yl-allyl | CCF₃ | CH |
| CD1-204 | 3-(5-trifluoromethyl-pyridin-2-yl)-allyl | CCF₃ | CH |
| CD1-205 | 3-(5-chloro-pyridin-2-yl)-allyl | CCF₃ | CH |
| CD1-206 | 3-pyridin-4-yl-allyl | CCF₃ | CH |
| CD1-207 | 3-(2-Chloro-pyridin-4-yl)-allyl | CCF₃ | CH |
| CD1-208 | 4-chlorobenzyl | CH | CCl |
| CD1-209 | Cinnamyl | CH | CCl |
| CD1-210 | 4-chlorocinnamyl | CH | CCl |
| CD1-211 | 4-fluorocinnamyl | CH | CCl |
| CD1-212 | 4-bromocinnamyl | CH | CCl |
| CD1-213 | 4-trifluoromethylcinnamyl | CH | CCl |
| CD1-214 | 4-trifluoromethoxycinnamyl | CH | CCl |
| CD1-215 | 4-pentafluoroethoxycinnamyl | CH | CCl |
| CD1-216 | 4-methoxycinnamyl | CH | CCl |
| CD1-217 | 4-ethoxycinnamyl | CH | CCl |
| CD1-218 | 4-cyanocinnamyl | CH | CCl |
| CD1-219 | 3-(6-chloro-pyridin-3-yl)-allyl | CH | CCl |
| CD1-220 | 3-(4-chlorophenyl)-but-2-enyl | CH | CCl |
| CD1-221 | 3-(4-chlorophenyl)-3-fluoro-allyl | CH | CCl |
| CD1-222 | 3-chloro-4-fluoro-cinnamyl | CH | CCl |
| CD1-223 | 3,5-dichloro-cinnamyl | CH | CCl |
| CD1-224 | 5-phenyl-penta-2,4-dienyl | CH | CCl |
| CD1-225 | 4-isopropyloxycarbonylamino-cinnamyl | CH | CCl |
| CD1-226 | 3-naphthalen-2-yl-allyl | CH | CCl |
| CD1-227 | 3-(5-trifluoromethyl-pyridin-2-yl)-allyl | CH | CCl |
| CD1-228 | 3-(5-chloro-pyridin-2-yl)-allyl | CH | CCl |
| CD1-229 | 3-pyridin-4-yl-allyl | CH | CCl |
| CD1-230 | 3-(2-Chloro-pyridin-4-yl)-allyl | CH | CCl |
| CD1-231 | 4-chlorobenzyl | CH | CF |
| CD1-232 | Cinnamyl | CH | CF |
| CD1-233 | 4-chlorocinnamyl | CH | CF |
| CD1-234 | 4-fluorocinnamyl | CH | CF |
| CD1-235 | 4-bromocinnamyl | CH | CF |
| CD1-236 | 4-trifluoromethylcinnamyl | CH | CF |
| CD1-237 | 4-trifluoromethoxycinnamyl | CH | CF |
| CD1-238 | 4-pentafluoroethoxycinnamyl | CH | CF |
| CD1-239 | 4-methoxycinnamyl | CH | CF |
| CD1-240 | 4-ethoxycinnamyl | CH | CF |
| CD1-241 | 4-cyanocinnamyl | CH | CF |
| CD1-242 | 3-(6-chloro-pyridin-3-yl)-allyl | CH | CF |
| CD1-243 | 3-(4-chlorophenyl)-but-2-enyl | CH | CF |
| CD1-244 | 3-(4-chlorophenyl)-3-fluoro-allyl | CH | CF |
| CD1-245 | 3-chloro-4-fluoro-cinnamyl | CH | CF |
| CD1-246 | 3,5-dichloro-cinnamyl | CH | CF |
| CD1-247 | 5-phenyl-penta-2,4-dienyl | CH | CF |
| CD1-248 | 4-isopropyloxycarbonylamino-cinnamyl | CH | CF |
| CD1-249 | 3-naphthalen-2-yl-allyl | CH | CF |
| CD1-250 | 3-(5-trifluoromethyl-pyridin-2-yl)-allyl | CH | CF |
| CD1-251 | 3-(5-chloro-pyridin-2-yl)-allyl | CH | CF |
| CD1-252 | 3-pyridin-4-yl-allyl | CH | CF |
| CD1-253 | 3-(2-Chloro-pyridin-4-yl)-allyl | CH | CF |
| CD1-254 | 4-chlorobenzyl | CCl | CCl |
| CD1-255 | Cinnamyl | CCl | CCl |
| CD1-256 | 4-chlorocinnamyl | CCl | CCl |
| CD1-257 | 4-fluorocinnamyl | CCl | CCl |
| CD1-258 | 4-bromocinnamyl | CCl | CCl |
| CD1-259 | 4-trifluoromethylcinnamyl | CCl | CCl |
| CD1-260 | 4-trifluoromethoxycinnamyl | CCl | CCl |
| CD1-261 | 4-pentafluoroethoxycinnamyl | CCl | CCl |
| CD1-262 | 4-methoxycinnamyl | CCl | CCl |
| CD1-263 | 4-ethoxycinnamyl | CCl | CCl |
| CD1-264 | 4-cyanocinnamyl | CCl | CCl |
| CD1-265 | 3-(6-chloro-pyridin-3-yl)-allyl | CCl | CCl |
| CD1-266 | 3-(4-chlorophenyl)-but-2-enyl | CCl | CCl |
| CD1-267 | 3-(4-chlorophenyl)-3-fluoro-allyl | CCl | CCl |
| CD1-268 | 3-chloro-4-fluoro-cinnamyl | CCl | CCl |
| CD1-269 | 3,5-dichloro-cinnamyl | CCl | CCl |
| CD1-270 | 5-phenyl-penta-2,4-dienyl | CCl | CCl |
| CD1-271 | 4-isopropyloxycarbonylamino-cinnamyl | CCl | CCl |
| CD1-272 | 3-naphthalen-2-yl-allyl | CCl | CCl |
| CD1-273 | 3-(5-trifluoromethyl-pyridin-2-yl)-allyl | CCl | CCl |
| CD1-274 | 3-(5-chloro-pyridin-2-yl)-allyl | CCl | CCl |
| CD1-275 | 3-pyridin-4-yl-allyl | CCl | CCl |
| CD1-276 | 3-(2-Chloro-pyridin-4-yl)-allyl | CCl | CCl |
| CD1-277 | 4-chlorobenzyl | CF | CCl |
| CD1-278 | Cinnamyl | CF | CCl |
| CD1-279 | 4-chlorocinnamyl | CF | CCl |
| CD1-280 | 4-fluorocinnamyl | CF | CCl |
| CD1-281 | 4-bromocinnamyl | CF | CCl |
| CD1-282 | 4-trifluoromethylcinnamyl | CF | CCl |
| CD1-283 | 4-trifluoromethoxycinnamyl | CF | CCl |
| CD1-284 | 4-pentafluoroethoxycinnamyl | CF | CCl |
| CD1-285 | 4-methoxycinnamyl | CF | CCl |
| CD1-286 | 4-ethoxycinnamyl | CF | CCl |
| CD1-287 | 4-cyanocinnamyl | CF | CCl |
| CD1-288 | 3-(6-chloro-pyridin-3-yl)-allyl | CF | CCl |
| CD1-289 | 3-(4-chlorophenyl)-but-2-enyl | CF | CCl |
| CD1-290 | 3-(4-chlorophenyl)-3-fluoro-allyl | CF | CCl |
| CD1-291 | 3-chloro-4-fluoro-cinnamyl | CF | CCl |
| CD1-292 | 3,5-dichloro-cinnamyl | CF | CCl |
| CD1-293 | 5-phenyl-penta-2,4-dienyl | CF | CCl |
| CD1-294 | 4-isopropyloxycarbonylamino-cinnamyl | CF | CCl |
| CD1-295 | 3-naphthalen-2-yl-allyl | CF | CCl |
| CD1-296 | 3-(5-trifluoromethyl-pyridin-2-yl)-allyl | CF | CCl |
| CD1-297 | 3-(5-chloro-pyridin-2-yl)-allyl | CF | CCl |
| CD1-298 | 3-pyridin-4-yl-allyl | CF | CCl |
| CD1-299 | 3-(2-Chloro-pyridin-4-yl)-allyl | CF | CCl |
| CD1-300 | 4-chlorobenzyl | CCl | CF |
| CD1-301 | Cinnamyl | CCl | CF |
| CD1-302 | 4-chlorocinnamyl | CCl | CF |
| CD1-303 | 4-fluorocinnamyl | CCl | CF |
| CD1-304 | 4-bromocinnamyl | CCl | CF |
| CD1-305 | 4-trifluoromethylcinnamyl | CCl | CF |
| CD1-306 | 4-trifluoromethoxycinnamyl | CCl | CF |
| CD1-307 | 4-pentafluoroethoxycinnamyl | CCl | CF |
| CD1-308 | 4-methoxycinnamyl | CCl | CF |
| CD1-309 | 4-ethoxycinnamyl | CCl | CF |
| CD1-310 | 4-cyanocinnamyl | CCl | CF |
| CD1-311 | 3-(6-chloro-pyridin-3-yl)-allyl | CCl | CF |
| CD1-312 | 3-(4-chlorophenyl)-but-2-enyl | CCl | CF |
| CD1-313 | 3-(4-chlorophenyl)-3-fluoro-allyl | CCl | CF |
| CD1-314 | 3-chloro-4-fluoro-cinnamyl | CCl | CF |
| CD1-315 | 3,5-dichloro-cinnamyl | CCl | CF |
| CD1-316 | 5-phenyl-penta-2,4-dienyl | CCl | CF |
| CD1-317 | 4-isopropyloxycarbonylamino-cinnamyl | CCl | CF |
| CD1-318 | 3-naphthalen-2-yl-allyl | CCl | CF |
| CD1-319 | 3-(5-trifluoromethyl-pyridin-2-yl)-allyl | CCl | CF |
| CD1-320 | 3-(5-chloro-pyridin-2-yl)-allyl | CCl | CF |
| CD1-321 | 3-pyridin-4-yl-allyl | CCl | CF |
| CD1-322 | 3-(2-Chloro-pyridin-4-yl)-allyl | CCl | CF |
| CD1-323 | 4-chlorobenzyl | CF | CF |
| CD1-324 | Cinnamyl | CF | CF |
| CD1-325 | 4-chlorocinnamyl | CF | CF |
| CD1-326 | 4-fluorocinnamyl | CF | CF |
| CD1-327 | 4-bromocinnamyl | CF | CF |
| CD1-328 | 4-trifluoromethylcinnamyl | CF | CF |
| CD1-329 | 4-trifluoromethoxycinnamyl | CF | CF |
| CD1-330 | 4-pentafluoroethoxycinnamyl | CF | CF |
| CD1-331 | 4-methoxycinnamyl | CF | CF |
| CD1-332 | 4-ethoxycinnamyl | CF | CF |
| CD1-333 | 4-cyanocinnamyl | CF | CF |
| CD1-334 | 3-(6-chloro-pyridin-3-yl)-allyl | CF | CF |
| CD1-335 | 3-(4-chlorophenyl)-but-2-enyl | CF | CF |
| CD1-336 | 3-(4-chlorophenyl)-3-fluoro-allyl | CF | CF |
| CD1-337 | 3-chloro-4-fluoro-cinnamyl | CF | CF |
| CD1-338 | 3,5-dichloro-cinnamyl | CF | CF |
| CD1-339 | 5-phenyl-penta-2,4-dienyl | CF | CF |
| CD1-340 | 4-isopropyloxycarbonylamino-cinnamyl | CF | CF |
| CD1-341 | 3-naphthalen-2-yl-allyl | CF | CF |
| CD1-342 | 3-(5-trifluoromethyl-pyridin-2-yl)-allyl | CF | CF |

TABLE 2-continued

| Compound No | R⁸ | C—R⁴ᵉ | C—R⁴ᶠ |
|---|---|---|---|
| CD1-343 | 3-(5-chloro-pyridin-2-yl)-allyl | CF | CF |
| CD1-344 | 3-pyridin-4-yl-allyl | CF | CF |
| CD1-345 | 3-(2-Chloro-pyridin-4-yl)-allyl | CF | CF |

Table CDII provides 345 compounds of formula Ib wherein T1 is N, T2 is CR⁴ᵉ, T3 is N, T4 is CR⁴ᶠ and the values of R8, R⁴ᵉ and R⁴ᶠ are given in Table 2.

Table CDIII provides 345 compounds of formula Ic wherein T1 is N, T2 is CR⁴ᵉ, T3 is N, T4 is CR⁴ᶠ and the values of R8, R⁴ᵉ and R⁴ᶠ are given in Table 2.

Table CDIV provides 345 compounds of formula Id wherein T1 is N, T2 is CR⁴ᵉ, T3 is N, T4 is CR⁴ᶠ and the values of R8, R⁴ᵉ and R⁴ᶠ are given in Table 2.

Table CDV provides 345 compounds of formula Ie wherein T1 is N, T2 is CR⁴ᵉ, T3 is N, T4 is CR⁴ᶠ and the values of R8, R⁴ᵉ and R⁴ᶠ are given in Table 2.

Table CDVI provides 345 compounds of formula If wherein T1 is N, T2 is CR⁴ᵉ, T3 is N, T4 is CR⁴ᶠ and the values of R8, R⁴ᵉ and R⁴ᶠ are given in Table 2.

Table CDVII provides 345 compounds of formula Ig wherein T1 is N, T2 is CR⁴ᵉ, T3 is N, T4 is CR⁴ᶠ and the values of R8, R⁴ᵉ and R⁴ᶠ are given in Table 2.

Table CDVIII provides 345 compounds of formula Ih wherein T1 is N, T2 is CR⁴ᵉ, T3 is N, T4 is CR⁴ᶠ and the values of R8, R⁴ᵉ and R⁴ᶠ are given in Table 2.

Table CDIX provides 345 compounds of formula Ii wherein T1 is N, T2 is CR⁴ᵉ, T3 is N, T4 is CR⁴ᶠ and the values of R8, R⁴ᵉ and R⁴ᶠ are given in Table 2.

Table CDX provides 345 compounds of formula Ij wherein T1 is N, T2 is CR⁴ᵉ, T3 is N, T4 is CR⁴ᶠ and the values of R8, R⁴ᵉ and R⁴ᶠ are given in Table 2.

Table CDXI provides 345 compounds of formula Ik wherein T1 is N, T2 is CR⁴ᵉ, T3 is N, T4 is CR⁴ᶠ and the values of R8, R⁴ᵉ and R⁴ᶠ are given in Table 2.

Table CDXII provides 345 compounds of formula Il wherein T1 is N, T2 is CR⁴ᵉ, T3 is N, T4 is CR⁴ᶠ and the values of R8, R⁴ᵉ and R⁴ᶠ are given in Table 2.

Table CDXIII provides 345 compounds of formula Im wherein T1 is N, T2 is CR⁴ᵉ, T3 is N, T4 is CR⁴ᶠ and the values of R8, R⁴ᵉ and R⁴ᶠ are given in Table 2.

Table CDXIV provides 345 compounds of formula In wherein T1 is N, T2 is CR⁴ᵉ, T3 is N, T4 is CR⁴ᶠ and the values of R8, R⁴ᵉ and R⁴ᶠ are given in Table 2.

Table CDXV provides 345 compounds of formula Io wherein T1 is N, T2 is CR⁴ᵉ, T3 is N, T4 is CR⁴ᶠ and the values of R8, R⁴ᵉ and R⁴ᶠ are given in Table 2.

Table CDXVI provides 345 compounds of formula Ip wherein T1 is N, T2 is CR⁴ᵉ, T3 is N, T4 is CR⁴ᶠ and the values of R8, R⁴ᵉ and R⁴ᶠ are given in Table 2.

Table CDXVII provides 345 compounds of formula Iq wherein T1 is N, T2 is CR⁴ᵉ, T3 is N, T4 is CR⁴ᶠ and the values of R8, R⁴ᵉ and R⁴ᶠ are given in Table 2.

Table CDXVIII provides 345 compounds of formula Ir wherein T1 is N, T2 is CR⁴ᵉ, T3 is N, T4 is CR⁴ᶠ and the values of R8, R⁴ᵉ and R⁴ᶠ are given in Table 2.

Table CDXIX provides 345 compounds of formula Is wherein T1 is N, T2 is CR⁴ᵉ, T3 is N, T4 is CR⁴ᶠ and the values of R8, R⁴ᵉ and R⁴ᶠ are given in Table 2.

Table CDXX provides 345 compounds of formula It wherein T1 is N, T2 is CR⁴ᵉ, T3 is N, T4 is CR⁴ᶠ and the values of R8, R⁴ᵉ and R⁴ᶠ are given in Table 2.

Table CDXXI provides 345 compounds of formula Iu wherein T1 is N, T2 is CR⁴ᵉ, T3 is N, T4 is CR⁴ᶠ and the values of R8, R⁴ᵉ and R⁴ᶠ are given in Table 2.

Table CDXXII provides 345 compounds of formula Iv wherein T1 is N, T2 is CR⁴ᵉ, T3 is N, T4 is CR⁴ᶠ and the values of R8, R⁴ᵉ and R⁴ᶠ are given in Table 2.

Table CDXXIII provides 345 compounds of formula Iw wherein T1 is N, T2 is CR⁴, T3 is N, T4 is CR⁴ᶠ and the values of R8, R⁴ᵉ and R⁴ᶠ are given in Table 2.

Table CDXXIV provides 345 compounds of formula Ix wherein T1 is N, T2 is CR⁴ᵉ, T3 is N, T4 is CR⁴ᶠ and the values of R8, R⁴ᵉ and R⁴ᶠ are given in Table 2.

Table CDXXV provides 345 compounds of formula Iy wherein T1 is N, T2 is CR⁴ᵉ, T3 is N, T4 is CR⁴ᶠ and the values of R8, R⁴ᵉ and R⁴ᶠ are given in Table 2.

Table CDXXVI provides 345 compounds of formula Iz wherein T1 is N, T2 is CR⁴ᵉ, T3 is N, T4 is CR⁴ᶠ and the values of R8, R⁴ᵉ and R⁴ᶠ are given in Table 2.

Table CDXXVII provides 345 compounds of formula Iaa wherein T1 is N, T2 is CR⁴ᵉ, T3 is N, T4 is CR⁴ᶠ and the values of R8, R⁴ᵉ and R⁴ᶠ are given in Table 2.

Table CDXXVIII provides 345 compounds of formula Iab wherein T1 is N, T2 is CR⁴ᵉ, T3 is N, T4 is CR⁴ᶠ and the values of R8, R⁴ᵉ and R⁴ᶠ are given in Table 2.

Table CDXXIX provides 345 compounds of formula Iac wherein T1 is N, T2 is CR⁴ᵉ, T3 is N, T4 is CR⁴ᶠ and the values of R8, R⁴ᵉ and R⁴ᶠ are given in Table 2.

Table CDXXX provides 345 compounds of formula Iad wherein T1 is N, T2 is CR⁴ᵉ, T3 is N, T4 is CR⁴ᶠ and the values of R8, R⁴ᵉ and R⁴ᶠ are given in Table 2.

Table CDXXXI provides 345 compounds of formula Iae wherein T1 is N, T2 is CR⁴ᵉ, T3 is N, T4 is CR⁴ᶠ and the values of R8, R⁴ᵉ and R⁴ᶠ are given in Table 2.

Table CDXXXII provides 345 compounds of formula Iaf wherein T1 is N, T2 is CR⁴ᵉ, T3 is N, T4 is CR⁴ᶠ and the values of R8, R⁴ᵉ and R⁴ᶠ are given in Table 2.

Table CDXXXIII provides 345 compounds of formula Iag wherein T1 is N, T2 is CR⁴ᵉ, T3 is N, T4 is CR⁴ᶠ and the values of R8, R⁴ᵉ and R⁴ᶠ are given in Table 2.

Table CDXXXIV provides 345 compounds of formula Iah wherein T1 is N, T2 is CR⁴ᵉ, T3 is N, T4 is CR⁴ᶠ and the values of R8, R⁴ᵉ and R⁴ᶠ are given in Table 2.

Table CDXXXV provides 345 compounds of formula Iai wherein T1 is N, T2 is CR⁴ᵉ, T3 is N, T4 is CR⁴ᶠ and the values of R8, R⁴ᵉ and R⁴ᶠ are given in Table 2.

Table CDXXXVI provides 345 compounds of formula Iaj wherein T1 is N, T2 is CR⁴ᵉ, T3 is N, T4 is CR⁴ᶠ and the values of R8, R⁴ᵉ and R⁴ᶠ are given in Table 2.

Table CDXXXVII provides 345 compounds of formula Iak wherein T1 is N, T2 is CR⁴ᵉ, T3 is N, T4 is CR⁴ᶠ and the values of R8, R⁴ᵉ and R⁴ᶠ are given in Table 2.

Table CDXXXVIII provides 345 compounds of formula Ial wherein T1 is N, T2 is CR⁴ᵉ, T3 is N, T4 is CR⁴ᶠ and the values of R8, R⁴ᵉ and R⁴ᶠ are given in Table 2.

Table CDXXXIX provides 345 compounds of formula Iam wherein T1 is N, T2 is CR⁴ᵉ, T3 is N, T4 is CR⁴ᶠ and the values of R8, R⁴ᵉ and R⁴ᶠ are given in Table 2.

Table CDXL provides 345 compounds of formula Ian wherein T1 is N, T2 is CR⁴ᵉ, T3 is N, T4 is CR⁴ᶠ and the values of R8, R⁴ᵉ and R⁴ᶠ are given in Table 2.

Table CDXLI provides 345 compounds of formula Iao wherein T1 is N, T2 is CR⁴ᵉ, T3 is N, T4 is CR⁴ᶠ and the values of R8, R⁴ᵉ and R⁴ᶠ are given in Table 2.

Table CDXLII provides 345 compounds of formula Iap wherein T1 is N, T2 is CR⁴ᵉ, T3 is N, T4 is CR⁴ᶠ and the values of R8, R⁴ᵉ and R⁴ᶠ are given in Table 2.

Table CDXLIII provides 345 compounds of formula Iaq wherein T1 is N, T2 is $CR^{4e}$, T3 is N, T4 is $CR^{4f}$ and the values of R8, $R^{4e}$ and $R^{4f}$ are given in Table 2.

Table CDXLIV provides 345 compounds of formula Iar wherein T1 is N, T2 is $CR^{4e}$, T3 is N, T4 is $CR^{4f}$ and the values of R8, $R^{4e}$ and $R^{4f}$ are given in Table 2.

Table CDXLV provides 345 compounds of formula Ias wherein T1 is N, T2 is $CR^{4e}$, T3 is N, T4 is $CR^{4f}$ and the values of R8, $R^{4e}$ and $R^{4f}$ are given in Table 2.

Table CDXLVI provides 345 compounds of formula Iat wherein T1 is N, T2 is $CR^{4e}$, T3 is N, T4 is $CR^{4f}$ and the values of R8, $R^{4e}$ and $R^{4f}$ are given in Table 2.

Table CDXLVII provides 345 compounds of formula Iau wherein T1 is N, T2 is $CR^{4e}$, T3 is N, T4 is $CR^{4f}$ and the values of R8, $R^{4e}$ and $R^{4f}$ are given in Table 2.

Table CDXLVIII provides 345 compounds of formula Iav wherein T1 is N, T2 is $CR^{4e}$, T3 is N, T4 is $CR^{4f}$ and the values of R8, $R^{4e}$ and $R^{4f}$ are given in Table 2.

Table CDIL provides 345 compounds of formula Iaw wherein T1 is N, T2 is $CR^{4e}$, T3 is N, T4 is $CR^{4f}$ and the values of R8, $R^{4e}$ and $R^{4f}$ are given in Table 2.

Table CDL provides 345 compounds of formula Iax wherein T1 is N, T2 is $CR^{4e}$, T3 is N, T4 is $CR^{4f}$ and the values of R8, $R^{4e}$ and $R^{4f}$ are given in Table 2.

Table CDLI provides 345 compounds of formula wherein T1 is N, T2 is $CR^{4e}$, T3 is N, T4 is $CR^{4f}$ and the values of R8, $R^{4e}$ and $R^{4f}$ are given in Table 2.

Table CDLII provides 345 compounds of formula Iaz wherein T1 is N, T2 is $CR^{4e}$, T3 is N, T4 is $CR^{4f}$ and the values of R8, $R^{4e}$ and $R^{4f}$ are given in Table 2.

Table CDLIII provides 345 compounds of formula Iba wherein T1 is N, T2 is $CR^{4e}$, T3 is N, T4 is $CR^{4f}$ and the values of R8, $R^{4e}$ and $R^{4f}$ are given in Table 2.

Table CDLIV provides 345 compounds of formula Ibb wherein T1 is N, T2 is $CR^{4}$, T3 is N, T4 is $CR^{4f}$ and the values of R8, $R^{4e}$ and $R^{4f}$ are given in Table 2.

Table CDLV provides 345 compounds of formula Ibc wherein T1 is N, T2 is $CR^{4e}$, T3 is N, T4 is $CR^{4f}$ and the values of R8, $R^{4e}$ and $R^{4f}$ are given in Table 2.

Table CDLVI provides 345 compounds of formula Ibd wherein T1 is N, T2 is $CR^{4e}$, T3 is N, T4 is $CR^{4f}$ and the values of R8, $R^{4e}$ and $R^{4f}$ are given in Table 2.

Table CDLVII provides 345 compounds of formula Ibe wherein T1 is N, T2 is $CR^{4e}$, T3 is N, T4 is $CR^{4f}$ and the values of R8, $R^{4e}$ and $R^{4f}$ are given in Table 2.

Table CDLVIII provides 345 compounds of formula Ibf wherein T1 is N, T2 is $CR^{4e}$, T3 is N, T4 is $CR^{4f}$ and the values of R8, $R^{4e}$ and $R^{4f}$ are given in Table 2.

Table CDLIX provides 345 compounds of formula Ibg wherein T1 is N, T2 is $CR^{4e}$, T3 is N, T4 is $CR^{4f}$ and the values of R8, $R^{4e}$ and $R^{4f}$ are given in Table 2.

Table CDLX provides 345 compounds of formula Ibh wherein T1 is N, T2 is $CR^{4e}$, T3 is N, T4 is $CR^{4f}$ and the values of R8, $R^{4e}$ and $R^{4f}$ are given in Table 2.

Table CDLXI provides 345 compounds of formula Ibi wherein T1 is N, T2 is $CR^{4e}$, T3 is N, T4 is $CR^{4f}$ and the values of R8, $R^{4e}$ and $R^{4f}$ are given in Table 2.

Table CDLXII provides 345 compounds of formula Ibj wherein T1 is N, T2 is $CR^{4e}$, T3 is N, T4 is $CR^{4f}$ and the values of R8, $R^{4e}$ and $R^{4f}$ are given in Table 2.

Table CDLXIII provides 345 compounds of formula Ibk wherein T1 is N, T2 is $CR^{4e}$, T3 is N, T4 is $CR^{4f}$ and the values of R8, $R^{4e}$ and $R^{4f}$ are given in Table 2.

Table CDLXIV provides 345 compounds of formula Ibl wherein T1 is N, T2 is $CR^{4e}$, T3 is N, T4 is $CR^{4f}$ and the values of R8, $R^{4e}$ and $R^{4f}$ are given in Table 2.

Table CDLXV provides 345 compounds of formula Ibm wherein T1 is N, T2 is $CR^{4e}$, T3 is N, T4 is $CR^{4f}$ and the values of R8, $R^{4e}$ and $R^{4f}$ are given in Table 2.

Table CDLXVI provides 345 compounds of formula Ibn wherein T1 is N, T2 is $CR^{4e}$, T3 is N, T4 is $CR^{4f}$ and the values of R8, $R^{4e}$ and $R^{4f}$ are given in Table 2.

Table CDLXVII provides 345 compounds of formula Ibo wherein T1 is N, T2 is $CR^{4e}$, T3 is N, T4 is $CR^{4f}$ and the values of R8, $R^{4e}$ and $R^{4f}$ are given in Table 2.

Table DI provides 345 compounds of formula Ia wherein T1 is $CR^{4e}$, T2 is N, T3 is $CR^{4f}$, T4 is N and the values of $R^8$, $R^{4e}$ and $R^{4f}$ are given in Table 2.

Table DII provides 345 compounds of formula Ib wherein T1 is $CR^{4e}$, T2 is N, T3 is $CR^{4f}$, T4 is N and the values of R8, $R^{4e}$ and $R^{4f}$ are given in Table 2.

Table DIII provides 345 compounds of formula Ic wherein T1 is $CR^{4e}$, T2 is N, T3 is $CR^{4f}$, T4 is N and the values of R8, $R^{4e}$ and $R^{4f}$ are given in Table 2.

Table DIV provides 345 compounds of formula Id wherein T1 is $CR^{4e}$, T2 is N, T3 is $CR^{4f}$, T4 is N and the values of R8, $R^{4e}$ and $R^{4f}$ are given in Table 2.

Table DV provides 345 compounds of formula Ie wherein T1 is $CR^{4e}$, T2 is N, T3 is $CR^{4f}$, T4 is N and the values of R8, $R^{4e}$ and $R^{4f}$ are given in Table 2.

Table DVI provides 345 compounds of formula If wherein T1 is $CR^{4e}$, T2 is N, T3 is $CR^{4f}$, T4 is N and the values of R8, $R^{4e}$ and $R^{4f}$ are given in Table 2.

Table DVII provides 345 compounds of formula Ig wherein T1 is $CR^{4e}$, T2 is N, T3 is $CR^{4f}$, T4 is N and the values of R8, $R^{4e}$ and $R^{4f}$ are given in Table 2.

Table DVIII provides 345 compounds of formula Ih wherein T1 is $CR^{4e}$, T2 is N, T3 is $CR^{4f}$, T4 is N and the values of R8, $R^{4e}$ and $R^{4f}$ are given in Table 2.

Table DIX provides 345 compounds of formula Ii wherein T1 is $CR^{4e}$, T2 is N, T3 is $CR^{4f}$, T4 is N and the values of R8, $R^{4e}$ and $R^{4f}$ are given in Table 2.

Table DX provides 345 compounds of formula Ij wherein T1 is $CR^{4e}$, T2 is N, T3 is $CR^{4f}$, T4 is N and the values of R8, $R^{4e}$ and $R^{4f}$ are given in Table 2.

Table DXI provides 345 compounds of formula Ik wherein T1 is $CR^{4e}$, T2 is N, T3 is $CR^{4f}$, T4 is N and the values of R8, $R^{4e}$ and $R^{4f}$ are given in Table 2.

Table DXII provides 345 compounds of formula Il wherein T1 is $CR^{4e}$, T2 is N, T3 is $CR^{4f}$, T4 is N and the values of R8, $R^{4e}$ and $R^{4f}$ are given in Table 2.

Table DXIII provides 345 compounds of formula Im wherein T1 is $CR^{4e}$, T2 is N, T3 is $CR^{4f}$, T4 is N and the values of R8, $R^{4e}$ and $R^{4f}$ are given in Table 2.

Table DXIV provides 345 compounds of formula In wherein T1 is $CR^{4e}$, T2 is N, T3 is $CR^{4f}$, T4 is N and the values of R8, $R^{4e}$ and $R^{4f}$ are given in Table 2.

Table DXV provides 345 compounds of formula Io wherein T1 is $CR^{4e}$, T2 is N, T3 is $CR^{4f}$, T4 is N and the values of R8, $R^{4e}$ and $R^{4f}$ are given in Table 2.

Table DXVI provides 345 compounds of formula Ip wherein T1 is $CR^{4e}$, T2 is N, T3 is $CR^{4f}$, T4 is N and the values of R8, $R^{4e}$ and $R^{4f}$ are given in Table 2.

Table DXVII provides 345 compounds of formula Iq wherein T1 is $CR^{4e}$, T2 is N, T3 is $CR^{4f}$, T4 is N and the values of R8, $R^{4e}$ and $R^{4f}$ are given in Table 2.

Table DXVIII provides 345 compounds of formula Ir wherein T1 is $CR^{4e}$, T2 is N, T3 is $CR^{4f}$, T4 is N and the values of R8, $R^4$ and $R^{4f}$ are given in Table 2.

Table DXIX provides 345 compounds of formula Is wherein T1 is $CR^{4e}$, T2 is N, T3 is $CR^{4f}$, T4 is N and the values of R8, $R^{4e}$ and $R^{4f}$ are given in Table 2.

Table DXX provides 345 compounds of formula It wherein T1 is $CR^{4e}$, T2 is N, T3 is $CR^{4f}$, T4 is N and the values of R8, $R^{4e}$ and $R^{4f}$ are given in Table 2.

Table DXXI provides 345 compounds of formula Iu wherein T1 is $CR^{4e}$, T2 is N, T3 is $CR^{4f}$, T4 is N and the values of R8, $R^{4e}$ and $R^{4f}$ are given in Table 2.

Table DXXII provides 345 compounds of formula Iv wherein T1 is $CR^{4e}$, T2 is N, T3 is $CR^{4f}$, T4 is N and the values of R8, $R^{4e}$ and $R^{4f}$ are given in Table 2.

Table DXXIII provides 345 compounds of formula Iw wherein T1 is $CR^{4e}$, T2 is N, T3 is $CR^{4f}$, T4 is N and the values of R8, $R^{4e}$ and $R^{4f}$ are given in Table 2.

Table DXXIV provides 345 compounds of formula Ix wherein T1 is $CR^{4e}$, T2 is N, T3 is $CR^{4f}$, T4 is N and the values of R8, $R^{4e}$ and $R^{4f}$ are given in Table 2.

Table DXXV provides 345 compounds of formula Iy wherein T1 is $CR^{4e}$, T2 is N, T3 is $CR^{4f}$, T4 is N and the values of R8, $R^{4e}$ and $R^{4f}$ are given in Table 2.

Table DXXVI provides 345 compounds of formula Iz wherein T1 is $CR^{4e}$, T2 is N, T3 is $CR^{4f}$, T4 is N and the values of R8, $R^{4e}$ and $R^{4f}$ are given in Table 2.

Table DXXVII provides 345 compounds of formula Iaa wherein T1 is $CR^{4e}$, T2 is N, T3 is $CR^{4f}$, T4 is N and the values of R8, $R^{4e}$ and $R^{4f}$ are given in Table 2.

Table DXXVIII provides 345 compounds of formula Iab wherein T1 is $CR^{4e}$, T2 is N, T3 is $CR^{4f}$, T4 is N and the values of R8, $R^{4e}$ and $R^{4f}$ are given in Table 2.

Table DXXIX provides 345 compounds of formula Iac wherein T1 is $CR^{4e}$, T2 is N, T3 is $CR^{4f}$, T4 is N and the values of R8, $R^{4e}$ and $R^{4f}$ are given in Table 2.

Table DXXX provides 345 compounds of formula Iad wherein T1 is $CR^{4e}$, T2 is N, T3 is $CR^{4f}$, T4 is N and the values of R8, $R^{4e}$ and $R^{4f}$ are given in Table 2.

Table DXXXI provides 345 compounds of formula Iae wherein T1 is $CR^{4e}$, T2 is N, T3 is $CR^{4f}$, T4 is N and the values of R8, $R^{4e}$ and $R^{4f}$ are given in Table 2.

Table DXXXII provides 345 compounds of formula Iaf wherein T1 is $CR^{4e}$, T2 is N, T3 is $CR^{4f}$, T4 is N and the values of R8, $R^{4e}$ and $R^{4f}$ are given in Table 2.

Table DXXXIII provides 345 compounds of formula Iag wherein T1 is $CR^{4e}$, T2 is N, T3 is $CR^{4f}$, T4 is N and the values of R8, $R^{4e}$ and $R^{4f}$ are given in Table 2.

Table DXXXIV provides 345 compounds of formula Iah wherein T1 is $CR^{4e}$, T2 is N, T3 is $CR^{4f}$, T4 is N and the values of R8, $R^{4e}$ and $R^{4f}$ are given in Table 2.

Table DXXXV provides 345 compounds of formula Iai wherein T1 is $CR^{4e}$, T2 is N, T3 is $CR^{4f}$, T4 is N and the values of R8, $R^{4e}$ and $R^{4f}$ are given in Table 2.

Table DXXXVI provides 345 compounds of formula Iaj wherein T1 is $CR^{4e}$, T2 is N, T3 is $CR^{4f}$, T4 is N and the values of R8, $R^{4e}$ and $R^{4f}$ are given in Table 2.

Table DXXXVII provides 345 compounds of formula Iak wherein T1 is $CR^{4e}$, T2 is N, T3 is $CR^{4f}$, T4 is N and the values of R8, $R^{4e}$ and $R^{4f}$ are given in Table 2.

Table DXXXVIII provides 345 compounds of formula Ial wherein T1 is $CR^{4e}$, T2 is N, T3 is $CR^{4f}$, T4 is N and the values of R8, $R^{4e}$ and $R^{4f}$ are given in Table 2.

Table DXXXIX provides 345 compounds of formula Iam wherein T1 is $CR^{4e}$, T2 is N, T3 is $CR^{4f}$, T4 is N and the values of R8, $R^{4e}$ and $R^{4f}$ are given in Table 2.

Table DXL provides 345 compounds of formula Ian wherein T1 is $CR^{4e}$, T2 is N, T3 is $CR^{4f}$, T4 is N and the values of R8, $R^{4e}$ and $R^{4f}$ are given in Table 2.

Table DXLI provides 345 compounds of formula Iao wherein T1 is $CR^{4e}$, T2 is N, T3 is $CR^{4f}$, T4 is N and the values of R8, $R^{4e}$ and $R^{4f}$ are given in Table 2.

Table DXLII provides 345 compounds of formula Iap wherein T1 is $CR^{4e}$, T2 is N, T3 is $CR^{4f}$, T4 is N and the values of R8, $R^{4e}$ and $R^{4f}$ are given in Table 2.

Table DXLIII provides 345 compounds of formula Iaq wherein T1 is $CR^{4e}$, T2 is N, T3 is $CR^{4f}$, T4 is N and the values of R8, $R^{4e}$ and $R^{4f}$ are given in Table 2.

Table DXLIV provides 345 compounds of formula Iar wherein T1 is $CR^{4e}$, T2 is N, T3 is $CR^{4f}$, T4 is N and the values of R8, $R^{4e}$ and $R^{4f}$ are given in Table 2.

Table DXLV provides 345 compounds of formula Ias wherein T1 is $CR^{4e}$, T2 is N, T3 is $CR^{4f}$, T4 is N and the values of R8, $R^{4e}$ and $R^{4f}$ are given in Table 2.

Table DXLVI provides 345 compounds of formula Iat wherein T1 is $CR^{4e}$, T2 is N, T3 is $CR^{4f}$, T4 is N and the values of R8, $R^{4e}$ and $R^{4f}$ are given in Table 2.

Table DXLVII provides 345 compounds of formula Iau wherein T1 is $CR^{4e}$, T2 is N, T3 is $CR^{4f}$, T4 is N and the values of R8, $R^4$ and $R^{4f}$ are given in Table 2.

Table DXLVIII provides 345 compounds of formula Iav wherein T1 is $CR^{4e}$, T2 is N, T3 is $CR^{4f}$, T4 is N and the values of R8, $R^{4e}$ and $R^{4f}$ are given in Table 2.

Table DIL provides 345 compounds of formula Iaw wherein T1 is $CR^{4e}$, T2 is N, T3 is $CR^{4f}$, T4 is N and the values of R8, $R^{4e}$ and $R^{4f}$ are given in Table 2.

Table DL provides 345 compounds of formula Iax wherein T1 is $CR^{4e}$, T2 is N, T3 is $CR^{4f}$, T4 is N and the values of R8, $R^{4e}$ and $R^{4f}$ are given in Table 2.

Table DLI provides 345 compounds of formula wherein T1 is $CR^{4e}$, T2 is N, T3 is $CR^{4f}$, T4 is N and the values of R8, $R^{4e}$ and $R^{4f}$ are given in Table 2.

Table DLII provides 345 compounds of formula Iaz wherein T1 is $CR^{4e}$, T2 is N, T3 is $CR^{4f}$, T4 is N and the values of R8, $R^{4e}$ and $R^{4f}$ are given in Table 2.

Table DLIII provides 345 compounds of formula Iba wherein T1 is $CR^{4e}$, T2 is N, T3 is $CR^{4f}$, T4 is N and the values of R8, $R^{4e}$ and $R^{4f}$ are given in Table 2.

Table DLIV provides 345 compounds of formula Ibb wherein T1 is $CR^4$, T2 is N, T3 is $CR^{4f}$, T4 is N and the values of R8, $R^{4e}$ and $R^{4f}$ are given in Table 2.

Table DLV provides 345 compounds of formula Ibc wherein T1 is $CR^{4e}$, T2 is N, T3 is $CR^{4f}$, T4 is N and the values of R8, $R^{4e}$ and $R^{4f}$ are given in Table 2.

Table DLVI provides 345 compounds of formula Ibd wherein T1 is $CR^{4e}$, T2 is N, T3 is $CR^{4f}$, T4 is N and the values of R8, $R^{4e}$ and $R^{4f}$ are given in Table 2.

Table DLVII provides 345 compounds of formula Ibe wherein T1 is $CR^{4e}$, T2 is N, T3 is $CR^{4f}$, T4 is N and the values of R8, $R^{4e}$ and $R^{4f}$ are given in Table 2.

Table DLVIII provides 345 compounds of formula Ibf wherein T1 is $CR^{4e}$, T2 is N, T3 is $CR^{4f}$, T4 is N and the values of R8, $R^{4e}$ and $R^{4f}$ are given in Table 2.

Table DLIX provides 345 compounds of formula Ibg wherein T1 is $CR^{4e}$, T2 is N, T3 is $CR^{4f}$, T4 is N and the values of R8, $R^{4e}$ and $R^{4f}$ are given in Table 2.

Table DLX provides 345 compounds of formula Ibh wherein T1 is $CR^{4e}$, T2 is N, T3 is $CR^{4f}$, T4 is N and the values of R8, $R^{4e}$ and $R^{4f}$ are given in Table 2.

Table DLXI provides 345 compounds of formula Ibi wherein T1 is $CR^{4e}$, T2 is N, T3 is $CR^{4f}$, T4 is N and the values of R8, $R^{4e}$ and $R^{4f}$ are given in Table 2.

Table DLXII provides 345 compounds of formula Ibj wherein T1 is $CR^{4e}$, T2 is N, T3 is $CR^{4f}$, T4 is N and the values of R8, $R^{4e}$ and $R^{4f}$ are given in Table 2.

Table DLXIII provides 345 compounds of formula Ibk wherein T1 is $CR^{4e}$, T2 is N, T3 is $CR^{4f}$, T4 is N and the values of R8, $R^{4e}$ and $R^{4f}$ are given in Table 2.

Table DLXIV provides 345 compounds of formula Ibl wherein T1 is $CR^{4e}$, T2 is N, T3 is $CR^{4f}$, T4 is N and the values of R8, $R^{4e}$ and $R^{4f}$ are given in Table 2.

Table DLXV provides 345 compounds of formula Ibm wherein T1 is $CR^{4e}$, T2 is N, T3 is $CR^{4f}$, T4 is N and the values of R8, $R^{4e}$ and $R^{4f}$ are given in Table 2.

Table DLXVI provides 345 compounds of formula Ibn wherein T1 is $CR^{4e}$, T2 is N, T3 is $CR^{4f}$, T4 is N and the values of R8, $R^{4e}$ and $R^{4f}$ are given in Table 2.

Table DLXVII provides 345 compounds of formula Ibo wherein T1 is $CR^{4e}$, T2 is N, T3 is $CR^{4f}$, T4 is N and the values of R8, $R^{4e}$ and $R^{4f}$ are given in Table 2.

Table DCI provides 345 compounds of formula Ica

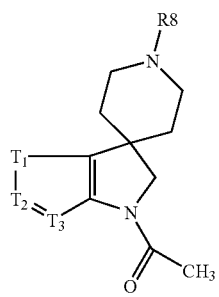

(Iaa)

wherein T1 is S, T2 is $CR^{4e}$, T3 is $CR^{4f}$ and the values of $R^8$, $R^{4e}$ and $R^{4f}$ are given in Table 2.

Table DCII provides 345 compounds of formula Icb

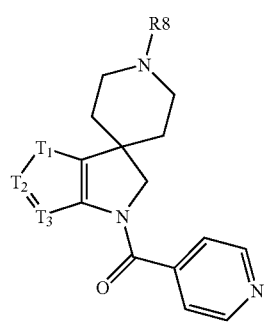

(Icb)

wherein T1 is S, T2 is $CR^{4e}$, T3 is $CR^{4f}$ and the values of $R^8$, $R^{4e}$ and $R^{4f}$ are given in Table 2.

Table DCIII provides 345 compounds of formula Icc

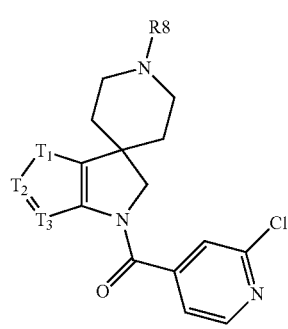

(Icc)

wherein T1 is S, T2 is $CR^{4e}$, T3 is $CR^{4f}$ and the values of $R^8$, $R^{4e}$ and $R^{4f}$ are given in Table 2.

Table DCIV provides 345 compounds of formula Icd

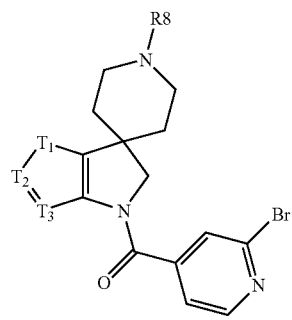

(Icd)

wherein T1 is S, T2 is $CR^{4e}$, T3 is $CR^{4f}$ and the values of $R^8$, $R^{4e}$ and $R^{4f}$ are given in Table 2.

Table DCV provides 345 compounds of formula Ice

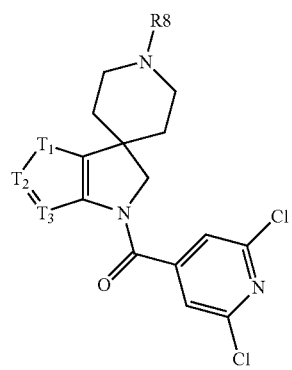

(Ice)

wherein T1 is S, T2 is $CR^{4e}$, T3 is $CR^{4f}$ and the values of $R^8$, $R^{4e}$ and $R^{4f}$ are given in Table 2.

Table DCVI provides 345 compounds of formula Icf (Icf)

wherein T1 is S, T2 is $CR^{4e}$, T3 is $CR^{4f}$ and the values of $R^8$, $R^{4e}$ and $R^{4f}$ are given in Table 2.

Table DCLVII provides 345 compounds of formula Icg

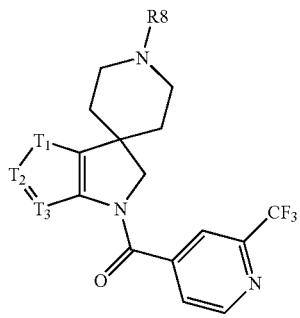

wherein T1 is S, T2 is $CR^{4e}$, T3 is $CR^{4f}$ and the values of $R^8$, $R^{4e}$ and $R^{4f}$ are given in Table 2.

Table DCVIII provides 345 compounds of formula Ich

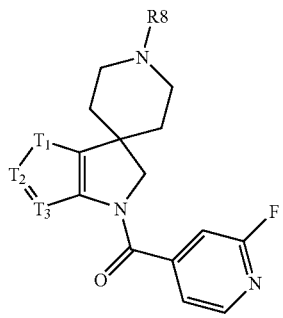

wherein T1 is S, T2 is $CR^{4e}$, T3 is $CR^{4e}$ and the values of $R^8$, $R^{4e}$ and $R^{4f}$ are given in Table 2.

Table DCIX provides 345 compounds of formula Ici

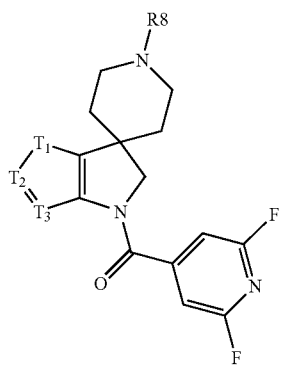

wherein T1 is S, T2 is $CR^{4e}$, T3 is $CR^{4f}$ and the values of $R^8$, $R^{4e}$ and $R^{4f}$ are given in Table 2.

Table DCLX provides 345 compounds of formula Icj

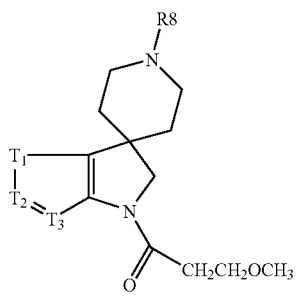

wherein T1 is S, T2 is $CR^{4e}$, T3 is $CR^{4f}$ and the values of $R^8$, $R^{4e}$ and $R^{4f}$ are given in Table 2.

Table DCXI provides 345 compounds of formula Ick

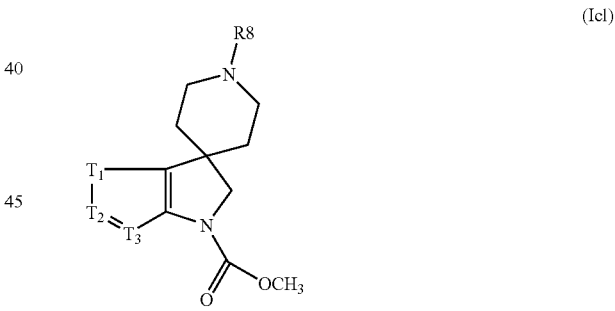

wherein T1 is S, T2 is $CR^{4e}$, T3 is $CR^{4f}$ and the values of $R^8$, $R^{4e}$ and $R^{4f}$ are given in Table 2.

Table DCXII provides 345 compounds of formula Icl

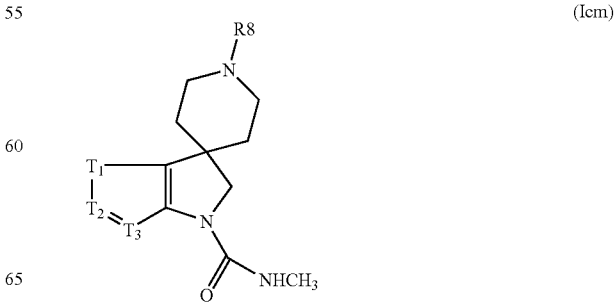

wherein T1 is S, T2 is $CR^{4e}$, T3 is $CR^{4f}$ and the values of $R^8$, $R^{4e}$ and $R^{4f}$ are given in Table 2.

Table DCXIII provides 345 compounds of formula Icm (Icm)

wherein T1 is S, T2 is CR$^{4e}$, T3 is CR$^{4f}$ and the values of R$^8$, R$^{4e}$ and R$^{4f}$ are given in Table 2.

Table DCXIV provides 345 compounds of formula Icn

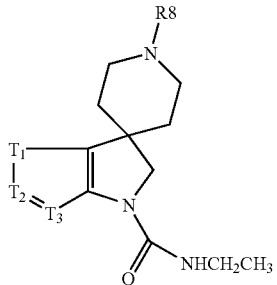

(Icn)

wherein T1 is S, T2 is CR$^{4e}$, T3 is CR$^{4f}$ and the values of R$^8$, R$^{4e}$ and R$^{4f}$ are given in Table 2.

Table DCXV provides 345 compounds of formula Ico

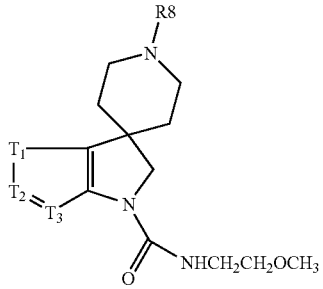

(Ico)

wherein T1 is S, T2 is CR$^{4e}$, T3 is CR$^{4f}$ and the values of R$^8$, R$^{4e}$ and R$^{4f}$ are given in Table 2.

Table DCXVI provides 345 compounds of formula Icp

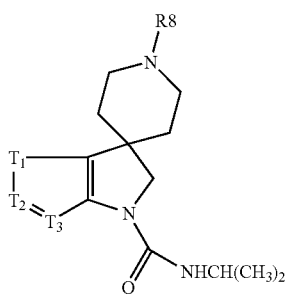

(Icp)

wherein T1 is S, T2 is CR$^{4e}$, T3 is CR$^{4f}$ and the values of R$^8$, R$^{4e}$ and R$^{4f}$ are given in Table 2.

Table DCXVII provides 345 compounds of formula Icq

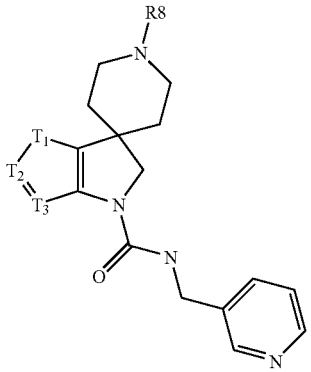

(Icq)

wherein T1 is S, T2 is CR$^{4e}$, T3 is CR$^{4f}$ and the values of R$^8$, R$^{4e}$ and R$^{4f}$ are given in Table 2.

Table DCXVIII provides 345 compounds of formula Icr

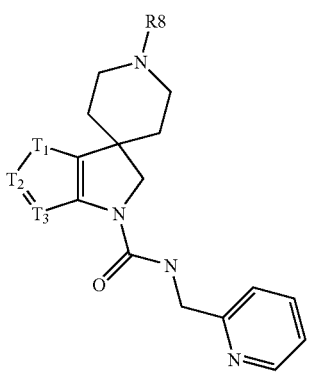

(Icr)

wherein T1 is S, T2 is CR$^{4e}$, T3 is CR$^{4f}$ and the values of R$^8$, R$^{4e}$ and R$^{4f}$ are given in Table 2.

Table DCXIX provides 345 compounds of formula Ics

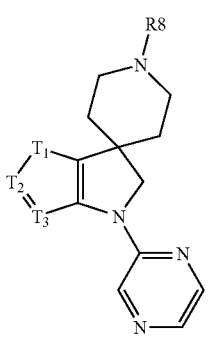

(Ics)

wherein T1 is S, T2 is CR$^{4e}$, T3 is CR$^{4f}$ and the values of R$^8$, R$^{4e}$ and R$^{4f}$ are given in Table 2.

Table DCXX provides 345 compounds of formula Ict

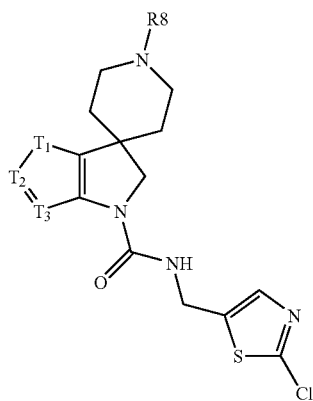
(Ict)

wherein T1 is S, T2 is CR$^{4e}$, T3 is CR$^{4f}$ and the values of R$^8$, R$^{4e}$ and R$^{4f}$ are given in Table 2.

Table DCXXI provides 345 compounds of formula Icu

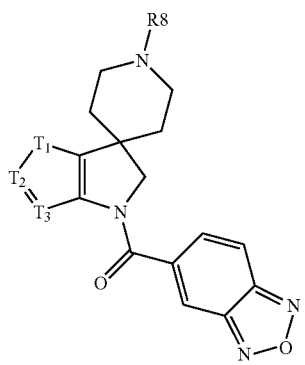
(Icu)

wherein T1 is S, T2 is CR$^{4e}$, T3 is CR$^{4f}$ and the values of R$^8$, R$^{4e}$ and R$^{4f}$ are given in Table 2.

Table DCXXIII provides 345 compounds of formula Icv

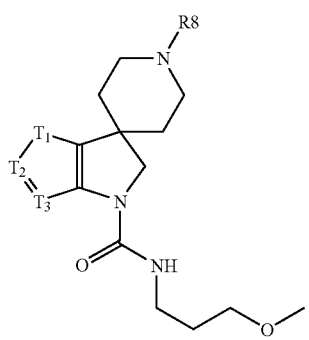
(Icv)

wherein T1 is S, T2 is CR$^{4e}$, T3 is CR$^{4f}$ and the values of R$^8$, R$^{4e}$ and R$^{4f}$ are given in Table 2.

Table DCXXIII provides 345 compounds of formula Icw

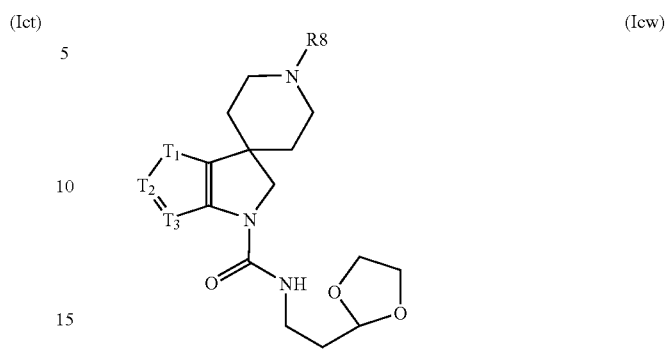
(Icw)

wherein T1 is S, T2 is CR$^{4e}$, T3 is CR$^{4f}$ and the values of R$^8$, R$^{4e}$ and R$^{4f}$ are given in Table 2.

Table DCXXIV provides 345 compounds of formula Icx

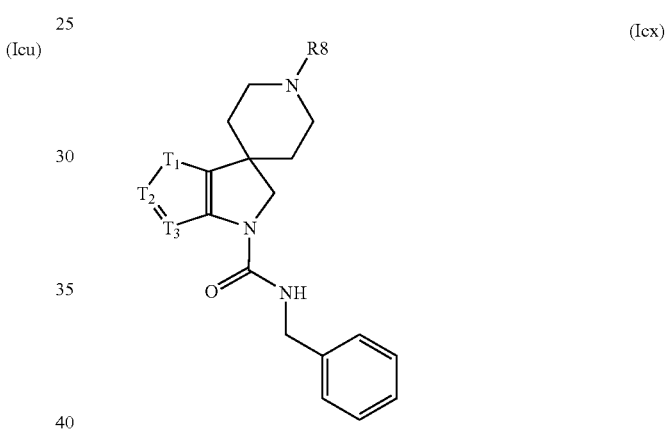
(Icx)

wherein T1 is S, T2 is CR$^{4e}$, T3 is CR$^{4f}$ and the values of R$^8$, R$^{4e}$ and R$^{4f}$ are given in Table 2.

Table DCXXV provides 345 compounds of formula Icy

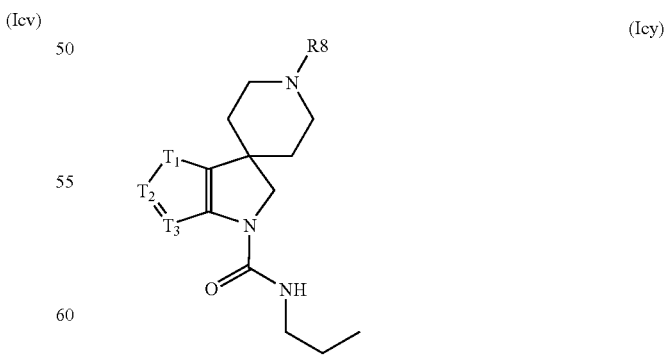
(Icy)

wherein T1 is S, T2 is CR$^{4e}$, T3 is CR$^{4f}$ and the values of R$^8$, R$^{4e}$ and R$^{4f}$ are given in Table 2.

Table DCXXVI provides 345 compounds of formula Icz

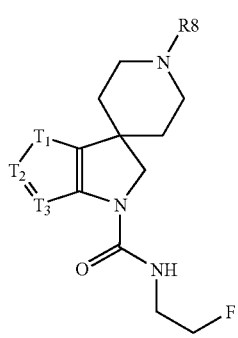
(Icz)

wherein T1 is S, T2 is $CR^{4e}$, T3 is $CR^{4f}$ and the values of $R^8$, $R^{4e}$ and $R^{4f}$ are given in Table 2.

Table DCXXVII provides 345 compounds of formula Ida

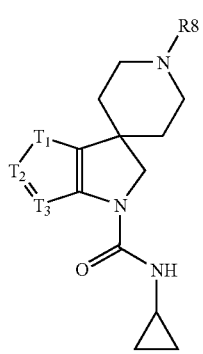
(Ida)

wherein T1 is S, T2 is $CR^{4e}$, T3 is $CR^{4f}$ and the values of $R^8$, $R^{4e}$ and $R^{4f}$ are given in Table 2.

Table DCXXVIII provides 345 compounds of formula Idb

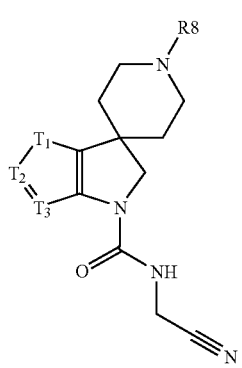
(Idb)

wherein T1 is S, T2 is $CR^{4e}$, T3 is $CR^{4f}$ and the values of $R^8$, $R^{4e}$ and $R^{4f}$ are given in Table 2.

Table DCXXIX provides 345 compounds of formula Idc

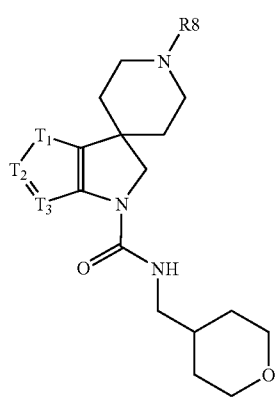
(Idc)

wherein T1 is S, T2 is $CR^{4e}$, T3 is $CR^{4f}$ and the values of $R^8$, $R^{4e}$ and $R^{4f}$ are given in Table 2.

Table DCXXX provides 345 compounds of formula Idd

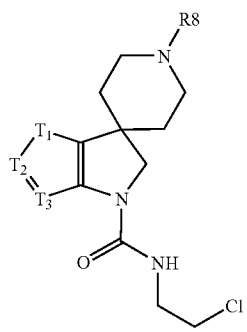
(Idd)

wherein T1 is S, T2 is $CR^{4e}$, T3 is $CR^{4f}$ and the values of $R^8$, $R^{4e}$ and $R^{4f}$ are given in Table 2.

Table DCXXXI provides 345 compounds of formula Ide

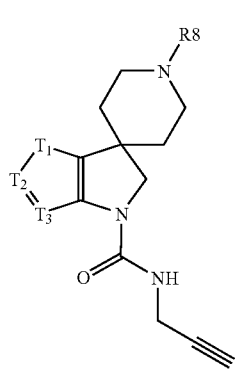
(Ide)

wherein T1 is S, T2 is $CR^{4e}$, T3 is $CR^{4f}$ and the values of $R^8$, $R^{4e}$ and $R^{4f}$ are given in Table 2.

Table DCXXXII provides 345 compounds of formula Idf

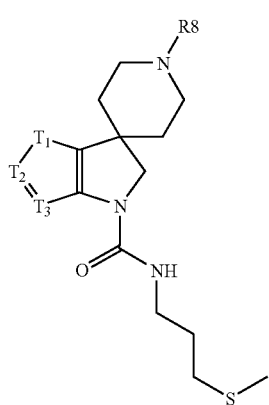
(Idf)

wherein T1 is S, T2 is $CR^{4e}$, T3 is $CR^{4f}$ and the values of $R^8$, $R^{4e}$ and $R^{4f}$ are given in Table 2.

Table DCXXXIII provides 345 compounds of formula Idg

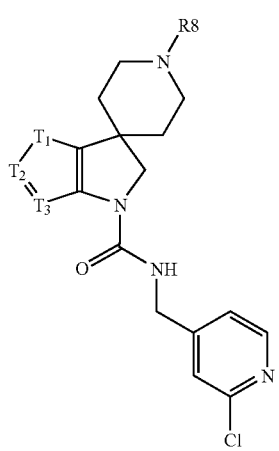
(Idg)

wherein T1 is S, T2 is $CR^{4e}$, T3 is $CR^{4f}$ and the values of $R^8$, $R^{4e}$ and $R^{4f}$ are given in Table 2.

Table DCXXXIV provides 345 compounds of formula Idh

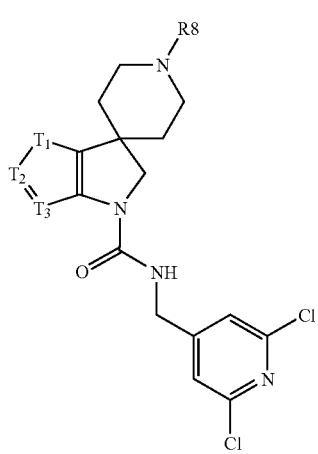
(Idh)

wherein T1 is S, T2 is $CR^{4e}$, T3 is $CR^{4f}$ and the values of $R^8$, $R^{4e}$ and $R^{4f}$ are given in Table 2.

Table DCXXXV provides 345 compounds of formula Idi

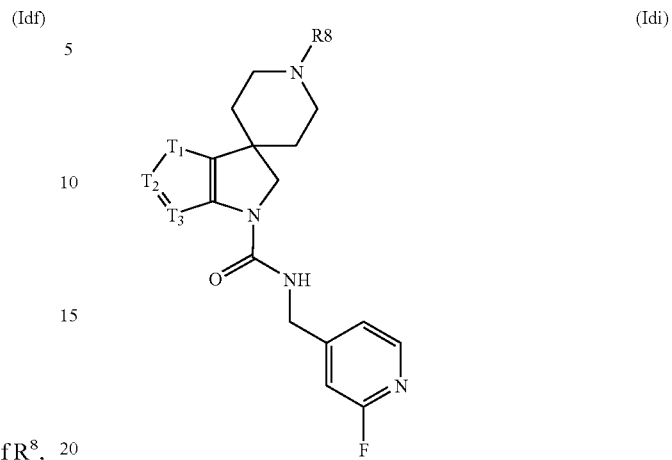
(Idi)

wherein T1 is S, T2 is $CR^{4e}$, T3 is $CR^{4f}$ and the values of $R^8$, $R^{4e}$ and $R^{4f}$ are given in Table 2.

Table DCXXXVI provides 345 compounds of formula Idj

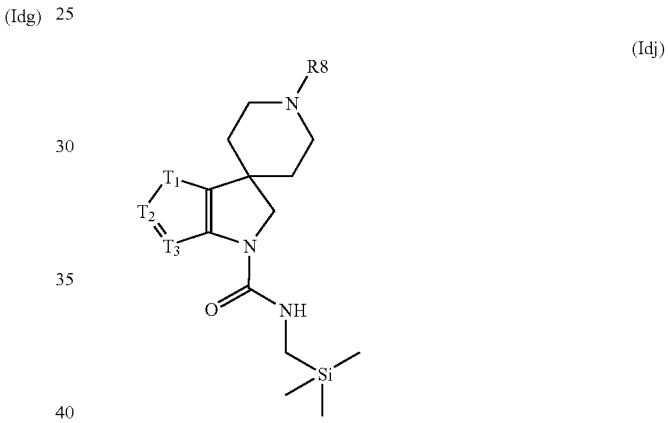
(Idj)

wherein T1 is S, T2 is $CR^{4e}$, T3 is $CR^{4f}$ and the values of $R^8$, $R^{4e}$ and $R^{4f}$ are given in Table 2.

Table DCXXXVII provides 345 compounds of formula Idk

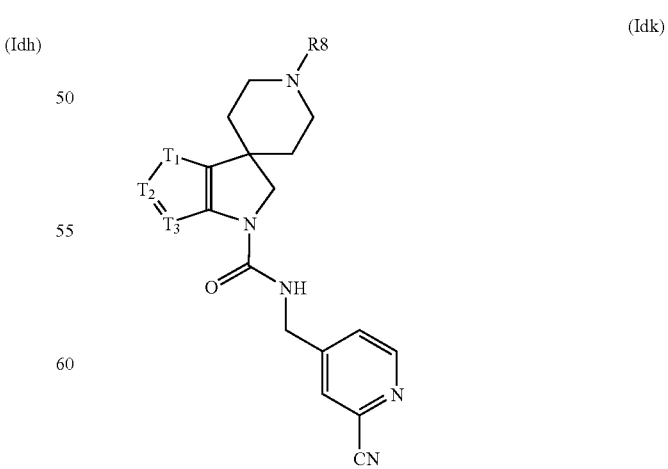
(Idk)

wherein T1 is S, T2 is $CR^{4e}$, T3 is $CR^{4f}$ and the values of $R^8$, $R^{4e}$ and $R^{4f}$ are given in Table 2.

Table DCXXXVIII provides 345 compounds of formula Idl

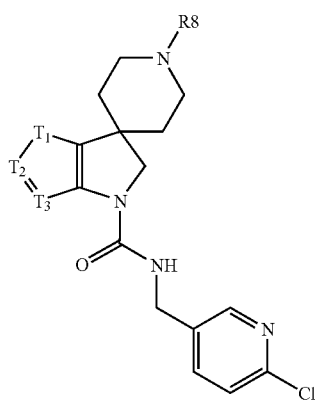

(Idl)

wherein T1 is S, T2 is CR$^{4e}$, T3 is CR$^{4f}$ and the values of R$^8$, R$^{4e}$ and R$^{4f}$ are given in Table 2.

Table DCXXXIX provides 345 compounds of formula Idm

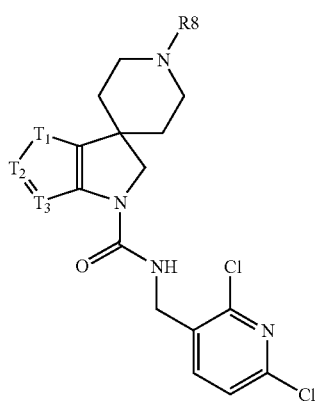

(Idm)

wherein T1 is S, T2 is CR$^{4e}$, T3 is CR$^{4f}$ and the values of R$^8$, R$^{4e}$ and R$^{4f}$ are given in Table 2.

Table DCXLX provides 345 compounds of formula Idn

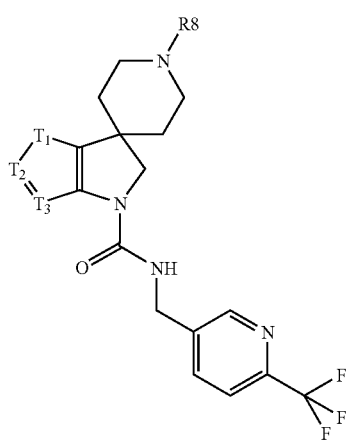

(Idn)

wherein T1 is S, T2 is CR$^{4e}$, T3 is CR$^{4f}$ and the values of R$^8$, R$^{4e}$ and R$^{4f}$ are given in Table 2.

Table DCXLI provides 345 compounds of formula Ido

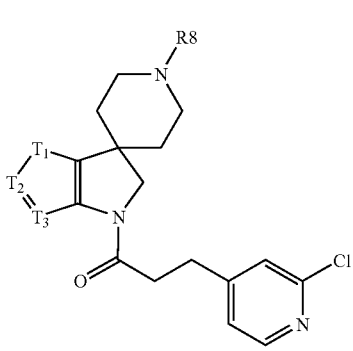

(Ido)

wherein T1 is S, T2 is CR$^{4e}$, T3 is CR$^{4f}$ and the values of R$^8$, R$^{4e}$ and R$^{4f}$ are given in Table 2.

Table DCXLII provides 345 compounds of formula Idp

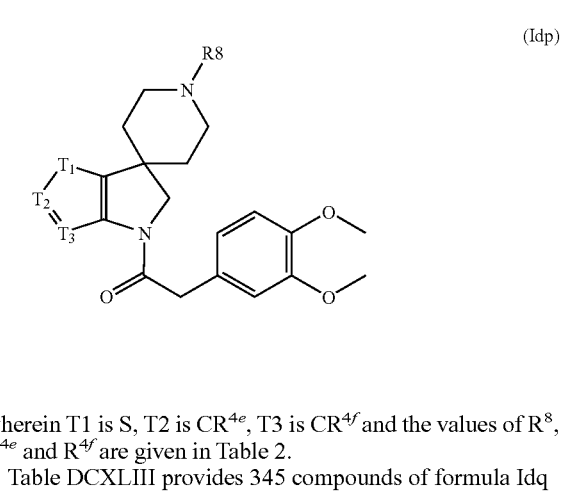

(Idp)

wherein T1 is S, T2 is CR$^{4e}$, T3 is CR$^{4f}$ and the values of R$^8$, R$^{4e}$ and R$^{4f}$ are given in Table 2.

Table DCXLIII provides 345 compounds of formula Idq

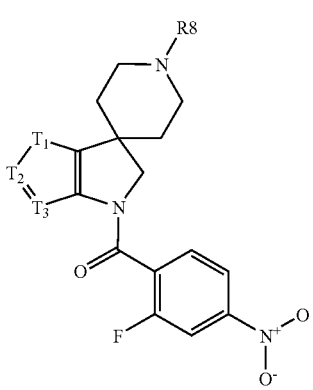

(Idq)

wherein T1 is S, T2 is CR$^{4e}$, T3 is CR$^{4f}$ and the values of R$^8$, R$^{4e}$ and R$^{4f}$ are given in Table 2.

Table DCXLIV provides 345 compounds of formula Idr

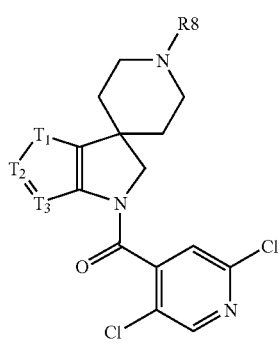

(Idr)

wherein T1 is S, T2 is $CR^{4e}$, T3 is $CR^{4f}$ and the values of $R^8$, $R^{4e}$ and $R^{4f}$ are given in Table 2.

Table DCXLV provides 345 compounds of formula Ids

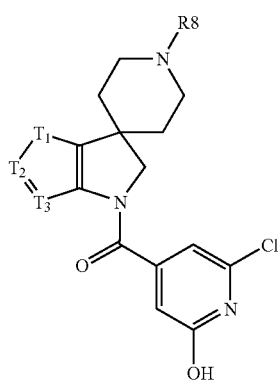

(Ids)

wherein T1 is S, T2 is $CR^{4e}$, T3 is $CR^{4f}$ and the values of $R^8$, $R^{4e}$ and $R^{4f}$ are given in Table 2.

Table DCXLV provides 345 compounds of formula Idt

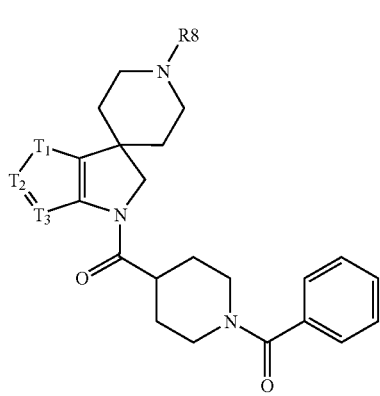

(Idt)

wherein T1 is S, T2 is $CR^{4e}$, T3 is $CR^{4f}$ and the values of $R^8$, $R^{4e}$ and $R^{4f}$ are given in Table 2.

Table DCXLVII provides 345 compounds of formula Idu

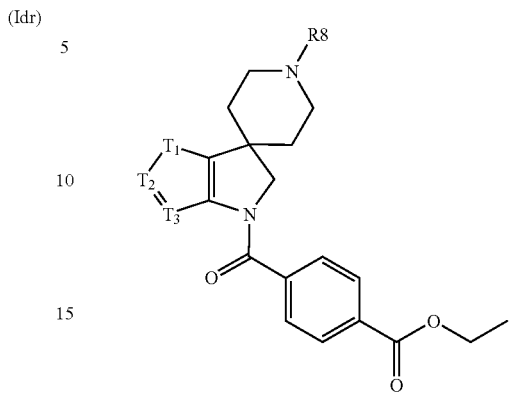

(Idu)

wherein T1 is S, T2 is $CR^{4e}$, T3 is $CR^{4f}$ and the values of $R^8$, $R^{4e}$ and $R^{4f}$ are given in Table 2.

Table DCXLVIII provides 345 compounds of formula Idv

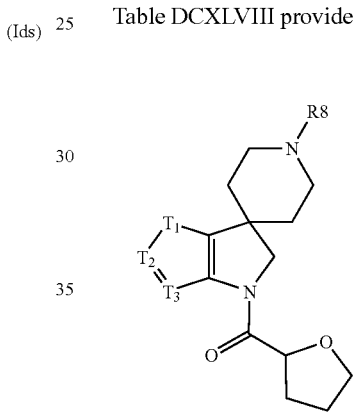

(Idv)

wherein T1 is S, T2 is $CR^{4e}$, T3 is $CR^{4f}$ and the values of $R^8$, $R^{4e}$ and $R^{4f}$ are given in Table 2.

Table DCIL provides 345 compounds of formula Idw

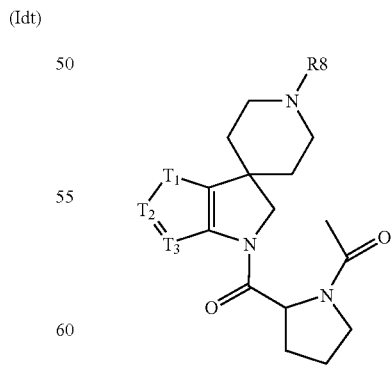

(Idw)

wherein T1 is S, T2 is $CR^{4e}$, T3 is $CR^{4f}$ and the values of $R^8$, $R^{4e}$ and $R^{4f}$ are given in Table 2.

Table DCL provides 345 compounds of formula Idx

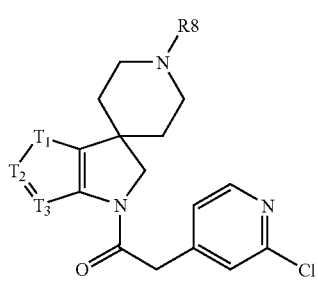
(Idx)

wherein T1 is S, T2 is $CR^{4e}$, T3 is $CR^{4f}$ and the values of $R^8$, $R^{4e}$ and $R^{4f}$ are given in Table 2.

Table DCLI provides 345 compounds of formula Idy

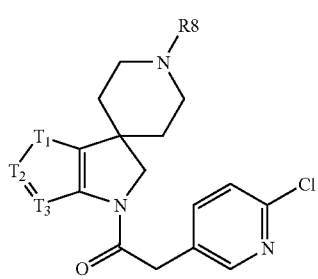
(Idy)

wherein T1 is S, T2 is $CR^{4e}$, T3 is $CR^{4f}$ and the values of $R^8$, $R^{4e}$ and $R^{4f}$ are given in Table 2.

Table DCLII provides 345 compounds of formula Idz

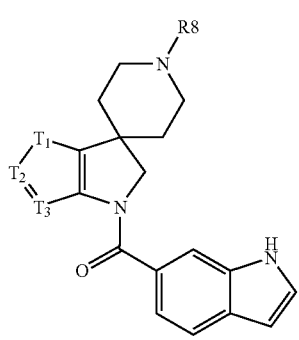
(Idz)

wherein T1 is S, T2 is $CR^{4e}$, T3 is $CR^{4f}$ and the values of $R^8$, $R^{4e}$ and $R^{4f}$ are given in Table 2.

Table DCLIII provides 345 compounds of formula Iea

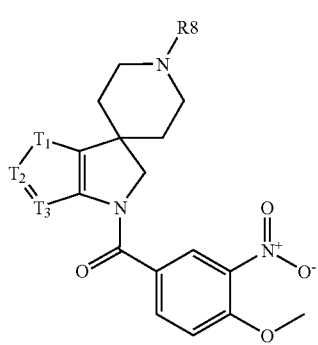
(Iea)

wherein T1 is S, T2 is $CR^{4e}$, T3 is $CR^{4f}$ and the values of $R^8$, $R^{4e}$ and $R^{4f}$ are given in Table 2.

Table DCLIV provides 345 compounds of formula Ieb

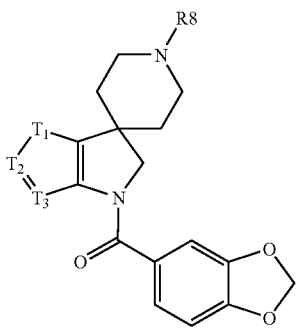
(Ieb)

wherein T1 is S, T2 is $CR^{4e}$, T3 is $CR^{4f}$ and the values of $R^8$, $R^{4e}$ and $R^{4f}$ are given in Table 2.

Table DCLV provides 345 compounds of formula Iec

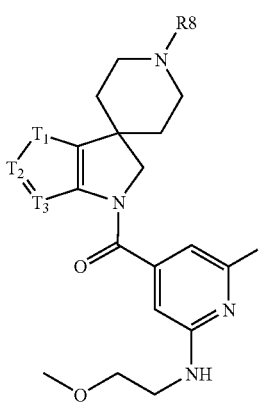
(Iec)

wherein T1 is S, T2 is $CR^{4e}$, T3 is $CR^{4f}$ and the values of $R^8$, $R^{4e}$ and $R^{4f}$ are given in Table 2.

Table DCLVI provides 345 compounds of formula Ied

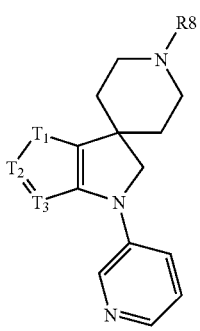
(Ied)

wherein T1 is S, T2 is $CR^{4e}$, T3 is $CR^{4f}$ and the values of $R^8$, $R^{4e}$ and $R^{4f}$ are given in Table 2.

Table DCLVII provides 345 compounds of formula Iee

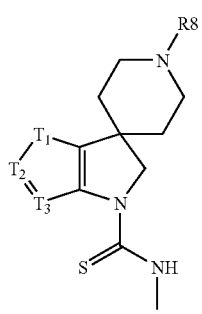

(Iee)

wherein T1 is S, T2 is $CR^{4e}$, T3 is $CR^{4f}$ and the values of $R^8$, $R^{4e}$ and $R^{4f}$ are given in Table 2.

Table DCLVIII provides 345 compounds of formula Ief

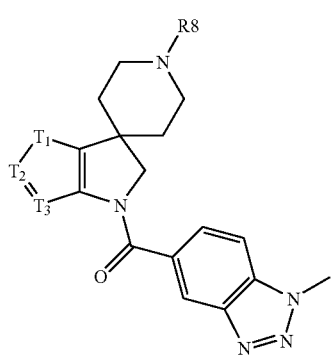

(Ief)

wherein T1 is S, T2 is $CR^{4e}$, T3 is $CR^{4f}$ and the values of $R^8$, $R^{4e}$ and $R^{4f}$ are given in Table 2.

Table DCLIX provides 345 compounds of formula Ieg

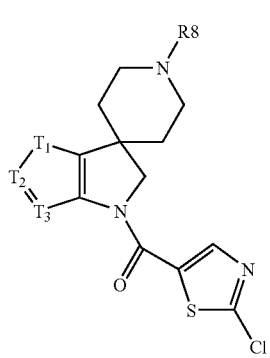

(Ieg)

wherein T1 is S, T2 is $CR^{4e}$, T3 is $CR^{4f}$ and the values of $R^8$, $R^{4e}$ and $R^{4f}$ are given in Table 2.

Table DCLX provides 345 compounds of formula Ieh

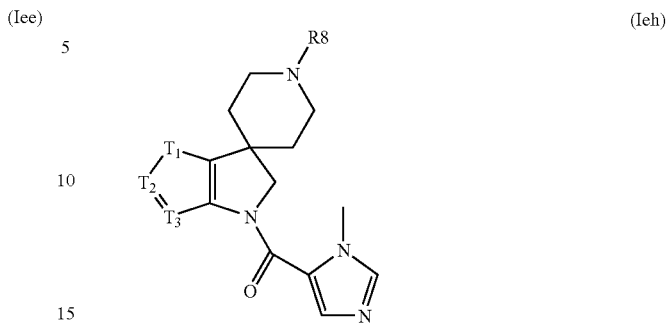

(Ieh)

wherein T1 is S, T2 is $CR^{4e}$, T3 is $CR^{4f}$ and the values of $R^8$, $R^{4e}$ and $R^{4f}$ are given in Table 2.

Table DCLXI provides 345 compounds of formula Iei

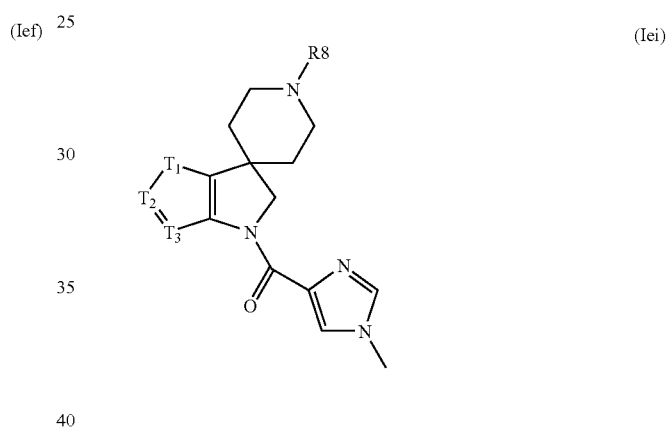

(Iei)

wherein T1 is S, T2 is $CR^{4e}$, T3 is $CR^{4f}$ and the values of $R^8$, $R^{4e}$ and $R^{4f}$ are given in Table 2.

Table DCLXII provides 345 compounds of formula Iej

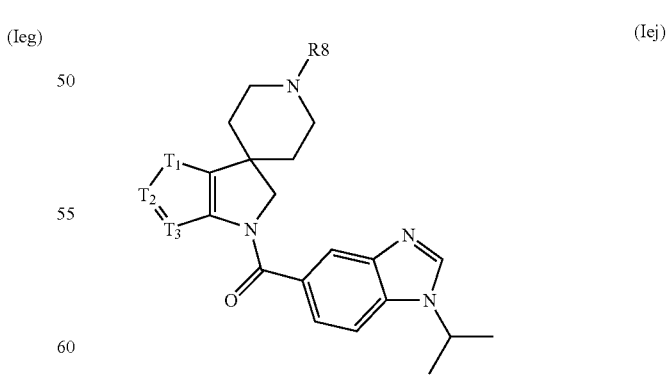

(Iej)

wherein T1 is S, T2 is $CR^{4e}$, T3 is $CR^{4f}$ and the values of $R^8$, $R^{4e}$ and $R^{4f}$ are given in Table 2.

Table DCLXIII provides 345 compounds of formula Iek

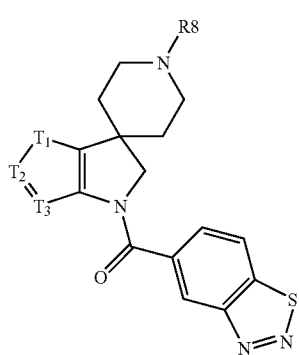

wherein T1 is S, T2 is $CR^{4e}$, T3 is $CR^{4f}$ and the values of $R^8$, $R^{4e}$ and $R^{4f}$ are given in Table 2.

Table DCLXIV provides 345 compounds of formula Iel

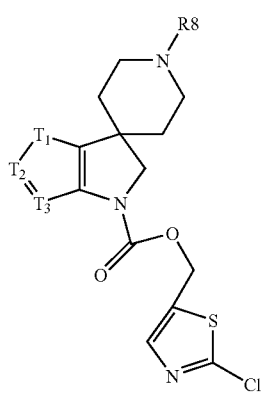

wherein T1 is S, T2 is $CR^{4e}$, T3 is $CR^{4f}$ and the values of $R^8$, $R^{4e}$ and $R^{4f}$ are given in Table 2.

Table DCLXV provides 345 compounds of formula Iem

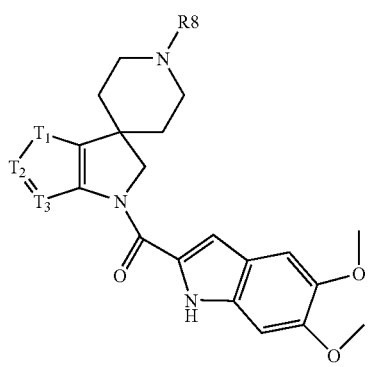

wherein T1 is S, T2 is $CR^{4e}$, T3 is $CR^{4f}$ and the values of $R^8$, $R^{4e}$ and $R^{4f}$ are given in Table 2.

Table DCLXVI provides 345 compounds of formula Ien

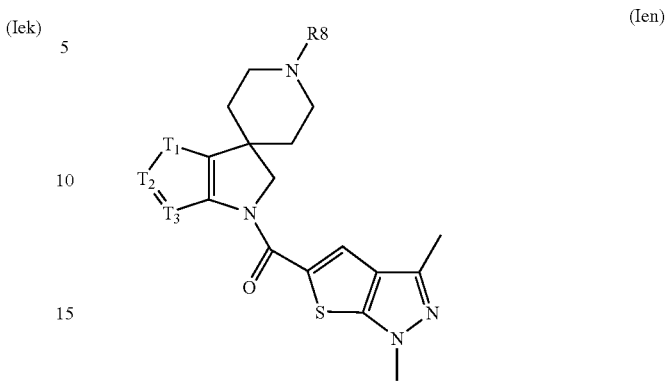

wherein T1 is S, T2 is $CR^{4e}$, T3 is $CR^{4f}$ and the values of $R^8$, $R^{4e}$ and $R^{4f}$ are given in Table 2.

Table DCLXVII provides 345 compounds of formula Ieo

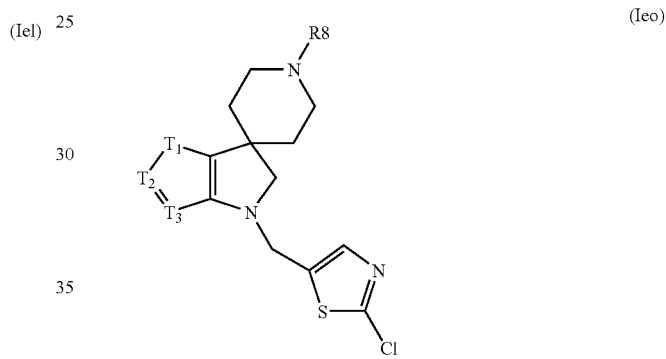

wherein T1 is S, T2 is $CR^{4e}$, T3 is $CR^{4f}$ and the values of $R^8$, $R^{4e}$ and $R^{4f}$ are given in Table 2.

Table DCCI provides 207 compounds of formula Ica wherein T1 is S, T2 is $CR^{4e}$, T3 is N and the values of $R^8$ and $R^{4e}$ are given in Table 3.

TABLE 3

| Compound No | $R^8$ | $C—R^{4e}$ |
|---|---|---|
| DCCI-1 | 4-chlorobenzyl | CH |
| DCCI-2 | Cinnamyl | CH |
| DCCI-3 | 4-chlorocinnamyl | CH |
| DCCI-4 | 4-fluorocinnamyl | CH |
| DCCI-5 | 4-bromocinnamyl | CH |
| DCCI-6 | 4-trifluoromethylcinnamyl | CH |
| DCCI-7 | 4-trifluoromethoxycinnamyl | CH |
| DCCI-8 | 4-pentafluoroethoxycinnamyl | CH |
| DCCI-9 | 4-methoxycinnamyl | CH |
| DCCI-10 | 4-ethoxycinnamyl | CH |
| DCCI-11 | 4-cyanocinnamyl | CH |
| DCCI-12 | 3-(6-chloro-pyridin-3-yl)-allyl | CH |
| DCCI-13 | 3-(4-chlorophenyl)-but-2-enyl | CH |
| DCCI-14 | 3-(4-chlorophenyl)-3-fluoro-allyl | CH |
| DCCI-15 | 3-chloro-4-fluoro-cinnamyl | CH |
| DCCI-16 | 3,5-dichloro-cinnamyl | CH |
| DCCI-17 | 5-phenyl-penta-2,4-dienyl | CH |
| DCCI-18 | 4-isopropyloxycarbonylamino-cinnamyl | CH |
| DCCI-19 | 3-naphthalen-2-yl-allyl | CH |
| DCCI-20 | 3-(5-trifluoromethyl-pyridin-2-yl)-allyl | CH |
| DCCI-21 | 3-(5-chloro-pyridin-2-yl)-allyl | CH |

TABLE 3-continued

| Compound No | R⁸ | C—R⁴ᵉ |
|---|---|---|
| DCCI-22 | 3-pyridin-4-yl-allyl | CH |
| DCCI-23 | 3-(2-Chloro-pyridin-4-yl)-allyl | CH |
| DCCI-24 | 4-chlorobenzyl | CF |
| DCCI-25 | Cinnamyl | CF |
| DCCI-26 | 4-chlorocinnamyl | CF |
| DCCI-27 | 4-fluorocinnamyl | CF |
| DCCI-28 | 4-bromocinnamyl | CF |
| DCCI-29 | 4-trifluoromethylcinnamyl | CF |
| DCCI-30 | 4-trifluoromethoxycinnamyl | CF |
| DCCI-31 | 4-pentafluoroethoxycinnamyl | CF |
| DCCI-32 | 4-methoxycinnamyl | CF |
| DCCI-33 | 4-ethoxycinnamyl | CF |
| DCCI-34 | 4-cyanocinnamyl | CF |
| DCCI-35 | 3-(6-chloro-pyridin-3-yl)-allyl | CF |
| DCCI-36 | 3-(4-chlorophenyl)-but-2-enyl | CF |
| DCCI-37 | 3-(4-chlorophenyl)-3-fluoro-allyl | CF |
| DCCI-38 | 3-chloro-4-fluoro-cinnamyl | CF |
| DCCI-39 | 3,5-dichloro-cinnamyl | CF |
| DCCI-40 | 5-phenyl-penta-2,4-dienyl | CF |
| DCCI-41 | 4-isopropyloxycarbonylamino-cinnamyl | CF |
| DCCI-42 | 3-naphthalen-2-yl-allyl | CF |
| DCCI-43 | 3-(5-trifluoromethyl-pyridin-2-yl)-allyl | CF |
| DCCI-44 | 3-(5-chloro-pyridin-2-yl)-allyl | CF |
| DCCI-45 | 3-pyridin-4-yl-allyl | CF |
| DCCI-46 | 3-(2-Chloro-pyridin-4-yl)-allyl | CF |
| DCCI-47 | 4-chlorobenzyl | CCl |
| DCCI-48 | Cinnamyl | CCl |
| DCCI-49 | 4-chlorocinnamyl | CCl |
| DCCI-50 | 4-fluorocinnamyl | CCl |
| DCCI-51 | 4-bromocinnamyl | CCl |
| DCCI-52 | 4-trifluoromethylcinnamyl | CCl |
| DCCI-53 | 4-trifluoromethoxycinnamyl | CCl |
| DCCI-54 | 4-pentafluoroethoxycinnamyl | CCl |
| DCCI-55 | 4-methoxycinnamyl | CCl |
| DCCI-56 | 4-ethoxycinnamyl | CCl |
| DCCI-57 | 4-cyanocinnamyl | CCl |
| DCCI-58 | 3-(6-chloro-pyridin-3-yl)-allyl | CCl |
| DCCI-59 | 3-(4-chlorophenyl)-but-2-enyl | CCl |
| DCCI-60 | 3-(4-chlorophenyl)-3-fluoro-allyl | CCl |
| DCCI-61 | 3-chloro-4-fluoro-cinnamyl | CCl |
| DCCI-62 | 3,5-dichloro-cinnamyl | CCl |
| DCCI-63 | 5-phenyl-penta-2,4-dienyl | CCl |
| DCCI-64 | 4-isopropyloxycarbonylamino-cinnamyl | CCl |
| DCCI-65 | 3-naphthalen-2-yl-allyl | CCl |
| DCCI-66 | 3-(5-trifluoromethyl-pyridin-2-yl)-allyl | CCl |
| DCCI-67 | 3-(5-chloro-pyridin-2-yl)-allyl | CCl |
| DCCI-68 | 3-pyridin-4-yl-allyl | CCl |
| DCCI-69 | 3-(2-Chloro-pyridin-4-yl)-allyl | CCl |
| DCCI-70 | 4-chlorobenzyl | CBr |
| DCCI-71 | Cinnamyl | CBr |
| DCCI-72 | 4-chlorocinnamyl | CBr |
| DCCI-73 | 4-fluorocinnamyl | CBr |
| DCCI-74 | 4-bromocinnamyl | CBr |
| DCCI-75 | 4-trifluoromethylcinnamyl | CBr |
| DCCI-76 | 4-trifluoromethoxycinnamyl | CBr |
| DCCI-77 | 4-pentafluoroethoxycinnamyl | CBr |
| DCCI-78 | 4-methoxycinnamyl | CBr |
| DCCI-79 | 4-ethoxycinnamyl | CBr |
| DCCI-80 | 4-cyanocinnamyl | CBr |
| DCCI-81 | 3-(6-chloro-pyridin-3-yl)-allyl | CBr |
| DCCI-82 | 3-(4-chlorophenyl)-but-2-enyl | CBr |
| DCCI-83 | 3-(4-chlorophenyl)-3-fluoro-allyl | CBr |
| DCCI-84 | 3-chloro-4-fluoro-cinnamyl | CBr |
| DCCI-85 | 3,5-dichloro-cinnamyl | CBr |
| DCCI-86 | 5-phenyl-penta-2,4-dienyl | CBr |
| DCCI-87 | 4-isopropyloxycarbonylamino-cinnamyl | CBr |
| DCCI-88 | 3-naphthalen-2-yl-allyl | CBr |
| DCCI-89 | 3-(5-trifluoromethyl-pyridin-2-yl)-allyl | CBr |
| DCCI-90 | 3-(5-chloro-pyridin-2-yl)-allyl | CBr |
| DCCI-91 | 3-pyridin-4-yl-allyl | CBr |
| DCCI-92 | 3-(2-Chloro-pyridin-4-yl)-allyl | CBr |
| DCCI-93 | 4-chlorobenzyl | CCN |
| DCCI-94 | Cinnamyl | CCN |
| DCCI-95 | 4-chlorocinnamyl | CCN |
| DCCI-96 | 4-fluorocinnamyl | CCN |
| DCCI-97 | 4-bromocinnamyl | CCN |
| DCCI-98 | 4-trifluoromethylcinnamyl | CCN |
| DCCI-99 | 4-trifluoromethoxycinnamyl | CCN |
| DCCI-100 | 4-pentafluoroethoxycinnamyl | CCN |
| DCCI-101 | 4-methoxycinnamyl | CCN |
| DCCI-102 | 4-ethoxycinnamyl | CCN |
| DCCI-103 | 4-cyanocinnamyl | CCN |
| DCCI-104 | 3-(6-chloro-pyridin-3-yl)-allyl | CCN |
| DCCI-105 | 3-(4-chlorophenyl)-but-2-enyl | CCN |
| DCCI-106 | 3-(4-chlorophenyl)-3-fluoro-allyl | CCN |
| DCCI-107 | 3-chloro-4-fluoro-cinnamyl | CCN |
| DCCI-108 | 3,5-dichloro-cinnamyl | CCN |
| DCCI-109 | 5-phenyl-penta-2,4-dienyl | CCN |
| DCCI-110 | 4-isopropyloxycarbonylamino-cinnamyl | CCN |
| DCCI-111 | 3-naphthalen-2-yl-allyl | CCN |
| DCCI-112 | 3-(5-trifluoromethyl-pyridin-2-yl)-allyl | CCN |
| DCCI-113 | 3-(5-chloro-pyridin-2-yl)-allyl | CCN |
| DCCI-114 | 3-pyridin-4-yl-allyl | CCN |
| DCCI-115 | 3-(2-Chloro-pyridin-4-yl)-allyl | CCN |
| DCCI-116 | 4-chlorobenzyl | COMe |
| DCCI-117 | Cinnamyl | COMe |
| DCCI-118 | 4-chlorocinnamyl | COMe |
| DCCI-119 | 4-fluorocinnamyl | COMe |
| DCCI-120 | 4-bromocinnamyl | COMe |
| DCCI-121 | 4-trifluoromethylcinnamyl | COMe |
| DCCI-122 | 4-trifluoromethoxycinnamyl | COMe |
| DCCI-123 | 4-pentafluoroethoxycinnamyl | COMe |
| DCCI-124 | 4-methoxycinnamyl | COMe |
| DCCI-125 | 4-ethoxycinnamyl | COMe |
| DCCI-126 | 4-cyanocinnamyl | COMe |
| DCCI-127 | 3-(6-chloro-pyridin-3-yl)-allyl | COMe |
| DCCI-128 | 3-(4-chlorophenyl)-but-2-enyl | COMe |
| DCCI-129 | 3-(4-chlorophenyl)-3-fluoro-allyl | COMe |
| DCCI-130 | 3-chloro-4-fluoro-cinnamyl | COMe |
| DCCI-131 | 3,5-dichloro-cinnamyl | COMe |
| DCCI-132 | 5-phenyl-penta-2,4-dienyl | COMe |
| DCCI-133 | 4-isopropyloxycarbonylamino-cinnamyl | COMe |
| DCCI-134 | 3-naphthalen-2-yl-allyl | COMe |
| DCCI-135 | 3-(5-trifluoromethyl-pyridin-2-yl)-allyl | COMe |
| DCCI-136 | 3-(5-chloro-pyridin-2-yl)-allyl | COMe |
| DCCI-137 | 3-pyridin-4-yl-allyl | COMe |
| DCCI-138 | 3-(2-Chloro-pyridin-4-yl)-allyl | COMe |
| DCCI-139 | 4-chlorobenzyl | COCF₃ |
| DCCI-140 | Cinnamyl | COCF₃ |
| DCCI-141 | 4-chlorocinnamyl | COCF₃ |
| DCCI-142 | 4-fluorocinnamyl | COCF₃ |
| DCCI-143 | 4-bromocinnamyl | COCF₃ |
| DCCI-144 | 4-trifluoromethylcinnamyl | COCF₃ |
| DCCI-145 | 4-trifluoromethoxycinnamyl | COCF₃ |
| DCCI-146 | 4-pentafluoroethoxycinnamyl | COCF₃ |
| DCCI-147 | 4-methoxycinnamyl | COCF₃ |
| DCCI-148 | 4-ethoxycinnamyl | COCF₃ |
| DCCI-149 | 4-cyanocinnamyl | COCF₃ |
| DCCI-150 | 3-(6-chloro-pyridin-3-yl)-allyl | COCF₃ |
| DCCI-151 | 3-(4-chlorophenyl)-but-2-enyl | COCF₃ |
| DCCI-152 | 3-(4-chlorophenyl)-3-fluoro-allyl | COCF₃ |
| DCCI-153 | 3-chloro-4-fluoro-cinnamyl | COCF₃ |
| DCCI-154 | 3,5-dichloro-cinnamyl | COCF₃ |
| DCCI-155 | 5-phenyl-penta-2,4-dienyl | COCF₃ |
| DCCI-156 | 4-isopropyloxycarbonylamino-cinnamyl | COCF₃ |
| DCCI-157 | 3-naphthalen-2-yl-allyl | COCF₃ |
| DCCI-158 | 3-(5-trifluoromethyl-pyridin-2-yl)-allyl | COCF₃ |
| DCCI-159 | 3-(5-chloro-pyridin-2-yl)-allyl | COCF₃ |
| DCCI-160 | 3-pyridin-4-yl-allyl | COCF₃ |
| DCCI-161 | 3-(2-Chloro-pyridin-4-yl)-allyl | COCF₃ |
| DCCI-162 | 4-chlorobenzyl | CCH₃ |
| DCCI-163 | Cinnamyl | CCH₃ |
| DCCI-164 | 4-chlorocinnamyl | CCH₃ |
| DCCI-165 | 4-fluorocinnamyl | CCH₃ |
| DCCI-166 | 4-bromocinnamyl | CCH₃ |
| DCCI-167 | 4-trifluoromethylcinnamyl | CCH₃ |
| DCCI-168 | 4-trifluoromethoxycinnamyl | CCH₃ |
| DCCI-169 | 4-pentafluoroethoxycinnamyl | CCH₃ |
| DCCI-170 | 4-methoxycinnamyl | CCH₃ |
| DCCI-171 | 4-ethoxycinnamyl | CCH₃ |
| DCCI-172 | 4-cyanocinnamyl | CCH₃ |
| DCCI-173 | 3-(6-chloro-pyridin-3-yl)-allyl | CCH₃ |
| DCCI-174 | 3-(4-chlorophenyl)-but-2-enyl | CCH₃ |
| DCCI-175 | 3-(4-chlorophenyl)-3-fluoro-allyl | CCH₃ |

TABLE 3-continued

| Compound No | R⁸ | C—R⁴ᵉ |
|---|---|---|
| DCCI-176 | 3-chloro-4-fluoro-cinnamyl | CCH₃ |
| DCCI-177 | 3,5-dichloro-cinnamyl | CCH₃ |
| DCCI-178 | 5-phenyl-penta-2,4-dienyl | CCH₃ |
| DCCI-179 | 4-isopropyloxycarbonylamino-cinnamyl | CCH₃ |
| DCCI-180 | 3-naphthalen-2-yl-allyl | CCH₃ |
| DCCI-181 | 3-(5-trifluoromethyl-pyridin-2-yl)-allyl | CCH₃ |
| DCCI-182 | 3-(5-chloro-pyridin-2-yl)-allyl | CCH₃ |
| DCCI-183 | 3-pyridin-4-yl-allyl | CCH₃ |
| DCCI-184 | 3-(2-Chloro-pyridin-4-yl)-allyl | CCH₃ |
| DCCI-185 | 4-chlorobenzyl | CCF₃ |
| DCCI-186 | Cinnamyl | CCF₃ |
| DCCI-187 | 4-chlorocinnamyl | CCF₃ |
| DCCI-188 | 4-fluorocinnamyl | CCF₃ |
| DCCI-189 | 4-bromocinnamyl | CCF₃ |
| DCCI-190 | 4-trifluoromethylcinnamyl | CCF₃ |
| DCCI-191 | 4-trifluoromethoxycinnamyl | CCF₃ |
| DCCI-192 | 4-pentafluoroethoxycinnamyl | CCF₃ |
| DCCI-193 | 4-methoxycinnamyl | CCF₃ |
| DCCI-194 | 4-ethoxycinnamyl | CCF₃ |
| DCCI-195 | 4-cyanocinnamyl | CCF₃ |
| DCCI-196 | 3-(6-chloro-pyridin-3-yl)-allyl | CCF₃ |
| DCCI-197 | 3-(4-chlorophenyl)-but-2-enyl | CCF₃ |
| DCCI-198 | 3-(4-chlorophenyl)-3-fluoro-allyl | CCF₃ |
| DCCI-199 | 3-chloro-4-fluoro-cinnamyl | CCF₃ |
| DCCI-200 | 3,5-dichloro-cinnamyl | CCF₃ |
| DCCI-201 | 5-phenyl-penta-2,4-dienyl | CCF₃ |
| DCCI-202 | 4-isopropyloxycarbonylamino-cinnamyl | CCF₃ |
| DCCI-203 | 3-naphthalen-2-yl-allyl | CCF₃ |
| DCCI-204 | 3-(5-trifluoromethyl-pyridin-2-yl)-allyl | CCF₃ |
| DCCI-205 | 3-(5-chloro-pyridin-2-yl)-allyl | CCF₃ |
| DCCI-206 | 3-pyridin-4-yl-allyl | CCF₃ |
| DCCI-207 | 3-(2-Chloro-pyridin-4-yl)-allyl | CCF₃ |

Table DCCII provides 207 compounds of formula Icb wherein T1 is S, T2 is $CR^{4e}$, T3 is N and the values of $R^8$ and $R^{4e}$ are given in Table 3.

Table DCCIII provides 207 compounds of formula Icc wherein T1 is S, T2 is $CR^{4e}$, T3 is N and the values of $R^8$ and $R^{4e}$ are given in Table 3.

Table DCCIV provides 207 compounds of formula Icd wherein T1 is S, T2 is $CR^{4e}$, T3 is N and the values of $R^8$ and $R^{4e}$ are given in Table 3.

Table DCCV provides 207 compounds of formula Ice wherein T1 is S, T2 is $CR^{4e}$, T3 is N and the values of $R^8$ and $R^{4e}$ are given in Table 3.

Table DCCVI provides 207 compounds of formula Icf wherein T1 is S, T2 is $CR^{4e}$, T3 is N and the values of $R^8$ and $R^{4e}$ are given in Table 3.

Table DCCVII provides 207 compounds of formula Icg wherein T1 is S, T2 is $CR^{4e}$, T3 is N and the values of $R^8$ and $R^{4e}$ are given in Table 3.

Table DCCVIII provides 207 compounds of formula Ich wherein T1 is S, T2 is $CR^{4e}$, T3 is N and the values of $R^8$ and $R^{4e}$ are given in Table 3.

Table DCCIX provides 207 compounds of formula Ici wherein T1 is S, T2 is $CR^{4e}$, T3 is N and the values of $R^8$ and $R^{4e}$ are given in Table 3.

Table DCCX provides 207 compounds of formula Icj wherein T1 is S, T2 is $CR^{4e}$, T3 is N and the values of $R^8$ and $R^{4e}$ are given in Table 3.

Table DCCXI provides 207 compounds of formula Ick wherein T1 is S, T2 is $CR^{4e}$, T3 is N and the values of $R^8$ and $R^{4e}$ are given in Table 3.

Table DCCXII provides 207 compounds of formula Icl wherein T1 is S, T2 is $CR^{4e}$, T3 is N and the values of $R^8$ and $R^{4e}$ are given in Table 3.

Table DCCXIII provides 207 compounds of formula Icm wherein T1 is S, T2 is $CR^{4e}$, T3 is N and the values of $R^8$ and $R^{4e}$ are given in Table 3.

Table DCCXIV provides 207 compounds of formula Icn wherein T1 is S, T2 is $CR^{4e}$, T3 is N and the values of $R^8$ and $R^{4e}$ are given in Table 3.

Table DCCXV provides 207 compounds of formula Ico wherein T1 is S, T2 is $CR^{4e}$, T3 is N and the values of $R^8$ and $R^{4e}$ are given in Table 3.

Table DCCXVI provides 207 compounds of formula Icp wherein T1 is S, T2 is $CR^{4e}$, T3 is N and the values of $R^8$ and $R^{4e}$ are given in Table 3.

Table DCCXVII provides 207 compounds of formula Icq wherein T1 is S, T2 is $CR^{4e}$, T3 is N and the values of $R^8$ and $R^{4e}$ are given in Table 3.

Table DCCXVIII provides 207 compounds of formula Ir wherein T1 is S, T2 is $CR^{4e}$, T3 is N and the values of $R^8$ and $R^{4e}$ are given in Table 3.

Table DCCXIX provides 207 compounds of formula Ics wherein T1 is S, T2 is $CR^{4e}$, T3 is N and the values of $R^8$ and $R^{4e}$ are given in Table 3.

Table DCCXX provides 207 compounds of formula Ict wherein T1 is S, T2 is $CR^{4e}$, T3 is N and the values of $R^8$ and $R^{4e}$ are given in Table 3.

Table DCCXXI provides 207 compounds of formula Icu wherein T1 is S, T2 is $CR^{4e}$, T3 is N and the values of $R^8$ and $R^{4e}$ are given in Table 3.

Table DCCXXII provides 207 compounds of formula Icv wherein T1 is S, T2 is $CR^{4e}$, T3 is N and the values of $R^8$ and $R^{4e}$ are given in Table 3.

Table DCCXXIII provides 207 compounds of formula Icw wherein T1 is S, T2 is $CR^{4e}$, T3 is N and the values of $R^8$ and $R^{4e}$ are given in Table 3.

Table DCCXXIV provides 207 compounds of formula Icx wherein T1 is S, T2 is $CR^{4e}$, T3 is N and the values of $R^8$ and $R^{4e}$ are given in Table 3.

Table DCCXXV provides 207 compounds of formula Icy wherein T1 is S, T2 is $CR^{4e}$, T3 is N and the values of $R^8$ and $R^{4e}$ are given in Table 3.

Table DCCXXVI provides 207 compounds of formula Icz wherein T1 is S, T2 is $CR^{4e}$, T3 is N and the values of $R^8$ and $R^{4e}$ are given in Table 3.

Table DCCXXVII provides 207 compounds of formula Ida wherein T1 is S, T2 is $CR^{4e}$, T3 is N and the values of $R^8$ and $R^{4e}$ are given in Table 3.

Table DCCXXVIII provides 207 compounds of formula Idb wherein T1 is S, T2 is $CR^{4e}$, T3 is N and the values of $R^8$ and $R^{4e}$ are given in Table 3.

Table DCCXXIX provides 207 compounds of formula Idc wherein T1 is S, T2 is $CR^{4e}$, T3 is N and the values of $R^8$ and $R^{4e}$ are given in Table 3.

Table DCCXXX provides 207 compounds of formula Idd wherein T1 is S, T2 is $CR^{4e}$, T3 is N and the values of $R^8$ and $R^{4e}$ are given in Table 3.

Table DCCXXXI provides 207 compounds of formula Ide wherein T1 is S, T2 is $CR^{4e}$, T3 is N and the values of $R^8$ and $R^{4e}$ are given in Table 3.

Table DCCXXXII provides 207 compounds of formula Idf wherein T1 is S, T2 is $CR^{4e}$, T3 is N and the values of $R^8$ and $R^{4e}$ are given in Table 3.

Table DCCXXXIII provides 207 compounds of formula Idg wherein T1 is S, T2 is $CR^{4e}$, T3 is N and the values of $R^8$ and $R^{4e}$ are given in Table 3.

Table DCCXXXIV provides 207 compounds of formula Idh wherein T1 is S, T2 is $CR^{4e}$, T3 is N and the values of $R^8$ and $R^{4e}$ are given in Table 3.

Table DCCXXXV provides 207 compounds of formula Idi wherein T1 is S, T2 is $CR^{4e}$, T3 is N and the values of $R^8$ and $R^{4e}$ are given in Table 3.

Table DCCXXXVI provides 207 compounds of formula Idj wherein T1 is S, T2 is $CR^{4e}$, T3 is N and the values of $R^8$ and $R^{4e}$ are given in Table 3.
Table DCCXXXVII provides 207 compounds of formula Idk wherein T1 is S, T2 is $CR^{4e}$, T3 is N and the values of $R^8$ and $R^{4e}$ are given in Table 3.
Table DCCXXXVIII provides 207 compounds of formula Idl wherein T1 is S, T2 is $CR^{4e}$, T3 is N and the values of $R^8$ and $R^{4e}$ are given in Table 3.
Table DCCXXXIX provides 207 compounds of formula Idm wherein T1 is S, T2 is $CR^{4e}$, T3 is N and the values of $R^8$ and $R^{4e}$ are given in Table 3.
Table DCCXL provides 207 compounds of formula Idn wherein T1 is S, T2 is $CR^{4e}$, T3 is N and the values of $R^8$ and $R^{4e}$ are given in Table 3.
Table DCCXLI provides 207 compounds of formula Ido wherein T1 is S, T2 is $CR^{4e}$, T3 is N and the values of $R^8$ and $R^{4e}$ are given in Table 3.
Table DCCXLII provides 207 compounds of formula Idp wherein T1 is S, T2 is $CR^{4e}$, T3 is N and the values of $R^8$ and $R^{4e}$ are given in Table 3.
Table DCCXLIII provides 207 compounds of formula Idq wherein T1 is S, T2 is $CR^{4e}$, T3 is N and the values of $R^8$ and $R^{4e}$ are given in Table 3.
Table DCCXLIV provides 207 compounds of formula Idr wherein T1 is S, T2 is $CR^{4e}$, T3 is N and the values of $R^8$ and $R^{4e}$ are given in Table 3.
Table DCCXLV provides 207 compounds of formula Ids wherein T1 is S, T2 is $CR^{4e}$, T3 is N and the values of $R^8$ and $R^{4e}$ are given in Table 3.
Table DCCXLVI provides 207 compounds of formula Idt wherein T1 is S, T2 is $CR^{4e}$, T3 is N and the values of $R^8$ and $R^{4e}$ are given in Table 3.
Table DCCXLVII provides 207 compounds of formula Idu wherein T1 is S, T2 is $CR^{4e}$, T3 is N and the values of $R^8$ and $R^{4e}$ are given in Table 3.
Table DCCXLVIII provides 207 compounds of formula Idv wherein T1 is S, T2 is $CR^{4e}$, T3 is N and the values of $R^8$ and $R^{4e}$ are given in Table 3.
Table DCCIL provides 207 compounds of formula Idw wherein T1 is S, T2 is $CR^{4e}$, T3 is N and the values of $R^8$ and $R^{4e}$ are given in Table 3.
Table DCCL provides 207 compounds of formula Idx wherein T1 is S, T2 is $CR^{4e}$, T3 is N and the values of $R^8$ and $R^{4e}$ are given in Table 3.
Table DCCLI provides 207 compounds of formula wherein T1 is S, T2 is $CR^{4e}$, T3 is N and the values of $R^8$ and $R^{4e}$ are given in Table 3.
Table DCCLII provides 207 compounds of formula Idz wherein T1 is S, T2 is $CR^{4e}$, T3 is N and the values of $R^8$ and $R^{4e}$ are given in Table 3.
Table DCCLIII provides 207 compounds of formula Iea wherein T1 is S, T2 is $CR^{4e}$, T3 is N and the values of $R^8$ and $R^{4e}$ are given in Table 3.
Table DCCLIV provides 207 compounds of formula Ieb wherein T1 is S, T2 is $CR^{4e}$, T3 is N and the values of $R^8$ and $R^{4e}$ are given in Table 3.
Table DCCLV provides 207 compounds of formula Iec wherein T1 is S, T2 is $CR^{4e}$, T3 is N and the values of $R^8$ and $R^{4e}$ are given in Table 3.
Table DCCLVI provides 207 compounds of formula Ied wherein T1 is S, T2 is $CR^{4e}$, T3 is N and the values of $R^8$ and $R^{4e}$ are given in Table 3.
Table DCCLVII provides 207 compounds of formula Iee wherein T1 is S, T2 is $CR^{4e}$, T3 is N and the values of $R^8$ and $R^{4e}$ are given in Table 3.
Table DCCLVIII provides 207 compounds of formula Ief wherein T1 is S, T2 is $CR^{4e}$, T3 is N and the values of $R^8$ and $R^{4e}$ are given in Table 3.
Table DCCLIX provides 207 compounds of formula Ieg wherein T1 is S, T2 is $CR^{4e}$, T3 is N and the values of $R^8$ and $R^{4e}$ are given in Table 3.
Table DCCLX provides 207 compounds of formula Ieh wherein T1 is S, T2 is $CR^{4e}$, T3 is N and the values of $R^8$ and $R^{4e}$ are given in Table 3.
Table DCCLXI provides 207 compounds of formula Iei wherein T1 is S, T2 is $CR^{4e}$, T3 is N and the values of $R^8$ and $R^{4e}$ are given in Table 3.
Table DCCLXII provides 207 compounds of formula Iej wherein T1 is S, T2 is $CR^{4e}$, T3 is N and the values of $R^8$ and $R^{4e}$ are given in Table 3.
Table DCCLXIII provides 207 compounds of formula Iek wherein T1 is S, T2 is $CR^{4e}$, T3 is N and the values of $R^8$ and $R^{4e}$ are given in Table 3.
Table DCCLXIV provides 207 compounds of formula Iel wherein T1 is S, T2 is $CR^{4e}$, T3 is N and the values of $R^8$ and $R^{4e}$ are given in Table 3.
Table DCCLXV provides 207 compounds of formula Iem wherein T1 is S, T2 is $CR^{4e}$, T3 is N and the values of $R^8$ and $R^{4e}$ are given in Table 3.
Table DCCLXVI provides 207 compounds of formula Ien wherein T1 is S, T2 is $CR^{4e}$, T3 is N and the values of $R^8$ and $R^{4e}$ are given in Table 3.
Table DCCLXVII provides 207 compounds of formula Ieo wherein T1 is S, T2 is $CR^{4e}$, T3 is N and the values of $R^8$ and $R^{4e}$ are given in Table 3.

Mass spectra data were obtained for selected compounds of Tables I to DCCLXVII using LCMS: LC5 (or LCMS:LC3; retention times with * in the table 4): 254 nm—gradient 10% A to 100% B A=H2O+0.01% HCOOH B=CH3CN/CH3OH+ 0.01% HCOOH positive electrospray 150-1000 m/z.

The data are shown in Table 4.

TABLE 4

| Compound | LCMS (Ret. Time, min) | LCMS (M + H) | m.pt. |
|---|---|---|---|
| I-26 | 1'44* | 400 | |
| I-29 | 1'49* | 434 | |
| I-30 | 1'52* | 450 | |
| I-210 | 1'54* | 416 | |
| I-213 | 1'55* | 450 | |
| I-214 | 1'59* | 466 | |
| I-233 | 1'45* | 400 | |
| I-236 | 1'52* | 434 | |
| I-237 | 1'49* | 450 | |
| II-26 | 1'49* | 463 | |
| II-29 | 1'54* | 497 | |
| II-30 | 1'58* | 513 | |
| II-210 | 1'98 | 479 | |
| II-213 | 2'13 | 513 | |
| II-214 | 2'13 | 529 | |
| III-3 | 2'46 | 479 | |
| III-6 | 2'13 | 513 | |
| III-7 | 2'31 | 529 | |
| III-26 | 2'42 | 497 | |
| III-29 | 2'64 | 531 | |
| III-30 | 2'63 | 547 | |
| III-210 | 2'26 | 513 | |
| III-210 N-oxide | 2'36 | 529 | |
| III-213 | 2'40 | 547 | |
| III-214 | 2'40 | 563 | |
| III-233 | 2'12 | 497 | |
| III-236 | 2'20 | 531 | |
| III-237 | 2'27 | 547 | |
| III-302 | 2'40 | 493 | |
| III-325 | 2'63 | 547 | |

TABLE 4-continued

| Compound | LCMS (Ret. Time, min) | LCMS (M + H) | m.pt. |
|---|---|---|---|
| III-328 | 2'47 | 581 | |
| III-329 | 2'46 | 597 | |
| V-26 | 2'65 | 531 | |
| V-29 | 2'75 | 565 | |
| V-30 | 2'60 | 581 | |
| V-209 | 2'33 | 513 | |
| V-210 | 2'83 | 547 | |
| V-213 | 2'62 | 581 | |
| V-214 | 2'41 | 597 | |
| V-233 | 2'19 | 531 | |
| V-236 | 2'28 | 565 | |
| V-237 | 2'84 | 581 | |
| V-509 | 1'82* | 565 | |
| VIII-26 | 1'55* | 481 | |
| VIII-29 | 1'59* | 515 | |
| VIII-30 | 1'63* | 531 | |
| VIII-210 | 1'57* | 497 | |
| VIII-213 | 1'77* | 531 | |
| VIII-214 | 1'61* | 547 | |
| XX-26 | 1'64* | 532 | |
| XX-29 | 1'67* | 566 | |
| XX-30 | 1'69* | 582 | |
| XX-210 | 2'72 | 548 | |
| XX-213 | 1'74* | 582 | |
| XX-214 | 1'75* | 598 | |
| XX-233 | 2'54 | 532 | |
| XX-236 | 1'65* | 566 | |
| XX-237 | 1'69* | 582 | |
| CIII-49 | | | 208 |
| CIII-52 | | | 91-93 |
| CIII-53 | | | 78-80 |
| CIII-210 | | | 95-96 |
| CIII-214 | | | 81-83 |
| CIII-555 | | | 107 |
| CCIII-3 | 1'91 | 479 | |
| CCIII-6 | 2'02 | 513 | |
| CCIII-7 | 1'74 | 529 | |
| CCCI-3 | 1'77 | 382 | |
| CCCIII-3 | 1'98 | 479 | |
| CCCIII-26 | 2'04 | 497 | |
| CCCIII-29 | 2'15 | 531 | |
| CCCIII-30 | 2'19 | 547 | |
| CCCV-3 | 2'24 | 513 | |
| CCCV-26 | 2'32 | 531 | |
| CCCV-29 | 2'42 | 565 | |
| CCCV-30 | 2'45 | 581 | |
| CCCVI-3 | 2'30 | 603 | |
| CDIII-49 | 1'56* | 514 | |
| CDIII-52 | 1'60* | 548 | |
| CDIII-53 | 1'62* | 564 | |
| CDV-49 | 1'66* | 548 | |
| CDV-52 | 1'72* | 582 | |
| DIII-3 | 2'32 | 480 | |
| DIII-210 | 2'41 | 514 | |
| DV-3 | 2'17 | 514 | |
| DV-210 | 2'47 | 582 | |
| DV-213 | 2'37 | 548 | |
| DV-214 | 2'51 | 598 | |
| DCIII-3 | | | 81-82 |
| DCIII-6 | | | 73-77 |
| DCIII-7 | | | 70-74 |
| DCIII-49 | | | 69-72 |
| DCIII-52 | | | 75 |
| DCIII-53 | | | 70 |
| DCV-53 | | | 62 |

The compounds of the invention may be made in a variety of ways. For example as shown in Scheme I.

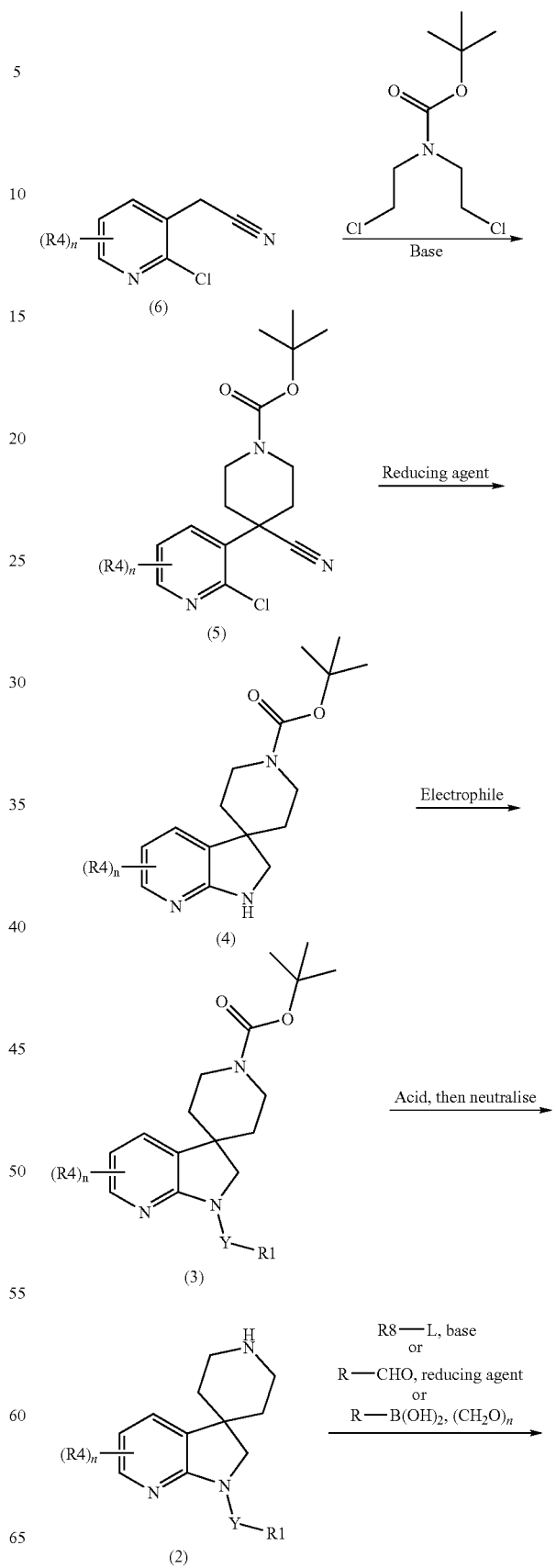

SCHEME I

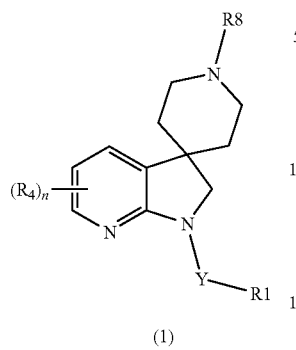

(1)

Thus a compound of formula 1 may be synthesised from compounds of formula 2 by reaction with an alkylating agent of the formula R8-L, where L is chloride, bromide, iodide or a sulfonate (e.g. mesylate or tosylate) or similar leaving group at a temperature of between ambient temperature and 100° C., typically 65° C., in an organic solvent such as dichloromethane, chloroform or 1,2-dichloroethane in the presence of a tertiary amine base such as triethylamine or diisopropylethylamine and optionally catalysed by halide salts such as sodium iodide, potassium iodide or tetrabutylammonium iodide.

Alternatively, a compound of formula 2 may be reacted with an aldehyde of the formula RCHO at a temperature between ambient temperature and 100° C. in an organic solvent such as tetrahydrofuran or ethanol or mixtures of solvents in the presence of a reducing agent such as borane-pyridine complex, sodium borohydride, sodium (triacetoxy) borohydride, sodium cyanoborohydride or such like, to produce a compound of formula 1 where R8 is $CH_2$—R.

Alternatively, a compound of formula 2 may be reacted with paraformaldehyde and a boronic acid of the formula R—$B(OH)_2$ at a temperature between ambient temperature and 100° C. in an organic solvent such as ethanol, 1,4-dioxane or water to produce a compound of formula 1 where R8 is $CH_2$—R.

A compound of formula 2 may be obtained from a compound of formula 3 by reaction with an acid such as trifluoroacetic acid at ambient temperature in an organic solvent such as dichloromethane, chloroform or 1,2-dichloroethane followed by neutralisation of the reaction mixture with an aqueous solution of an inorganic base such as sodium carbonate, sodium bicarbonate or similar compound.

Compounds of formula 3 may be obtained from compounds of formula 4 by reaction with a suitable electrophilic species. Compounds of formula 3 where Y is a carbonyl group may be formed by the reaction of compounds of formula 4 with a carboxylic acid derivative of formula R1-C(O)—Z where Z is chloride, hydroxy, alkoxy or acyloxy at a temperature between 0° C. and 150° C. optionally in an organic solvent such as dichloromethane, chloroform or 1,2-dichloroethane, optionally in the presence of a tertiary amine base such as triethylamine or diisopropylethylamine and option- ally in the presence of a coupling agent such as dicyclohexylcarbodiimide. Compounds of formula 3 where Y is a carbonyl group and R1 is an amino substituent of formula R'—NH— may be formed by the reaction of compounds of formula 4 with an isocyanate of formula R'—N═C═O under similar conditions. Compounds of formula 3 where Y is a group of formula $S(O)_q$ may be formed from compounds of formula 4 by treatment with compounds of formula of R1-S$(O)_q$—Cl under similar conditions. Compounds of formula 3 where Y is a thiocarbonyl group and R1 is an amino substituent of formula R'—NH— may be formed by the reaction of compounds of formula 3 with an isothiocyanate of formula R'—N═C═S under similar conditions. Alternatively compounds of formula 3 where Y is a thiocarbonyl group and R1 is a carbon substituent may be formed by treatment of compounds of formula 3 where Y is a carbonyl group and R1 is a carbon substituent with a suitable thionating agent such as Lawesson's reagent.

In the above procedures, acid derivatives of the formula R1-C(O)—Z, isocyanates of formula R'—N═C═O, isothiocyanates of formula R'—N═C═S and sulfur electrophiles of formula R1-S$(O)_q$—Cl are either known compounds or may be formed from known compounds by known methods by a person skilled in the art.

Compounds of formula 4 may be obtained from compounds of formula 5 by reaction with a suitable reducing agent such as lithium-tri-tert-butoxyaluminohydride or similar hydrides or alkoxyhydrides in an organic solvent such as in dioxane or at temperature of between 100° C. and 125° C., following the procedure described in WO-0027845.

Compounds of formula 5 may be obtained from compounds of formula 6, following the procedure described in WO00/27845.

Compounds of formula 6 may be obtained following the procedure described by Bremner et al. in Synthesis 1991, 528.

Compounds of formula 5 and 6 are either known compounds or may be formed from known compounds by known methods by a person skilled in the art.

Certain compounds of formula 2, 3 and 4 are novel compounds and as such form a further aspect of the invention.

Alternatively compounds of formula 1 may be made by the reactions summarised in Scheme II

SCHEME II

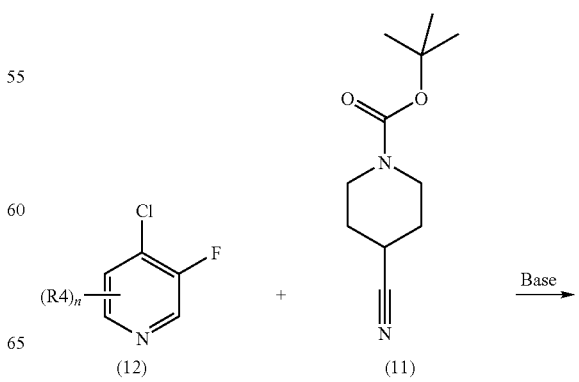

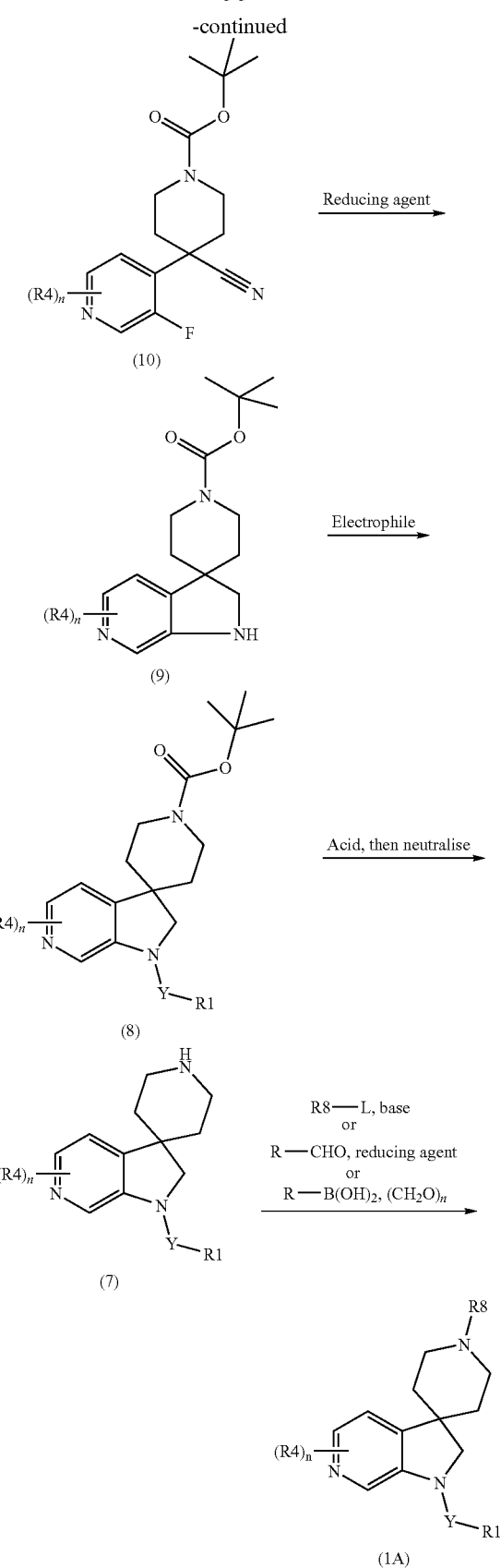

Thus a compound of formula 1A may be synthesised from compounds of formula 7 by reaction with an alkylating agent of the formula R8-L, where L is chloride, bromide, iodide or a sulfonate (e.g. mesylate or tosylate) or similar leaving group at a temperature of between ambient temperature and 100° C., typically 65° C., in an organic solvent such as dichloromethane, chloroform or 1,2-dichloroethane in the presence of a tertiary amine base such as triethylamine or diisopropylethylamine and optionally catalysed by halide salts such lo as sodium iodide, potassium iodide or tetrabutylammonium iodide.

Alternatively, a compound of formula 7 may be reacted with an aldehyde of the formula RCHO at a temperature between ambient temperature and 100° C. in an organic solvent such as tetrahydrofuran or ethanol or mixtures of solvents in the presence of a reducing agent such as borane-pyridine complex, sodium borohydride, sodium (triacetoxy) borohydride, sodium cyanoborohydride or such like, to produce a compound of formula 1A where R8 is $CH_2$—R.

Alternatively, a compound of formula 7 may be reacted with paraformaldehyde and a boronic acid of the formula R—$B(OH)_2$ at a temperature between ambient temperature and 100° C. in an organic solvent such as ethanol, 1,4-dioxane or water to produce a compound of formula 1A where R8 is $CH_2$—R.

A compound of formula 7 may be obtained from a compound of formula 8 by reaction with an acid such as trifluoroacetic acid at ambient temperature in an organic solvent such as dichloromethane, chloroform or 1,2-dichloroethane followed by neutralisation of the reaction mixture with an aqueous solution of an inorganic base such as sodium carbonate, sodium bicarbonate or similar compound.

Compounds of formula 8 may be obtained from compounds of formula 9 by reaction with a suitable electrophilic species. Compounds of formula 8 where Y is a carbonyl group may be formed by the reaction of compounds of formula 9 with a carboxylic acid derivative of formula R1-C(O)—Z where Z is chloride, hydroxy, alkoxy or acyloxy at a temperature between 0° C. and 150° C. optionally in an organic solvent such as dichloromethane, chloroform or 1,2-dichloroethane, optionally in the presence of a tertiary amine base such as triethylamine or diisopropylethylamine and optionally in the presence of a coupling agent such as dicyclohexylcarbodiimide. Compounds of formula 8 where Y is a carbonyl group and R1 is an amino substituent of formula R'—NH— may be formed by the reaction of compounds of formula 9 with an isocyanate of formula R'—N=C=O under similar conditions. Compounds of formula 8 where Y is a group of formula $S(O)_q$ may be formed from compounds of formula 9 by treatment with compounds of formula of R1-S(O)$_q$—Cl under similar conditions. Compounds of formula 8 where Y is a thiocarbonyl group and R1 is an amino substituent of formula R'—NH— may be formed by the reaction of compounds of formula 8 with an isothiocyanate of formula R'—N=C=S under similar conditions. Alternatively compounds of formula 8 where Y is a thiocarbonyl group and R1 is a carbon substituent may be formed by treatment of compounds of formula 8 where Y is a carbonyl group and R1 is a carbon substituent with a suitable thionating agent such as Lawesson's reagent.

In the above procedures, acid derivatives of the formula R1-C(O)—Z, isocyanates of formula R'—N=C=O, isothiocyanates of formula R'—N=C=S and sulfur electrophiles of formula R1-S(O)$_q$—Cl are either known compounds or may be formed from known compounds by known methods by a person skilled in the art.

Compounds of formula 9 may be obtained from compounds of formula 10 by reaction with a suitable reducing agent such as lithium-tri-tert-butoxyaluminohydride or similar hydrides or alkoxyhydrides in an organic solvent such as in dioxane or at temperature of between 100° C. and 125° C., following the procedure described in WO00/27845.

Compounds of formula 10 may be obtained from compounds of formula 11 and 12, following known procedures.

Compounds of formula 10, 11 and 12 are either known compounds or may be formed from known compounds by known methods by a person skilled in the art.

Certain compounds of formula 7, 8 and 9 are novel compounds and as such form a further aspect of the invention.

Compounds of formula 1 may also be made by the routes described in scheme III:

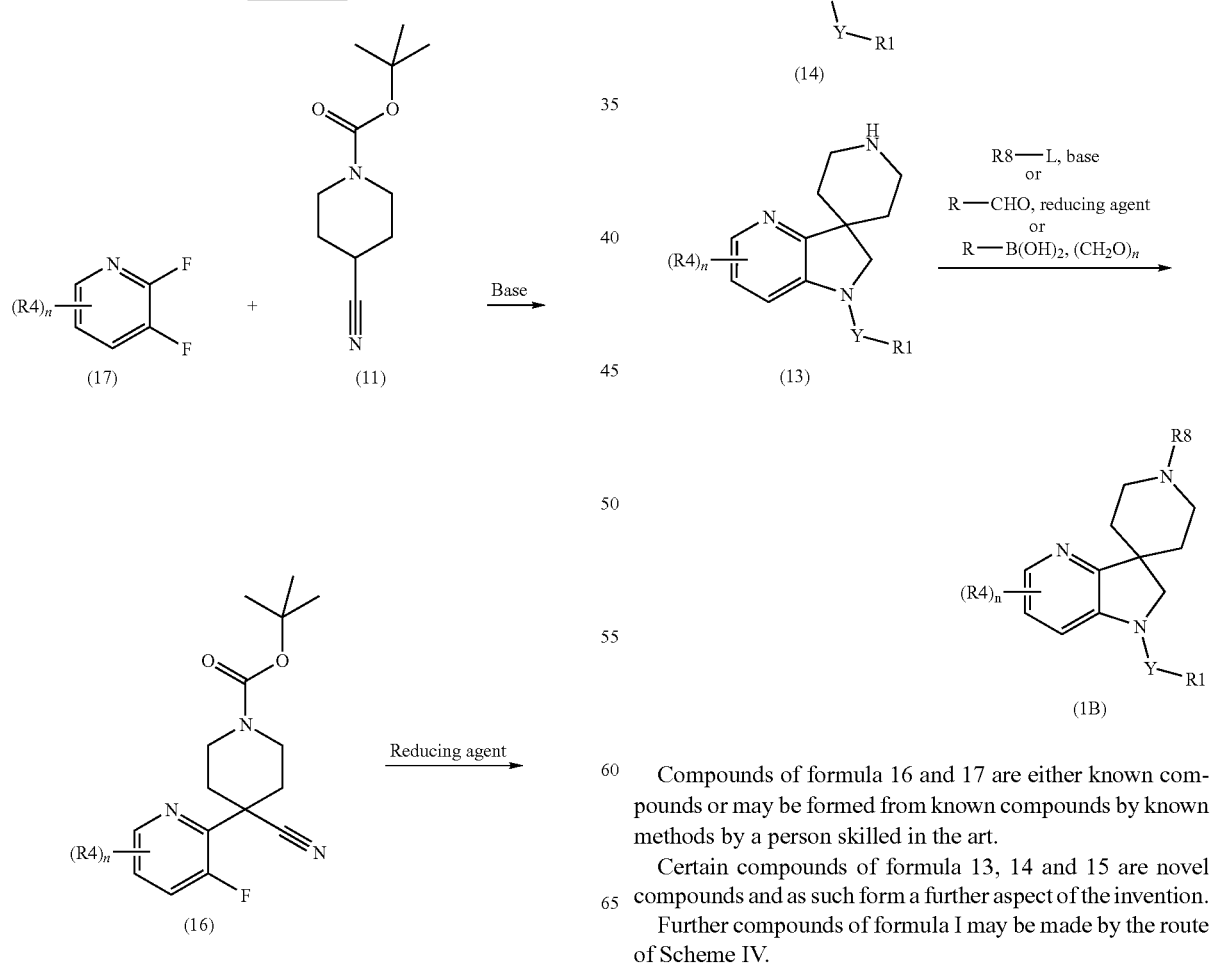

Compounds of formula 16 and 17 are either known compounds or may be formed from known compounds by known methods by a person skilled in the art.

Certain compounds of formula 13, 14 and 15 are novel compounds and as such form a further aspect of the invention.

Further compounds of formula I may be made by the route of Scheme IV.

SCHEME IV

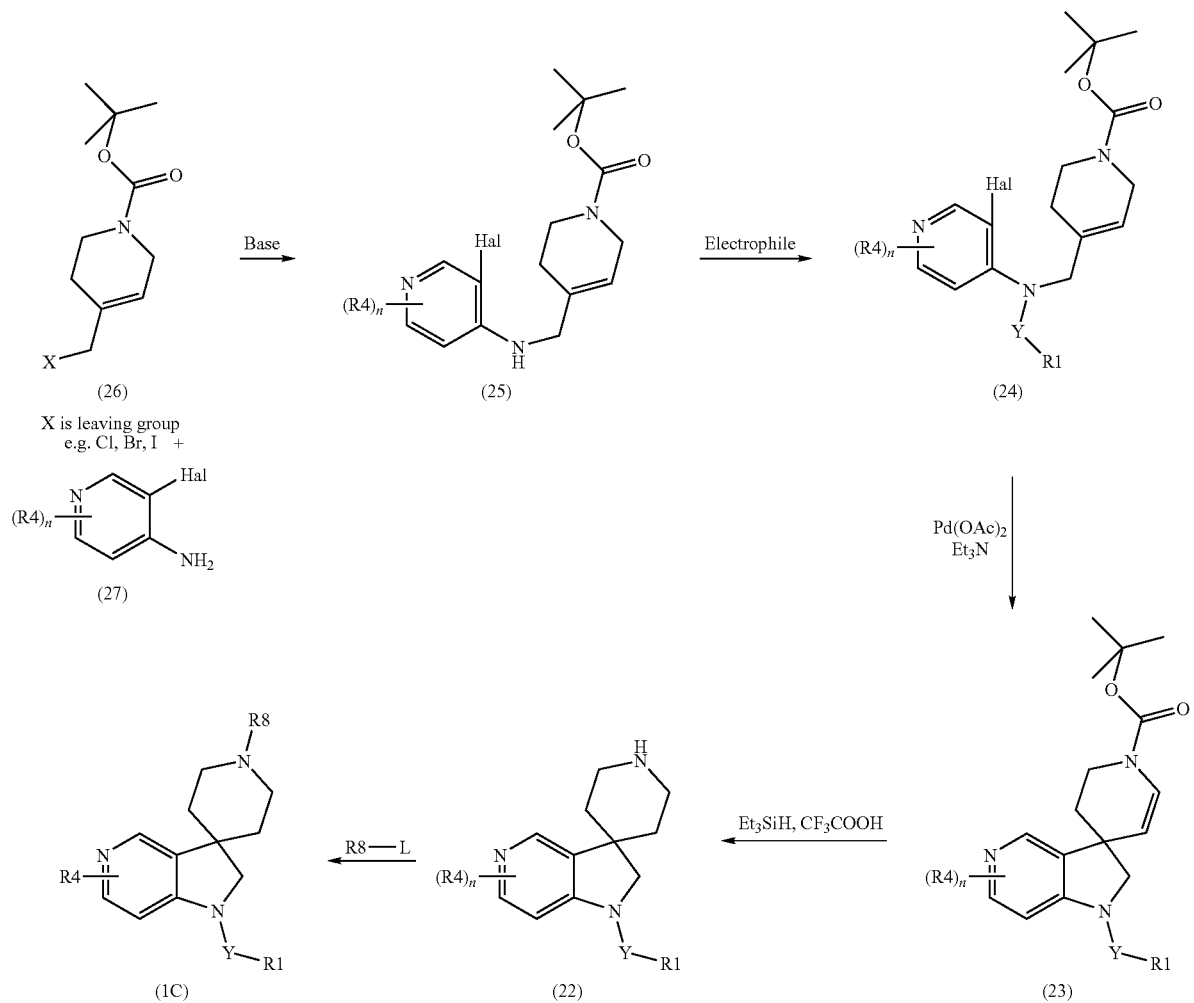

A compound of formula 1C may be synthesised from compounds of formula 22 by reaction with an alkylating agent of the formula R8-L, where L is chloride, bromide, iodide or a sulfonate (e.g. mesylate or tosylate) or similar leaving group at a temperature of between ambient temperature and 100° C., typically ambient temperature, in an organic solvent such as acetonitrile, dimethylformamide, dichloromethane, chloroform or 1,2-dichloroethane in the presence of a tertiary amine base such as triethylamine or diisopropylethylamine and optionally catalysed by halide salts such as sodium iodide, potassium iodide or tetrabutylammonium iodide.

A compound of formula 22 may be obtained from a compound of formula 23 by reaction with an acid such as trifluoroacetic acid and a reducing agent such as triethylsilane at ambient temperature in an organic solvent such as dichloromethane, chloroform or 1,2-dichloroethane followed by neutralisation of the reaction mixture with an aqueous solution of an inorganic base such as sodium carbonate, sodium bicarbonate or similar compound.

A compound of formula 23 may be obtained by cyclising a compound of formula 24 under Heck conditions in the presence of a catalyst such as palladium acetate, optionally a ligand such as triphenylphosphine or/and an additive such as tetrabutylammonium bromide and a base such as triethylamine in an organic solvent such as tetrahydrofuran, acetonitrile or dimethylformamide at a temperature of between 50° C. to 140° C.

Compounds of formula 24 may be obtained from compounds of formula 25 by reaction with a suitable electrophilic species. Compounds of formula 24 where Y is a carbonyl group may be formed by the reaction of compounds of formula 25 with a carboxylic acid derivative of formula R1-C(O)—Z where Z is chloride, hydroxy, alkoxy or acyloxy at a temperature between 0° C. and 150° C. optionally in an organic solvent such as dichloromethane, chloroform or 1,2-dichloroethane, optionally in the presence of a tertiary amine base such as triethylamine or diisopropylethylamine and optionally in the presence of a coupling agent such as dicyclohexylcarbodiimide. Compounds of formula 24 where Y is a carbonyl group and R1 is an amino substituent of formula R'—NH— maybe be formed by the reaction of compounds of formula 25 with an isocyanate of formula R'—N=C=O under similar conditions. Compounds of formula 1C where Y is a group of formula $S(O)_q$ may be formed from compounds of formula 22 by treatment with compounds of formula R1-$S(O)_q$—Cl under similar conditions. Compounds of formula 24 where Y is a thiocarbonyl group and R1 is an amino substituent of formula R'—NH— may be formed by the reaction of compounds of formula 25 with an isothiocyanate of formula R'—N=C=S under similar conditions. Alternatively compounds of formula 24 where Y is a thiocarbonyl group and R1 is a carbon substituent may be formed by treatment of compounds of formula 24 where Y is a carbonyl group and R1 is a carbon substituent with a suitable thionating agent such as Lawesson's reagent.

In the above procedures, acid derivatives of the formula R1-C(O)—Z, isocyanates of formula R'—N=C=O, isothiocyanates of formula R'—N=C=S and sulfur electrophiles of formula R1- $S(O)_q$—Cl are either known compounds or may be formed from known compounds by known methods by a person skilled in the art.

Compounds of formula 25 may be synthesised by alkylating a compound of formula 27 (in which the amino group may if necessary be protected e.g. by an acyl group which can be removed after the reaction) with a compound of formula 26 in the presence of a base such as sodium hydride, lithium aluminium hydride or potassium tertbutoxide at a temperature of between −78° C. to 100° C. in an organic solvent such as tetrahydrofuran or dimethyformamide.

Compounds of formula 25, 26 and 27 are either known compounds or may be formed from known compounds by known methods by a person skilled in the art.

Certain compounds of formula 22, 23 and 24 are novel compounds and as such form a further aspect of the invention.

Compounds of formula I where $R^2$ and $R^3$ are other than hydrogen may be made by routes described in WO03/106457. Thus for example a compound of formula 26a or 36a which are compounds of formula 26 or 36 respectively wherein the carbon atom adjacent to the leaving group X carries groups $R^2$ and $R^3$ may be converted to compounds of formula I using the methods described for converting compounds of 26 or 36 respectively into compounds of formula I.

Compounds where the ring T is a heteroaromatic ring (such as pyrimidine or thiophene) may be prepared according to the synthetic routes described for instance in Organic Reactions (New York) (2002), 60, 157,either by route shown in scheme V or scheme VI (both based on intramolecular Heck reactions):

Scheme V

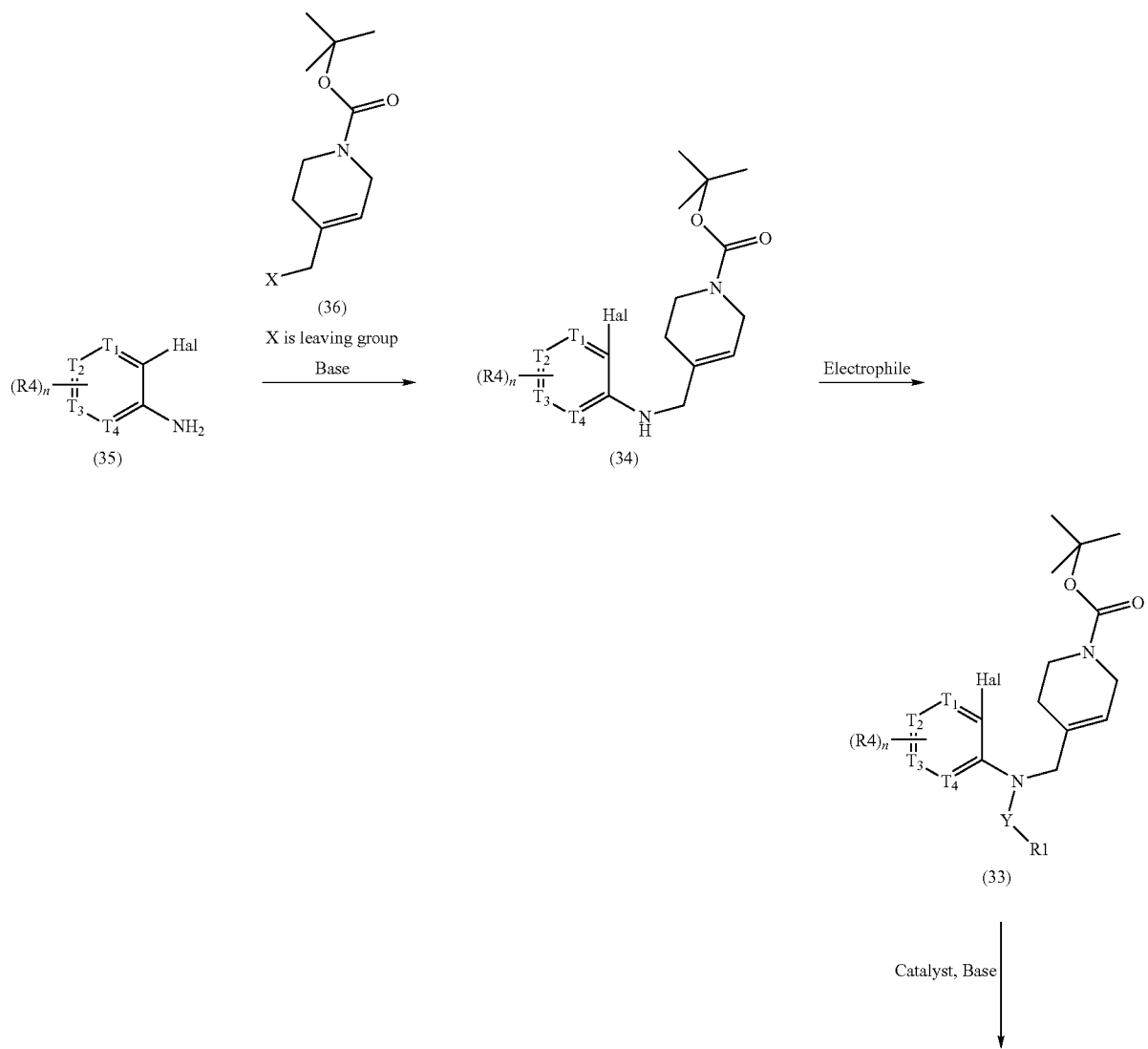

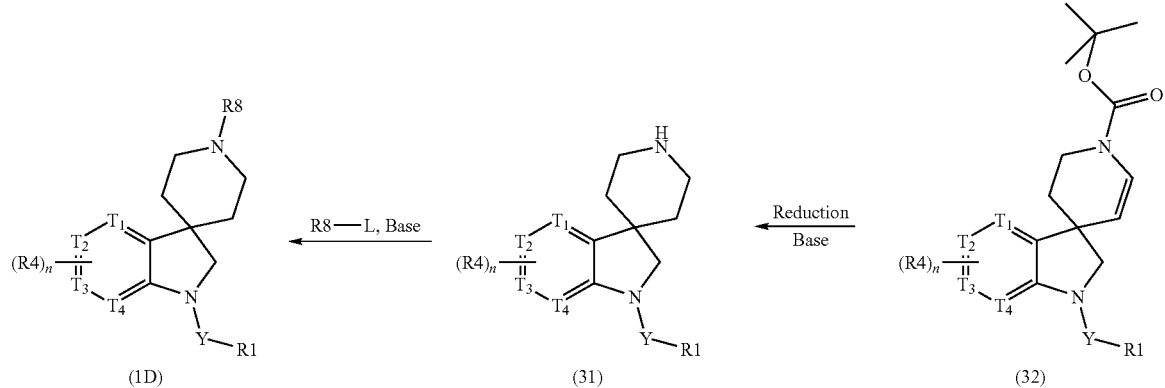
Scheme VI
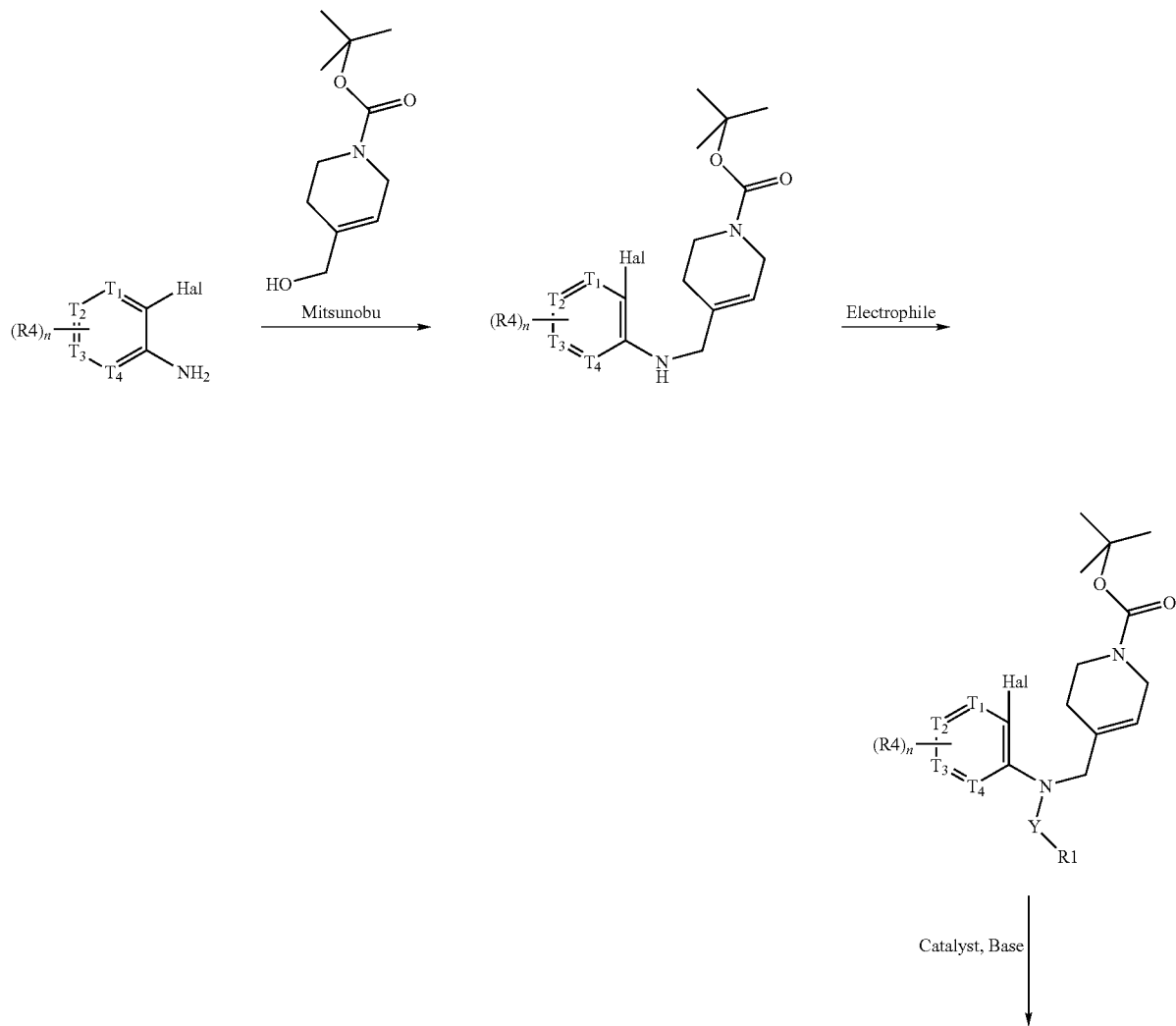

-continued

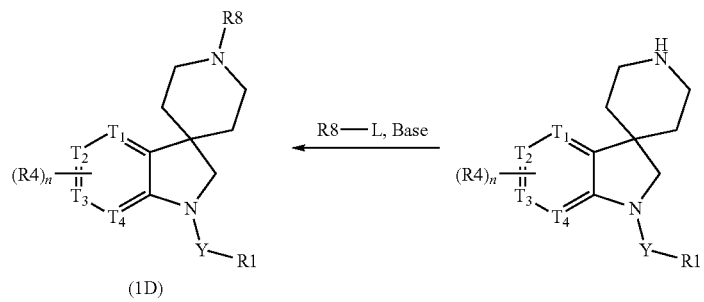

(1D)

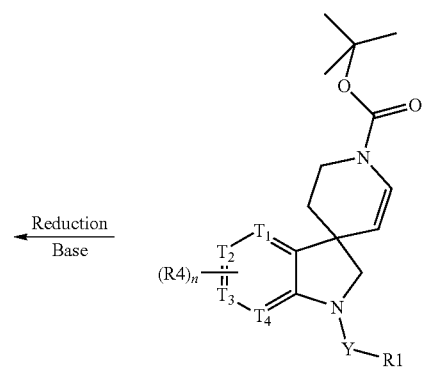

The above methods, particularly scheme V may be varied according to the knowledge of the skilled person. Thus for example compounds of formula 1 where the ring T is a thiophene ring may be synthesised by the method outlined in Scheme VII.

Thus, a compound of formula 1D may be synthesised by alkylating a compound of formula 42 with a reagent of formula R8-L by methods known per se.

A compound of formula 42 may be obtained by reacting a compound of formula 43 with a reducing agent such as triethylsilane, sodium borohydride, sodium cyanoborohydride or borane in the presence of an acid such as trifluoroacetic acid in an organic solvent such as dichloromethane at a temperature of between −10° C. to 80° C.

A compound of formula 43 may be synthesised from a compound of formula 44 by reacting with a suitable electrophilic species by methods known per se.

A compound of formula 44 may be prepared from a compound of formula 45 by treatment with a suitable base such as potassium carbonate at a temperature of between 0° C. to 80° C. in an organic solvent such as methanol or ethanol in combination with water.

A compound of formula 45 may be synthesised by cyclising a compound of formula 46 under Heck conditions, typically in the presence of a catalyst such as palladium(II) acetate, optionally a ligand such as triphenylphosphine or/and an additive such as tetrabutylammonium bromide and a base such as triethylamine in an organic solvent such as tetrahydrofuran, acetonitrile, dimethylformamide, N-methyl-pyrrolidinone or dimethylacetamide at a temperature of between 20° C. to 140° C.

Compounds of formula 46 may be synthesised by coupling compounds of formula 47 with the known alcohol 8 (*J. Org. Chem.* 2001, 66, 5545-5551) under Mitsunobu conditions, typically using a phosphine such as triphenylphosphine and an azo compound such as diethylazodicarboxylate or diisopropylazodicarboxylate in an organic solvent such as tetrahydrofuran or toluene at a temperature of between 0° C. to 80° C.

Compounds of formula 46 and 47 are either known compounds or may be formed from known compounds by known methods by a person skilled in the art.

Certain compounds of formula 42, 43 and 44 are novel compounds and as such form a further aspect of the invention.

SCHEME VII

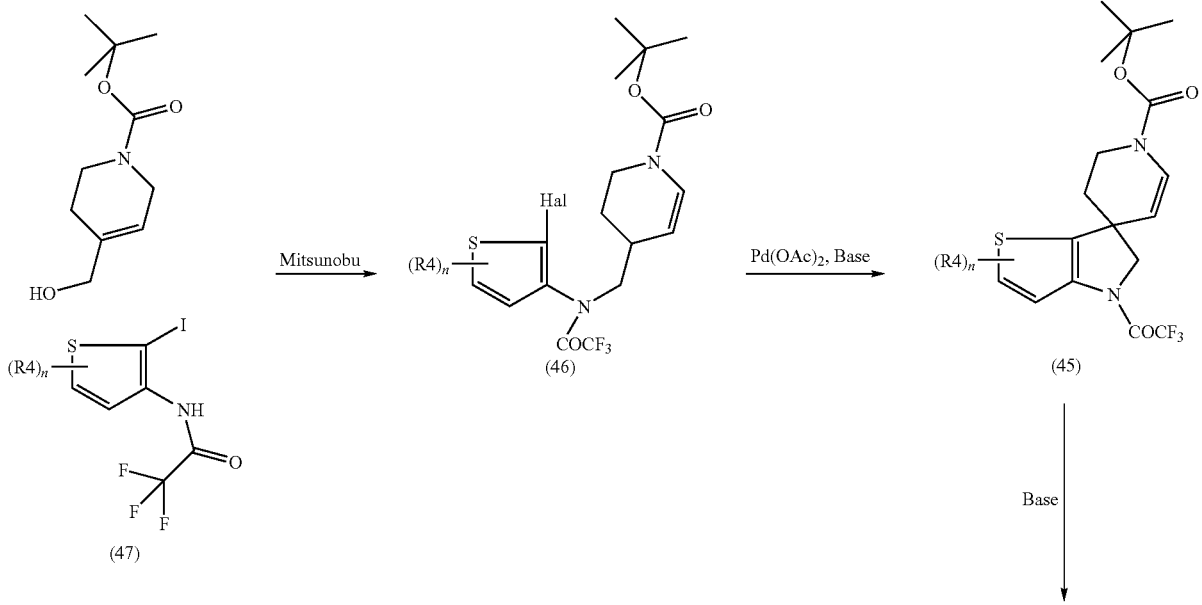

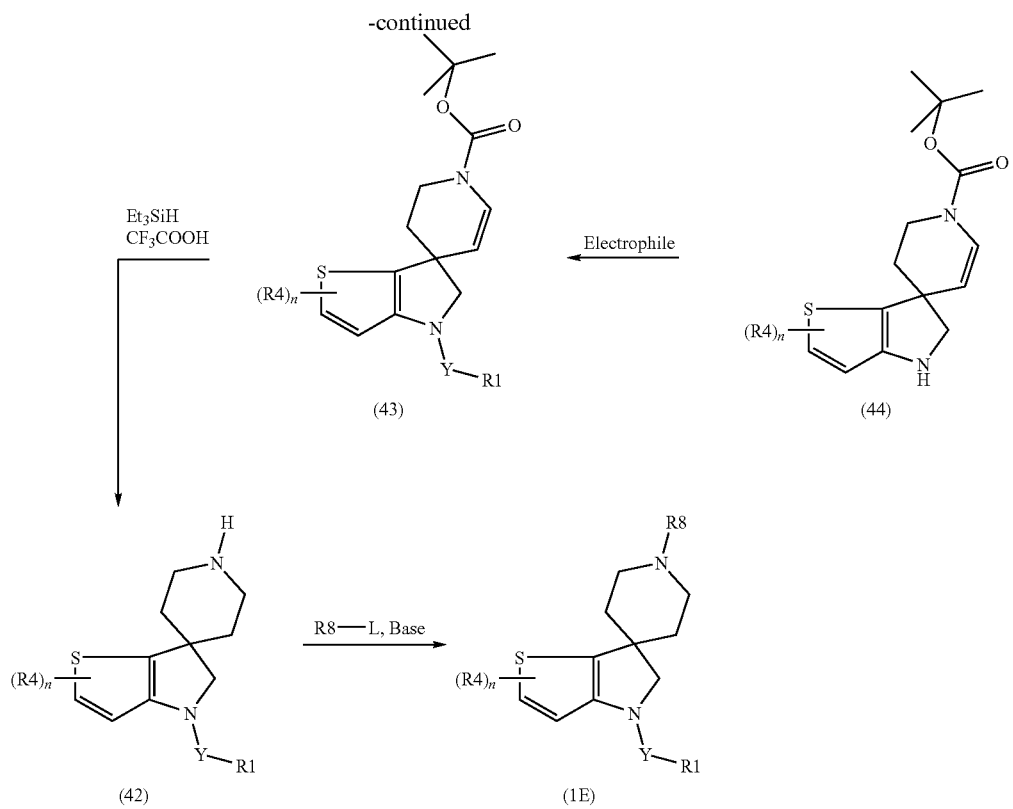

The skilled person will readily recognize that other compounds of formula 1 may be prepared using the methods described in Scheme VII.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinolarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp.(citrus nematodes), *Haemonchus contortus* (barber pole worm), *Caenorhabditis elegans* (vinegar eelworm), *Trichostrongylus* spp. (gastro intestinal nematodes) and *Deroceias reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest, The compounds of formula (I) are preferably used against insects, acarines or nematodes.

The term "plant" as used herein includes seedlings, bushes and trees.

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.0001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I). The compounds of formula (I) are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or, by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chliordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr; or q) Pymetrozine.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulphonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-S-benzyl thiophosphate, dimnefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)—N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-A1, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamrine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples:

EXAMPLE 1

This example illustrate the preparation of compound CCCIII-3, 7-aza-1-(2-chloropyridin-4-yl-)carbonyl-1'-[trans-3-(4-chlorophenylallyl]spiro[indoline-3,4'-piperidine]

Step A:
NaH (4.25 g) was slowly added to a solution of 3-chloro-2-pyridylacetonitrile (10 g) in DMSO (140 ml) under nitrogen. The mixture was stirred at room temperature for 1 h. A solution of bis-(2-chloro-ethyl)-carbamic acid tert-butyl ester (15.87 g) in DMSO (140 ml) was added and the resulting mixture was stirred at 70° C. for 2 hrs. After cooling, the reaction mixture was partitioned between ethyl acetate and water, the combined organic layers were washed with saturated sodium bicarbonate and brine, dried (sodium sulfate), filtered and concentrated in vacuo. The crude product was purified by chromatography [SiO$_2$; ethyl acetate-hexane (3:7)] to give 12.96 g (61%) of 2-chloro-4'-cyano-3',4',5',6'-tetrahydro-2'H-[3,4']bipyridinyl-1'-carboxylic acid tert-butyl ester as a white solide; MS (ES+) 322/324 (M+H$^+$).

Step B:
A mixture of 2-chloro-4'-cyano-3',4',5',6'-tetrahydro-2'H-[3,4']bipyridinyl-1'-carboxylic acid tert-butyl ester (6 g) and lithium tri-tert-butoxyaluminohydride (72.34 ml), 1M solution in THF) in 1-4-dioxane (90 ml) was refluxed overnight. After cooling, 1 N NaOH (100 ml) and H$_2$O (100 ml) were added slowly at 0° C. Dichloromethane was added to the mixture. The aqueous phase was extracted twice with dichloromethane and the combined organic layers were washed with saturated sodium bicarbonate, dried (magnesium sulfate), filtered and concentrated in vacuo. The crude product was purified by chromatography [SiO$_2$; dichloromethane-methanol (95:5)] to give 5.5 g (46%) of 7-Aza- spiro[indoline-3,4'-piperidine]-1'-carboxylic acid tert-butylester; MS (ES+) 290 (M+H$^+$).

Step C:
A mixture of 2-chloro-isonicotinic acid (441 mg), thionyl chloride (0.6 ml), DMF (trace) in toluene (9 ml) was heated to reflux for 2 hrs. After concentration in vacuo, the residue was dissolved in 12 ml dichloromethane and added dropwise at 0° C. under nitrogen to a mixture of 7-aza- spiro[indoline-3,4'-piperidine]-1'-carboxylic acid tert-butylester, (405 mg), triethylamine (0.86 ml) and dichloromethane ((12 ml). The mixture was stirred at room temperature for 2 hrs. The mixture was diluted in a saturated sodium carbonate solution. The organic layer was separated and the aqueous phase was extracted twice with dichloromethane and the combined organic layers were washed with saturated sodium bicarbonate, dried (magnesium sulfate), filtered and concentrated in vacuo 630 mg of 7-Aza-1-(2-chloropyridin-4-yl-)carbonyl-1'-carboxylic acid tert-butylester spiro[indoline-3,4'-piperidine; MS (ES+) 429 (M+H$^+$).

Step D:
Trifluoroacetic acid (1.92 ml) was added to a stirred solution of 7-Aza-1-(2-chloropyridin-4-yl-)carbonyl-1'-carboxylic acid tert-butylester spiro[indoline-3,4'-piperidine] (0.62 g) in anhydrous dichloromethane (20 ml) under an atmosphere of nitrogen. The reaction was left as such for 2 h. The reaction was washed with saturated bicarbonate solution and dried over sodium sulphate and concentrated in vacuo to yield 427 mg (90%) of 7-aza-1-(2-chloropyridin-4-yl-)carbonyl-spiro[indoline-3,4'-piperidine]; MS (ES+) 329 (M+H+).

Step E:
A solution of 4-chlorocinnamyl chloride (68 mg) in acetonitrile (4 ml) was added slowly to a stirred mixture of 7-Aza-1-(2-chloropyridin-4-yl-)carbonyl-spiro[indoline-3,4'-piperidine]; (100 mg) and potassium carbonate (0.42 g) in acetonitrile (16 ml) under an atmosphere of nitrogen at room. The reaction was heated to 70° C. for 2 hrs. The reaction was diluted in diethylether, washed with H$_2$O and dried over sodium sulphate and concentrated in vacuo. The crude product was purified by chromatography [SiO$_2$; hexane-ethyl acetate-triethylamine (2:8:0.1)] to give 84 mg (58%) of 7-aza-1-(2-chloropyridin-4-yl-)carbonyl-1-[trans-3-(4-chlorophenylallyl]spiro[indoline-3,4'-piperidine]; MS (ES+) 479 (M+H+). Compound Nos CCCI-3, CCCV-3 and CCCVI-3 were prepared by analogous methods to those of Example 1.

EXAMPLE 2

This Example illustrates the preparation of compound CCIII-3, 6-Aza-1-(2-chloropyridin-4-yl-)carbonyl-1'-[trans-3-(4-chlorophenylallyl]spiro[indoline-3,4'-piperidine].

Step A:
Potassium hexamethyldisilazane (1.2 ml, 0.5 M solution in toluene) was slowly added to a solution of 4-chloro-3-fluoro-pyridin (0.5 g) and N-Boc-4-Cyano-Piperidine (0.312 g) in 1.5 ml toluene at room temperature, under nitrogen. The mixture was stirred at 80° C. for 2 hrs. After cooling, the reaction mixture was quenched in 1N HCl. The aqueous phase was extracted twice with toluene and the combined organic were dried over anhydrous magnesium sulfate and concentrated in vacuo. The crude product was purified by chromatography [SiO$_2$; ethyl acetate-hexane (1:1)] to give 104 mg (90%) of 4-cyano-3'-fluoro-3,4,5,6-tetrahydro-2H-[4,4']bipyridinyl-1-carboxylic acid tert-butyl ester; MS (ES+) 306 (M+H$^+$).

Step B:

A mixture of 4-cyano-3'-fluoro-3,4,5,6-tetrahydro-2H-[4,4']bipyridinyl-1-carboxylic acid tert-butyl ester (1 g) and lithium tri-tert-butoxyaluminohydride (12.7 ml), 1M solution in THF) in 1-4-dioxane (15 ml) was stirred at 130° C. (sealed tube) for 1 hr. After cooling, 1 N NaOH (100 ml) and H$_2$O (100 ml) were added slowly at 0° C. Ethyl acetate was added to the mixture. The aqueous phase was extracted twice with ethyl acetate and the combined organic layers were washed with saturated sodium bicarbonate, dried (magnesium sulfate), filtered and concentrated in vacuo. The crude product was purified by chromatography [SiO$_2$; hexane-ethyl acetate (7:3)] to give 230 mg g (24%) of 6-aza-spiro[indoline-3,4'-piperidine]-1'-carboxylic acid tert-butylester; MS (ES+) 290 (M+H$^+$).

Step C:

A mixture of 2-chloro-isonicotinic acid (239 mg), thionyl chloride (0.33 ml), DMF (trace) in toluene (5 ml) was heated to reflux for 2 hrs. After concentration in vacuo, the residue was dissolved in 2 ml dichloromethane and added dropwise at 0° C. under nitrogen to a mixture of 6-aza-spiro[indoline-3,4'-piperidine]-1'-carboxylic acid tert-butylester, (220 mg), triethylamine (0.47 ml) and dichloromethane ((13 ml). The mixture was stirred at room temperature for 1 hr. The mixture was diluted in a saturated sodium carbonate solution. The organic layer was separated and the aqueous phase was extracted twice with dichloromethane and the combined organic layers were washed with saturated sodium bicarbonate, dried (magnesium sulfate), filtered and concentrated in vacuo 340 mg of 6-aza-1-(2-chloropyridin-4-yl-)carbonyl-1'-carboxylic acid tert-butylester spiro[indoline-3,4'-piperidine]; MS (ES+) 429 (M+H$^+$).

Step D:

Trifluoroacetic acid (1 ml) was added to a stirred solution 6-aza-1-(2-chloropyridin-4-yl-)carbonyl-1'-carboxylic acid tert-butylester spiro[indoline-3,4'-piperidine] (0.33 g) in anhydrous dichloromethane (10 ml) under an atmosphere of nitrogen. The reaction was left as such for 2 h. The reaction was washed with saturated bicarbonate solution and dried over sodium sulphate and concentrated in vacuo to yield 210 mg (83%) of 4-aza-1-(2-chloropyridin-4-yl-)carbonyl-spiro[indoline-3,4'-piperidine]; MS (ES+) 329 (M+H$^+$).

Step E:

A solution of 4-chlorocinnamyl chloride (40 mg) in acetonitrile (3 ml) was added slowly to a stirred mixture of 4-aza-1-(2-chloropyridin-4-yl-)carbonyl-spiro [indoline-3,4'-piperidine] (100 mg) and N,N-diisopropyl-ethylamine (0.66 ml) in acetonitrile (13 ml) under an atmosphere of nitrogen at room. The reaction was stirred at room temperature for 2 hrs, heated to reflux for 2 hrs and then stirred overnight at room temperature. The reaction was diluted in diethylether, washed with H$_2$O, then with brine and dried over sodium sulphate and concentrated in vacuo. The crude product was purified by chromatography [SiO$_2$; ethyl acetate-methanol-triethylamine (9:10:0.1)] to give 72 mg (76% over 3 steps) of 6-aza-1-(2-chloropyridin-4-yl-)carbonyl-1'-[trans-3-(4-chlorophenylallyl]spiro[indoline-3,4'-piperidine];

MS (ES+) 479 (M+H$^+$).

Compound Nos CCIII-6 and CCIII7 were prepared by analogous methods to those of Example 2.

EXAMPLE 3

This Example illustrates the preparation of compound III-210, 6-chloro-4-aza-1-(2-chloropyridin-4-yl-)carbonyl-1'-[trans-3-(4-chlorophenylallyl]spiro [indoline-3,4'-piperidine]

Step A:

Potassium hexamethyldisilazane (1.34 ml, 0.5 M solution in toluene) was slowly added to a solution of 5-Chloro-2,3-difluoro-pyridine (0.1 g) and N-Boc-4-Cyano-Piperidine (0.14 g) in 3 ml toluene at 0° C., under nitrogen. The mixture was stirred at 0° C. for 1 hr. After cooling, the reaction mixture was quenched in 1N HCl. The aqueous phase was extracted twice with ethyl acetate and the combined organic were washed with water, dried over anhydrous sodium sulfate and concentrated in vacuo. The crude product was purified by chromatography [SiO$_2$; hexane-ethyl acetate-hexane (4:1)] to give 111 mg (49%) of 5-chloro-4'-cyano-3-fluoro-3',4',5',6'-tetrahydro-2'H-[2,4']bipyridinyl-1'-carboxylic acid tert-butyl ester; MS (ES+) 240 (M-Boc+H+).

Step B:

A mixture of 5-chloro-4'-cyano-3-fluoro-3',4',5',6'-tetrahydro-2'H-[2,4']bipyridinyl-1'-carboxylic acid tert-butyl ester (0.05 g) and lithium tri-tert-butoxyaluminohydride (0.57 ml), 1M solution in THF) in 1-4-dioxane (0.75 ml) was refluxed under nitrogen for 4 hrs. After cooling, 1 N NaOH and H$_2$O and ethyl acetate were added slowly to the mixture at 0° C. The aqueous phase was extracted twice with ethyl acetate and the combined organic layers were washed with saturated sodium bicarbonate, dried (sodium sulfate), filtered and concentrated in vacuo. The crude product was purified by chromatography [SiO$_2$; hexane-ethyl acetate-triethylamine (75:25:1)] to give 18 mg g (38%) of 6-chloro-4-aza-spiro [indoline-3,4'-piperidine]-1'-carboxylic acid tert-butylester; MS (ES+) 324 (M+H$^+$).

Step C:

A mixture of 2-chloro-isonicotinic acid (324 mg), thionyl chloride (0.43 ml), DMF (trace) in toluene (6.4 ml) was heated to reflux for 2 hrs. After concentration in vacuo, the residue was dissolved in 2 ml dichloromethane and added dropwise at 0° C. under nitrogen to a mixture of 6-chloro-4-aza-spiro[indoline-3,4'-piperidine]-1'-carboxylic acid tert-butylester, (220 mg), triethylamine (0.6 ml) and dichloromethane ((20 ml). The mixture was stirred at room temperature for 1 hr. The mixture was diluted in a saturated sodium carbonate solution. The organic layer was separated and the aqueous phase was extracted twice with dichloromethane and the combined organic layers were washed with saturated sodium bicarbonate, dried (magnesium sulfate), filtered and concentrated in vacuo 473 mg (102%) of 6-chloro-4-aza-1-(2-chloropyridin-4-yl-)carbonyl-1'-carboxylic acid tert-butylester spiro[indoline-3,4'-piperidine];
MS (ES+) 407 (M–Me2C=CH2+H$^+$).

Step D:

Trifluoroacetic acid (1.47 ml) was added to a stirred solution 6-chloro-4-aza-1-(2-chloropyridin-4-yl-)carbonyl-1'-carboxylic acid tert-butylester spiro[indoline-3,4'-piperidine] (0.47 g) in anhydrous dichloromethane (15 ml) under an atmosphere of nitrogen. The reaction was left as such for 1 hr. The reaction was washed with saturated bicarbonate solution and dried over sodium sulphate and concentrated in vacuo to yield 363 mg (98%) of 6-chloro-4-aza-1-(2-chloropyridin-4-yl-)carbonyl-spiro[indoline-3,4'-piperidine]; MS (ES+) 363 (M+H$^+$).

Step E:

A solution of 4-chlorocinnamyl chloride (165 mg) in acetonitrile (20 ml) was added slowly to a stirred mixture of 6-chloro-4-aza-1-(2-chloropyridin-4-yl-)carbonyl-spiro[indoline-3,4'-piperidine] (300 mg) and N,N-diisopropyl-ethylamine (0.66 ml) in acetonitrile (40 ml) under an atmosphere of nitrogen at room. The reaction was stirred at room temperature for 4 hrs and heated to reflux overnight. The reaction was diluted in diethylether, washed with $H_2O$, then with brine and dried over sodium sulphate and concentrated in vacuo. The crude product was purified by chromatography [$SiO_2$; hexane-ethyl acetate-triethylamine (8:2:0.1)] to give 310 mg (73%) of 6-chloro-4-aza-1-(2-chloropyridin-4-yl-)carbonyl-1'-[trans-3-(4-chlorophenylallyl]spiro[indoline-3,4'-piperidine]; MS (ES+) 513 (M+H$^+$).

Compound Nos I-26, I-29, I-30, I-210, I-213, I-214, I-233, I-237, II-26, II-29, II-30, II-210, II-213, II-214, III-3, III-6, III-7, III-26, III-29, III-30, III-210, III-210 N-oxide, III-213, III-214, III-233, III-236, III-237, III-302, III-325, III-328, III-329, V-26, V-29, V-30, V-209, V-210, V-213, V-214, V-233, V-236, V-237, V-509, VIII-26, VIII-29, VIII-30, VIII-210, VIII-213, VIII-214, XX-26, XX-29, XX-30, XX-210, XX-213, XX-214, XX-233, XX-236, XX-237, CIII-49, CIII-52, CIII-53, CIII-210, CIII-214, CIII-555, CCCI-3, CCCIII-26, CCCIII-29, CCCIII-30, CCCV-26, CCCV-29 and CCCV-30 were prepared by analogous methods to those of Example 3.

EXAMPLE 4

This Example illustrates the preparation of compound DCIII-3, 4-(2-chloropyridin-4-yl)carbonyl-1'-[trans-3-(4-chlorophenyl)allyl]spiro[5,6-dihydro-4H-thieno[3,2-b]pyrrole-6,4'-piperidine)]

Step A: Triphenylphosphine (2.29 g) was dissolved in tetrahydrofuran (50 ml) and the solution was cooled to –10° C. under argon. Diisopropylazodicarboxylate (1.70 ml) was added dropwise over 10 min and the resulting mixture was stirred at –10° C. for 20 min (formation of a white precipitate). 2,2,2-Trifluoro-N-(2-iodo-thiophen-3-yl)-acetamide (2.25 g) dissolved in a minimum volume of tetrahydrofuran was added, followed by 4-Hydroxymethyl-3,6-dihydro-2H-pyridine-1-carboxylic acid tert-butyl ester (*J. Org. Chem.* 2001, 66, 5545-5551, 1.49 g) dissolved in a minimum volume of tetrahydrofuran. The reaction mixture was allowed to warm to room temperature and stirred for 12 hours. The solution was then concentrated in vacuo and the residue subjected to silica gel chromatography (cyclohexane:ethyl acetate 93:7) to afford 4-{[(2-Iodo-thiophen-3-yl)-(2,2,2-trifluoro-acetyl)-amino]-methyl}-3,6-dihydro-2H-pyridine-1-carboxylic acid tert-butyl ester as a colourless oil (2.27 g). $^1$H NMR (400 MHz, CDCl$_3$) 1.5 (s, 9H), 2.15 (m, 2H), 3.43 (m, 1H), 3.52 (m 1H), 3.75 (d, J=19 Hz, 1H), 3.77 (m, 2H), 4.76 (d, J=17 Hz, 1H), 5.41 (s, 1H), 6.68 (br d, J=5.5 Hz, 1H), 7.42 (d, J=5.5 Hz, 1H); MS (ES+) 417 (M+H$^+$—CO$_2$-isobutene), 458 (M+H$^+$-isobutene).

Step B: In a dried, argon purged flask,-{[(2-Iodo-thiophen-3-yl)-(2,2,2-trifluoro -acetyl)-amino]-methyl}-3,6-dihydro-2H-pyridine-1-carboxylic acid tert-butyl ester obtained in Step A (1.57 g) was dissolved in dimethylacetamide (25 ml); triethylamine (1.05 ml), tetrabutylammonium bromide (1.08 g) and palladium(II) acetate (103 mg) were successively added and the solution was heated at 80° C. for 4 hours. Palladium(II) acetate (20 mg) was added again and the mixture stirred at 80° C. for 3 more hours. After cooling to room temperature, the reaction mixture was diluted with ethyl acetate, washed with brine, dried over sodium sulphate and concentrated in vacuo. Silica gel chromatography of the residue (cyclohexane:ethyl acetate 8:2) afforded 4-trifluoroacetyl-spiro[5,6-dihydro-4H-thieno[3,2-b]pyrrole-6,4'-(1', 2',3',4'-tetrahydropyridine)]-1' carboxylic acid tert-butyl ester (0.9 g). $^1$H NMR (40 MHz, CDCl$_3$) 2 rotamers: 1.54 (s, 9H), 2.05 (m, 2H), 3.65-3.80 (m, 2H), 4.20-4.30 (m, 2H), 4.70 and 4.80 (m, 1H), 6.82 and 6.96 (m, 1H), 7.23 (d, J=5.5 Hz, 1H), 7.42 (d, J=5.5 Hz, 1H); MS (ES+) 288 (M+H$^+$-isobutene).

Step C: 4-trifluoroacetyl-spiro[5,6-dihydro-4H-thieno[3, 2-b]pyrrole-6,4'-(1',2',3',4', -tetrahydropyridine)]-1' carboxylic acid tert-butyl ester obtained in Step B (0.9 g) was dissolved in methanol (30 ml) and water (5 ml), placed under argon and potassium carbonate (28 g) was added. The reaction mixture was stirred for 10 min at room temperature, the mixture was filtered and the filtrate concentrated in vacuo. The residue was diluted with ethyl acetate, washed with brine, dried (sodium sulphate) and concentrated in vacuo. The residue was immediately dissolved in dichloromethane (40 ml) and acylated with 2-chloroisonicotinoyl chloride (800 mg) in the presence of triethylamine (1 ml) at 0° C. for 1 hour. Standard aqueous work-up and silica gel chromatography (cyclohexane:ethyl acetate 8:2) afforded 4-(2-chloropyridin-4-yl)carbonyl-spiro[5,6-diydro-4H-thieno[3,2-b]pyrrole-6, 4'-(1',2',3',4'-tetrahydropyridine)]-1' carboxylic acid tert-butyl ester (0.83 g). M.p. 63-65° C.; MS (ES+) 332/334 (M+H$^+$—CO$_2$-isobutene), 376/378 (M+H$^+$-isobutene), 432/434 (M+H$^+$).

Step D: 4-(2-chloropyridin-4-yl)carbonyl-spiro[5,6-dihydro-4H-thieno[3,2-b]pyrrole-6,4'-(1',2',3',4'-tetrahydropyridine)]-1' carboxylic acid tert-butyl ester obtained in Step C (216 mg) was dissolved in dichloromethane (15 ml) and treated successively with triethylsilane (0.4 ml) and trifluoroacetic acid (0.75 ml); the solution was stirred under argon for 6 hours, diluted with dichloromethane, neutralised with aqueous sodium bicarbonate, dried (sodium sulphate) and concentrated in vacuo. The residue was dissolved in acetonitrile (15 ml) and treated with diisopropylethylamine (0.14 ml) and 4-chlorocinnamyl chloride (96 mg) for 24 hours at room temperature. Standard aqueous work-up afforded a residue which was purified by flash chromatography (silica gel, cyclohexane:ethyl acetate 8:2+0.5% triethylamine) to give the title product (170 mg) as a colourless solid. M.p. 81-82° C.; $^1$H NMR (600 MHz, CDCl$_3$) 2 rotamers: 1.81-1.94 (m, 4H), 2.60-2.71 (m, 4H), 3.21 and 3.23 (d, J=7 Hz, 2H), 4.03 and 4.35 (s, 2H), 5.63 and 7.55 (d, J=5.9 Hz, 1H), 6.2 and 6.29 (dt, J=12.9 Hz, 7 Hz, 1H), 6.51 and 6.53 (d, J=12.9 Hz, 1H), 6.96 and 7.23 (d, J=5.9 Hz, 1H), 7.26-7.49 (m, 6H), 8.53 and 8.54 (d, J=5.9.Hz, 1H); $^{13}$C NMR (125 MHz, CDCl$_1$CDCl$_2$, 80° C.) selected data 37.3, 51.0, 61.1, 67.1 and 77.2, 114.4 and 117.5, 120.3, 122.3, 127.1, 127.5, 127.9, 128.8, 132.0, 150.6; MS (ES+) 484/486/487/489 (M+H$^+$).

Compound Nos DCIII-3, DCIII-6, DCIII-7, DCIII-52, DCIII-53 and DCV-53. were prepared by analogous methods to those of Example 4.

EXAMPLE 5

This Example illustrates the preparation of compound CIII-210, 4-chloro-5-aza-1 -(2-chloropyridin-4-yl)carbonyl-1'-[trans-3-(4-chlorophenyl)allyl] spiro[indoline-3,4'-piperidine]

Step A:2-Chloro-4-amino-pyridine was brominated according to the method described in *Synthesis* 2001, 14, 2175-2179: a solution of 4-chloro-4-amino-pyridine (12.3 g) in acetonitrile (500 ml) was treated with N-bromosuccinimide (17.8 g) and the resulting solution was stirred at room temperature for 24 hours. The solution was then concentrated in vacuo and the residue subjected to silica gel chromatography (cyclohexane:ethyl acetate 8:2) to afford 3-bromo-2-chloro-4-aminopyridine (12.2 g, m.p. 146° C. (hexane/ether)) and 5-bromo-2-chloro-4-aminopyridine (2.9 g, m. p. 117-119° C.).

Step B: Lithium bis(trimethylsilyl)amide (1M solution in THF, 5.1 ml) was added dropwise to a stirred solution of 3-bromo-2-chloro-4-aminopyridine (1.04 g) in tetrahydrofuran (15 ml) at −78° C. under $N_2$. The resulting solution was then stirred at room temperature for 30 min., warmed to 0° C. then cooled again at −78° C. 4-Chloromethyl-3,6-dihydro-2H-pyridine-1-carboxylic acid tert-butyl ester (1.16 g, prepared according to WO 98/25605) dissolved in a minimum volume of THF was added dropwise then the solution was refluxed for 14 hours. The reaction mixture was cooled to room temperature, poured into diluted aqueous ammonium chloride, extracted with EtOAc. The organic layer was washed with brine, dried over sodium sulfate and concentrated in vacuo. The residue was purified by silica gel chromatography ($CH_2Cl_2$ then $CH_2Cl_2$/EtOAc 8:2 cyclohexane:ethyl acetate 8:2) to afford 4-[(3-bromo-2-chloro-pyridin-4-ylamino)-methyl]-3,6-dihydro-2H -pyridine-1-carboxylic acid tert-butyl ester (1.42 g), which was identified by its mass and 1H NMR spectra. MS (ES+) 346/348/350 ($MH^+$-isoprene), 402/404/406 ($MH^+$).

Step C: Lithium bis(trimethylsilyl)amide (1M solution in THF, 3 ml) was added dropwise to a stirred solution of 4-[(3-Bromo-2-chloro-pyridin-4-ylamino)-methyl]-3,6-dihydro-2H-pyridine-1-carboxylic acid tert-butyl ester (0.53 g) in tetrahydrofuran (20 ml) at −78° C. under $N_2$. The yellow solution was warmed to 0° C. and then 2-chloroisonicotinoyl chloride (50% solution in toluene, 0.95 g) was added. The solution was stirred at 0° C. for 10 min., quenched by addition of aqueous ammonium chloride, extracted with EtOAc, dried ($Na_2SO_4$) and concentrated in vacuo. The residue was purified by silica gel chromatography ($CH_2Cl_2$ then $CH_2Cl_2$/EtOAc 8:2 cyclohexane:ethyl acetate 8:2) to afford 4-{[(3-bromo -2-chloro-pyridin-4-yl)-(2-chloro-pyridine-4-carbonyl)-amino]-methyl }-3,6-dihydro-2H -pyridine-1-carboxylic acid tert-butyl ester (0.63 g), which was identified by its mass and 1H NMR spectra. MS (ES+) 443/445 ($MH^+$—BOC), 484/486 ($MH^+$-isoprene).

Step D: In a dried, argon purged flask, 4- {[(3-bromo-2-chloro-pyridin-4-yl)-(2-chloro-pyridine-4-carbonyl)-amino]-methyl}-3,6-dihydro-2H-pyridine-1-carboxylic acid tert -butyl ester obtained in Step C (0.63 g) was dissolved in dimethylacetamide (10 ml); triethylamine (0.41 ml), tetrabutylammonium bromide (0.40 g) and palladium(II) acetate (40 mg) were successively added and the solution was heated at 90° C. for 18 hours. After cooling to room temperature, the reaction mixture was diluted with diethyl ether, washed with brine, dried over sodium sulphate and concentrated in vacuo. Silica gel chromatography of the residue (cyclohexane:ethyl acetate 8:2) afforded 1-(2-chloro-pyridine-4-carbonyl)-spiro [[(4-chloro-2,3-dihydro-1H-pyrrolo[3,2-c]pyridine)-3,4'-(1', 2',3',4'-tetrahydropyridine)]-1'carboxylic acid tert-butyl ester (0.21 g), which was identified by its mass and 1H NMR spectra. MS (ES+) 461/463 ($MH^+$).

Step E:1 -(2-chloro-pyridine-4-carbonyl)-spiro[[(4-chloro-2,3-dihydro-1 H-pyrrolo [3,2-c]pyridine)-3,4'-(1',2', 3',4'-tetrahydropyridine)]-1'carboxylic acid tert -butyl ester obtained in Step D (0.19 g) was dissolved in dichloromethane (13 ml) and treated successively with triethylsilane (0.33 ml) and trifluoroacetic acid (0.63 ml); the solution was stirred under argon for 8 hours, diluted with dichlioromethane, neutralised with aqueous sodium bicarbonate, dried (sodium sulphate) and concentrated in vacuo. The residue was dissolved in acetonitrile (13 ml) and treated with diisopropylethylamine (0.12 ml) and 4-chlorocinnamyl chloride (84 mg) for 48 hours at room temperature. Standard aqueous work-up afforded a residue which was purified by flash chromatography (silica gel, cyclohexane:ethyl acetate 8:2+0.5% triethylamine) to give the title product (43 mg) as a colourless solid. M.p. 95-96° C.; MS (ES+) 513/515 ($M+H^+$).

Compound Nos CDIII-49, CDIII-52, CDIII-53, CDV-49, CDV-52, DIII-3, DIII-210, DV-3, DV-213 and DV-214 were prepared by analogous methods to those of Example 5.

EXAMPLE 6

This Example illustrates the pesticidal/insecticidal properties of compounds of formula (I).
Test against were performed as follows:

*Spodoptera littoralis* (Egyptian cotton leafworm)

Cotton leaf discs were placed on agar in a 24-well microtiter plate and sprayed with test solutions at an application rate of 200 ppm. After drying, the leaf discs were infested with 5 $L_1$ larvae. The samples were checked for mortality, repellent effect, feeding behaviour, and growth regulation 3 days after treatment (DAT). The following compounds gave at least 80% control of *Spodoptera littoralis*.

I-26, I-30, I-237, II-26, II-29, II-30, II-210, II-213, II-214, III-3, III-6, III-7, III-26, III-29, III-30, III-210, III-210 N-oxide, III-233, III-236, III-237, III-302, III-325, III-328, III-329, V-26, V-29, V-30, V-209, V-210, V-213, V-214, V-233, V-236, V-237, V-509, VIII-26, VIII-29, VIII-30, VIII-210, VIII-213, XX-26, XX-29, XX-30, XX-210, XX-214, XX-233, XX-236, XX-237, CIII-210, CIII-214, CCCIII-3, CCCIII-26, CCCV-3, CCCV-26, CCCVI-3, CDIII-49, CDIII-52, CDIII-53, CDV-49, CDV-52 and DV-3.

*Heliothis virescens* (Tobacco budworm):

Eggs (0-24 h old) were placed in 24-well microtiter plate on artificial diet and treated with test solutions at an application rate of 200 ppm by pipetting. After an incubation period of 4 days, samples were checked for egg mortality, larval mortality, and growth regulation. The following compounds gave at least 80% control of *Heliothis virescens*.

I-26, I-29, I-30, I-210, I-213, I-214, I-233, I-237, II-26, II-29, II-30, II-210, II-213, II-214, III-3, III-6, III-7, III-26, III-29, III-30, III-210, III-210 N-oxide, III -213, III-214, III-233, III-236, III-237, III-302, III-325, III-328, III-329, V-26, V-29, V-30, V-209, V-210, V-213, V-214, V-233, V-236, V-237, V-509, VIII-26, VIII-29, VIII-30, VIII-210, VIII-213, VIII-214, XX-26, XX-29, XX-30, XX-210, XX-213, XX-214, XX-233, XX-236, XX-237, CIII-49, CIII-52, CIII-53, CIII-210, CIII-214, CIII-555, CCIII-3, CCIII-6, CCIII-7, CCCI-3, CCCIII-3, CCCIII-26, CCCIII-29, CCCIII-30, CCCV-3, CCCV-26, CCCV-29, CCCV-30, CCCVI-3, CDIII-49, CDIII-52, CDIII-53, CDV-49, CDV-52, DIII-3, DIII-210, DV-3, DCIII-3, DCIII-7, DCIII-52 and DCV-53.

*Plutella xylostella* (Diamond back moth):

24-well microtiter plate (MTP) with artificial diet was treated with test solutions at an application rate of 18.2 ppm by pipetting. After drying, the MTP's were infested with larvae (L2) (10-15 per well). After an incubation period of 5 days, samples were checked for larval mortality, antifeedant and growth regulation. The following compounds gave at least 80% control of *Plutella xylostella*:

II-26, II-29, II-30, II-210, II-214, III-3, III-6, III-7, III-26, III-29, III-30, III-210, III-210 N-oxide, III-213, III-214, III-233, III-236, III-237, III-302, III-325, III-328, III-329, V-26, V-29, V-30, V-209, V-210, V-213, V-214, V-233, V-236, V-237, V-509, VIII-26, VIII-29, VIII-30, VIII-210, VIII-213, VIII-214, XX-26, XX-29, XX-30, XX-210, XX-213, XX-214, XX-233, XX-236, XX-237, CIII-49, CIII-52, CIII-53, CIII-210, CIII-214, CIII-555, CCIII-3, CCCIII-3, CCCIII-26, CCCIII-29, CCCV-3, CCCV-26, CCCV-29, CCCV-30, CCCVI-3, CDIII-49, CDIII-52, CDIII-53, CDV-52, DV-3, DV-213, DV-214, DCIII-53 and DCV-53.

*Myzus persicae* (Green peach aphid):

Sunflower leaf discs were placed on agar in a 24-well microtiter plate and sprayed with test solutions at an application rate of 200 ppm. After drying, the leaf discs were infested with an aphid population of mixed ages. After an incubation period of 6 DAT, samples were checked for mortality. The following compounds gave at least 80% control of *Myzus persicae*.

III-3, III-7, V-213, VIII-29, CCCIII-3, CCCV-3 and DCIII-3.

*Aedes aegypti* (Yellow fever mosquito):

10-15 Aedes larvae (L2) together with a nutrition mixture are placed in 96-well microtiter plates. Test solutions at an application rate of 2 ppm are pipetted into the wells. 2 days later, insects were checked for mortality and growth inhibition. The following compounds gave at least 80% control of *Aedes aegypt: i*

I-26, I-210, I-213, I-214, I-233, I-236, I-237, II-26, II-29, II-30, II-210, II-213, II-214, III-3, III-6, III-7, III-26, III-29, III-30, III-210, III-210 N-oxide, III -213, III -214, III-233, III-236, III-237, III-302, III-325, III-328, III-329, V-26, V-29, V-30, V-210, V-213, V-214, V-236, V-237, V-509, VIII-26, VIII-29, VIII-30, VIII-210, VIII-213, VIII-214, XX-26, XX-29, XX-30, XX-210, XX-213, XX-214, XX-233, XX-236, XX-237, CIII-52, CIII-53, CIII-210, CIII-214, CCIII-3, CCIII-6, CCIII-7, CCCI-3, CCCIII-3, CCCIII-26, CCCV-3, CCCIII-26, CCCVI-3, CDIII-49, CDIII-52, CDIII-53, CDV-49, CDV-52, DCIII-3, DCIII-6, DCIII-52, DCIII-53 and DCV-53.

*Diabrotica balteata* (Corn root worm):

A 24-well microtiter plate (MTP) with artificial diet was treated with test solutions at an application rate of 200 ppm (concentration in well 18 ppm) by pipetting. After drying, the MTP's were infested with larvae (L2) (6-10 per well). After an incubation period of 5 days, samples were checked for larval mortality, and growth regulation.

The following compounds gave at least 80% control of *Diabrotica balteata*:

II-29, II-30, III-29, III-30, III-213, III-236, III-237, V-26, V-29, V-30, V-210, V-213, V-214, V-236, V-237, VIII-29, VIII-30, XX-30, XX-237, CIII-52, CIII-210, CIII-214, CCCIII-29, CCCIII-30, CCCV-3, CCCV-26, CCCV-29, CCCV-30, CDIII-49, CDIII-52, CDIII-53, CDV-49, CDV-52, DV-3, DV-210, DV-213, DCIII-6, DCIII-7 and DCV-53.

The invention claimed is:

1. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula I

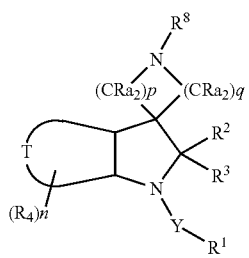

(I)

wherein Y is a single bond, CO=O, C=S or $S(O)_m$ where m is 0, 1 or 2;

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$ where $R^{13}$ and $R^{14}$ are independently hydrogen, $COR^{15}$, optionally substituted alkyl, optionally substituted aryl, optionally substituted heteroaryl, optionally substituted heterocyclyl or $R^{13}$ and $R^{14}$ together with the N atom to which they are attached form a group $-N=C(R^{16})-NR^{17}R^{18}$; $R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$; $R^{16}$, $R^{17}$ and $R^{18}$ are each independently H or lower alkyl; $R^{19}$ and $R^{20}$ are independently optionally substituted alkyl, optionally substituted aryl or optionally substituted heteroaryl;

$R^2$ and $R^3$ are independently hydrogen, halogen, cyano, optionally substituted alkyl, optionally substituted alkoxy or optionally substituted aryl;

the ring

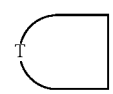

is a 6 membered heteroaromatic ring,

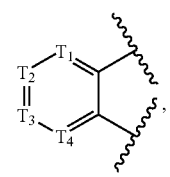

wherein T1 represents N, and each of T2, T3, and T4 represent C;

each $R^4$ is independently halogen, nitro, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or $R^{21}R^{22}N$ where $R^{21}$ and $R^{22}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{21}$ and $R^{22}$ together with the N atom to which they are attached form a five, six or seven-membered heterocyclic ring which may contain one or two further heteroatoms selected from O, N or S and which may be optionally substituted by one or two $C_{1-6}$ alkyl groups, or 2 adjacent groups $R^4$ together with the carbon atoms to which they are attached form a 4, 5, 6, or 7 membered carbocyclic or heterocyclic ring which may be optionally substituted by halogen;

n is 0, 1, 2 or 3;

each Ra is independently hydrogen, halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$ where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$) alkyl, $C_{1-6}$ alkoxycarbonyl or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or two Ra groups attached to the same carbon atom are =O or two Ra groups attached to adjacent carbon atoms form a bond, or two Ra groups together with the carbon atom to which they are attached form a three- to seven-membered ring, that may be saturated or unsaturated, and that may contain one or two hetero atoms selected from the group consisting of N, O and S, and which may be optionally substituted by one or two $C_{1-6}$ alkyl groups; or two Ra groups together form a group —CH$_2$—, —CH=CH— or —CH$_2$CH$_2$;

p is 0, 1, 2, 3, 4, 5 or 6; q is 0, 1, 2, 3, 4, 5 or 6 provided that p+q is 1, 2, 3, 4, 5 or 6;

$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl; or salts or N-oxides thereof.

2. A method according to claim 1 wherein Y is a single bond or C=O.

3. A method according to claim 1 wherein $R^2$ and $R^3$ are each independently hydrogen, $C_{1-6}$ alkyl, $C_{1-6}$ haloalkyl, $C_{1-6}$ alkoxy or cyano.

4. A method according to claim 1 wherein $R^1$ is hydrogen, $C_{1-6}$ alkyl, $C_{1-6}$ cyanoalkyl, $C_{1-6}$ haloalkyl, $C_{3-7}$ cycloalkyl ($C_{1-4}$)alkyl, $C_{1-6}$ alkoxy($C_{1-6}$)alkyl, heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), aryl($C_{1-6}$)alkyl (wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), $C_{1-6}$ alkylcarbonylamino($C_{1-6}$) alkyl, aryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, phenoxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyloxy (optionally substituted by halo, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ alkynyl, $C_{3-6}$ cycloalkyl, $C_{5-7}$ cycloalkenyl, heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl, $C_{1-6}$ haloalkyl, $C_{1-6}$ alkoxy($C_{1-6}$)alkyl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino, dialkylamino or $C_{1-4}$ alkoxycarbonyl), phenyl ($C_{1-6}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl ($C_{1-6}$) alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen) or heteroaryl (which may be optionally substituted by halo, nitro, cyano, $C_{1-6}$ alkyl, $C_{1-6}$ haloalkyl, $C_{1-6}$ alkoxy or $C_{1-6}$ haloalkoxy, $C_{1-4}$ alkoxycarbonyl $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), amino, $C_{1-6}$ alkylamino or phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino)).

5. A method according to claim 1 wherein each $R^4$ is independently halogen, cyano, $C_{1-8}$ alkyl, $C_{1-8}$ haloalkyl, $C_{1-6}$ cyanoalkyl, $C_{1-6}$ alkoxy($C_{1-6}$)alkyl, $C_{3-7}$ cycloalkyl($C_{1-6}$) alkyl, $C_{5-6}$ cycloalkenyl($C_{1-6}$)alkyl, $C_{3-6}$ alkenyloxy($C_{1-6}$) alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)-alkyl, $C_{1-6}$ alkoxycarbonyl($C_{1-6}$)alkyl, $C_{3-6}$ alkenyloxycarbonyl($C_{1-6}$) alkyl, $C_{3-6}$ alkynyloxycarbonyl($C_{1-6}$)alkyl, aryloxycarbonyl ($C_{1-6}$)alkyl, $C_{1-6}$ alkylthio($C_{1-6}$)alkyl, $C_{1-6}$ alkylsulfinyl ($C_{1-6}$)alkyl, $C_{1-6}$ alkylsulfonyl($C_{1-6}$)alkyl, aminocarbonyl ($C_{1-6}$)alkyl, $C_{1-6}$ alkylaminocarbonyl($C_{1-6}$)alkyl, di($C_{1-6}$) alkylaminocarbonyl($C_{1-6}$) alkyl, phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-4}$) alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the herocycly group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, aminocarbonyl($C_{2-6}$)alkenyl, $C_{1-6}$ alkylaminocarbonyl($C_{2-6}$)alkenyl, di($C_{1-6}$)alkylaminocarbonyl($C_{2-6}$) alkenyl, phenyl($C_{2-4}$)-alkenyl, (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkynyl, trimethylsilyl($C_{2-6}$) alkynyl, aminocarbonyl($C_{2-6}$)alkynyl, $C_{1-6}$ alkylaminocarbonyl($C_{2-6}$)alkynyl, di($C_{1-6}$)alkylaminocarbonyl($C_{2-6}$)alkynyl, $C_{1-6}$ alkoxycarbonyl, $C_{3-7}$ cycloalkyl, $C_{3-7}$ halocycloalkyl, $C_{3-7}$ cyanocycloalkyl, $C_{1-3}$ alkyl($C_{3-7}$)-cycloalkyl, $C_{1-3}$ alkyl($C_{3-7}$)halocycloalkyl,phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), or 2 adjacent groups $R^4$ together with the carbon atoms to which they are attached form a 4, 5, 6 or 7 membered carbocyclic or heterocyclic ring which may be optionally substituted by halogen, $C_{1-8}$ alkoxy, $C_{1-6}$ haloalkoxy, phenoxy (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or $R^{19}R^{20}N$ where $R^{19}$ and $R^{20}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxycarbonyl or $R^{19}$ and $R^{20}$ together with the N atom to which they are attached form a five, six or seven-membered heterocyclic ring which may contain one or two further heteroatoms selected from O, N or S and which may be optionally substituted by one or two $C_{1-6}$ alkyl groups; and n is 0, 1, 2 or 3.

6. A method according to claim 1 wherein $R^8$ is $C_{1-10}$ alkyl, $C_{1-10}$ haloalkyl, aryl($C_{1-6}$)alkyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), arylcarbonyl-($C_{1-6}$) alkyl (wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino and the alkyl group may be optionally substituted by aryl), $C_{2-8}$ alkenyl, $C_{2-8}$ haloalkenyl, aryl($C_{2-6}$)-alkenyl (wherein the aryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), heteroaryl ($C_{2-6}$)-alkenyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), $C_{2-6}$ alkynyl, phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{3-7}$ cycloalkyl, $C_{1-6}$ alkoxycarbonyl, $C_{1-6}$ alkylcarbonyl, $C_{1-6}$ haloalkylcarbonyl or aryl($C_{2-6}$)alkenylcarbonyl (wherein the aryl group may be optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), or —$C(R^{51})(R^{52})$—$[CR^{53}$=$CR^{54}]z$—$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

7. A method according to claim 1 wherein each Ra is hydrogen.

8. A method according to claim 1 wherein p is 1 or 2 and q is 2 or 3.

9. A compound of formula I'

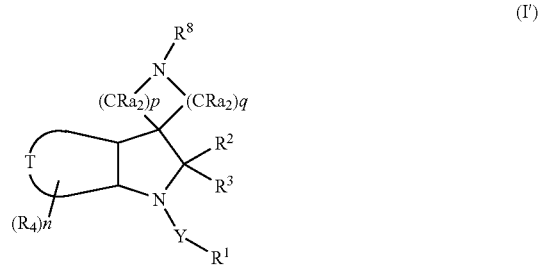

(I')

wherein Y is C=O, C=S;

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$ where $R^{13}$ and $R^{14}$ are independently hydrogen, $COR^{15}$, optionally substituted alkyl, optionally substituted aryl, optionally substituted heteroaryl, optionally substituted heterocyclyl or $R^{13}$ and $R^{14}$ together with the N atom to which they are attached form a group —N=C($R^{16}$)—$NR^{17}R^{18}$; $R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$; $R^{16}$, $R^{17}$ and $R^{18}$ are each independently H or lower alkyl; $R^{19}$ and $R^{20}$ are independently optionally substituted alkyl, optionally substituted aryl or optionally substituted heteroaryl;

$R^2$ and $R^3$ are independently hydrogen, halogen, cyano, optionally substituted alkyl, optionally substituted alkoxy or optionally substituted aryl;

the ring

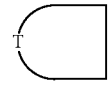

is a 6 membered heteroaromatic ring,

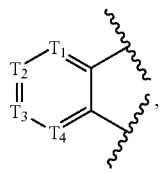

wherein T1 represents N, and each of T2, T3, and T4 represent C;

each $R^4$ is independently halogen, nitro, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or $R^{21}R^{22}N$ where $R^{21}$ and $R^{22}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{21}$ and $R^{22}$ together with the N atom to which they are attached form a five, six or seven-membered heterocyclic ring which may contain one or two further heteroatoms selected from O, N or S and which may be optionally substituted by one or two $C_{1-6}$ alkyl groups, or 2 adjacent groups $R^4$ together with the carbon atoms to which they are attached form a 4, 5, 6, or 7 membered carbocyclic or heterocyclic ring which may be optionally substituted by halogen;

n is 0, 1, 2 or 3;

each Ra is independently hydrogen, halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$ where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or two Ra groups attached to the same carbon atom are =O or two Ra groups attached to adjacent carbon atoms form a bond, or two Ra groups together with the carbon atom to which they are attached form a three- to seven-membered ring, that may be saturated or unsaturated, and that may contain one or two hetero atoms selected from the group consisting of N, O and S, and which may be optionally substituted by one or two $C_{1-6}$ alkyl groups; or two Ra groups together form a group —$CH_2$—, —CH=CH— or —$CH_2CH_2$—;

p is 0, 1, 2, 3, 4, 5 or 6; q is 0, 1, 2, 3, 4, 5 or 6 provided that p+q is 1, 2, 3, 4, 5 or 6;

$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl; or salts or N-oxides thereof.

10. A compound of formula II

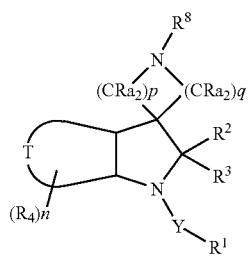

(II)

wherein Y is C=O, C=S;

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$ where $R^{13}$ and $R^{14}$ are independently hydrogen, $COR^{15}$, optionally substituted alkyl, optionally substituted aryl, optionally substituted heteroaryl, optionally substituted heterocyclyl or $R^{13}$ and $R^{14}$ together with the N atom to which they are attached form a group —N=C($R^{16}$)—$NR^{17}R^{18}$; $R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$; $R^{16}$ $R^{17}$ and $R^{18}$ are each independently H or lower alkyl; $R^{19}$ and $R^{20}$ are independently optionally substituted alkyl, optionally substituted aryl or optionally substituted heteroaryl;

$R^2$ and $R^3$ are independently hydrogen, halogen, cyano, optionally substituted alkyl, optionally substituted alkoxy or optionally substituted aryl;

the ring

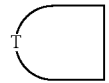

is a 6 membered heteroaromatic ring,

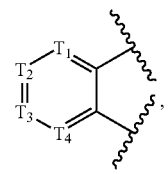

wherein T1 represents N, and each of T2, T3, and T4 represent C;

each $R^4$ is independently halogen, nitro, cyano, optionally substituted $C_{1-8}$ alkyl, optionally substituted $C_{2-6}$ alkynyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or $R^{21}R^{22}N$ where $R^{21}$ and $R^{22}$ are, independently, hydrogen, $C_{1-8}$ alkyl, $C_{3-7}$ cycloalkyl, $C_{3-6}$ alkenyl $C_{3-6}$ alkynyl, $C_{3-7}$cycloalkyl $(C_{1-4})$alkyl, $C_{2-6}$ haloalkyl, $C_{1-6}$ alkoxy$(C_{1-6})$alkyl, $C_{1-6}$ alkoxycarbonyl or $R^{21}$ and $R^{22}$ together with the N atom to which they are attached form a five, six or seven-membered heterocyclic ring which may contain one or two further heteroatoms selected from O, N or S and which may be optionally substituted by one or two $C_{1-6}$ alkyl groups, or 2 adjacent groups $R^4$ together with the carbon atoms to which they are attached form a 4, 5, 6, or 7 membered carbocyclic or heterocyclic ring which may be optionally substituted by halogen;
  $R^8$ is H or tert-butoxycarbonyl;
  n is 0, 1, 2 or 3;
  p is 0, 1, 2, 3, 4, 5 or 6;
  q is 0, 1, 2, 3, 4, 5 or 6 provided that p+q is 1, 2, 3, 4, 5 or 6;
  and Ra is independently hydrogen, halogen, hydroxy, cyano, optionally substituted $C_{1-8}$ alkyl, optionally substituted $C_{2-6}$alkenyl, optionally substituted $C_{2-6}$alkenyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$ where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl $(C_{1-4})$alkyl, $C_{2-6}$ haloalkyl, $C_{1-6}$ alkoxy$(C_{1-6}$ alkyl, $C_{1-6}$ alkoxycarbonyl or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or two Ra groups attached to the same carbon atom are =O or two Ra groups attached to adjacent carbon atoms form a bond, or two Ra groups together with the carbon atom to which they are attached form a three- to seven-membered ring, that may be saturated or unsaturated, and that may contain one or two hetero atoms selected from the group consisting of N, O and S, and which may be optionally substituted by one or two $C_{1-6}$ alkyl groups; or two Ra groups together form a group —$CH_2$—, —CH=CH—or —$CH_2CH_2$.

11. An insecticidal, acaricidal and nematicidal composition comprising an insecticidally, acaricidally or nematicidally effective amount of a compound of formula I' as defined in claim 9.

\* \* \* \* \*